(12) United States Patent
Marasco

(10) Patent No.: US 10,870,694 B2
(45) Date of Patent: Dec. 22, 2020

(54) COMPOSITION AND METHODS OF TREATING B CELL DISORDERS

(71) Applicant: Dana-Farber Cancer Institute, Inc., Boston, MA (US)

(72) Inventor: Wayne A. Marasco, Wellesley, MA (US)

(73) Assignee: Dana Farber Cancer Institute, Inc., Boston, MA (US)

(*) Notice: Subject to any disclaimer, the term of this patent is extended or adjusted under 35 U.S.C. 154(b) by 0 days.

(21) Appl. No.: 16/330,188

(22) PCT Filed: Sep. 5, 2017

(86) PCT No.: PCT/US2017/050093
§ 371 (c)(1),
(2) Date: Mar. 4, 2019

(87) PCT Pub. No.: WO2018/045379
PCT Pub. Date: Mar. 8, 2018

(65) Prior Publication Data
US 2019/0276523 A1    Sep. 12, 2019

Related U.S. Application Data

(60) Provisional application No. 62/383,004, filed on Sep. 2, 2016, provisional application No. 62/384,397, filed on Sep. 7, 2016.

(51) Int. Cl.
| | |
|---|---|
| *A61K 39/395* | (2006.01) |
| *C07K 16/18* | (2006.01) |
| *A61P 35/02* | (2006.01) |
| *C07K 16/42* | (2006.01) |
| *C07K 16/28* | (2006.01) |
| *A61K 39/00* | (2006.01) |

(52) U.S. Cl.
CPC ........ *C07K 16/18* (2013.01); *A61K 39/39566* (2013.01); *A61P 35/02* (2018.01); *C07K 16/2803* (2013.01); *C07K 16/4241* (2013.01); *A61K 2039/505* (2013.01); *A61K 2039/545* (2013.01); *C07K 2317/24* (2013.01); *C07K 2317/35* (2013.01); *C07K 2317/565* (2013.01); *C07K 2317/622* (2013.01); *C07K 2317/732* (2013.01); *C07K 2317/734* (2013.01); *C07K 2317/76* (2013.01); *C07K 2317/92* (2013.01); *C07K 2319/30* (2013.01)

(58) Field of Classification Search
None
See application file for complete search history.

(56) References Cited

U.S. PATENT DOCUMENTS

| | | |
|---|---|---|
| 4,485,045 A | 11/1984 | Regen |
| 4,522,811 A | 6/1985 | Eppstein et al. |
| 4,544,545 A | 10/1985 | Ryan et al. |
| 4,661,586 A | 4/1987 | Levy et al. |
| 4,676,980 A | 6/1987 | Segal et al. |
| 4,699,880 A | 10/1987 | Goldstein |
| 4,816,567 A | 3/1989 | Cabilly et al. |
| 4,946,778 A | 8/1990 | Ladner et al. |
| 5,013,556 A | 5/1991 | Woodle et al. |
| 5,030,719 A | 7/1991 | Umemoto et al. |
| 5,091,513 A | 2/1992 | Huston et al. |
| 5,132,405 A | 7/1992 | Huston et al. |
| 5,496,549 A | 3/1996 | Yamazaki et al. |
| 5,545,806 A | 8/1996 | Lonberg et al. |
| 5,545,807 A | 8/1996 | Surani et al. |
| 5,569,825 A | 10/1996 | Lonberg et al. |
| 5,582,996 A | 12/1996 | Curtis |
| 5,601,819 A | 2/1997 | Wong et al. |
| 5,625,126 A | 4/1997 | Lonberg et al. |
| 5,633,425 A | 5/1997 | Lonberg et al. |
| 5,643,759 A | 7/1997 | Pfreundschuh |
| 5,661,016 A | 8/1997 | Lonberg et al. |
| 5,807,706 A | 9/1998 | Carter et al. |
| 5,821,333 A | 10/1998 | Carter et al. |
| 5,833,985 A | 11/1998 | Ball et al. |
| 5,861,510 A | 1/1999 | Piscopio et al. |
| 5,863,949 A | 1/1999 | Robinson et al. |
| 5,916,771 A | 6/1999 | Hori et al. |
| 5,932,448 A | 8/1999 | Tso et al. |
| 5,959,083 A | 9/1999 | Bosslet et al. |
| 5,959,084 A | 9/1999 | Ring et al. |
| 5,989,530 A | 11/1999 | Lorenz et al. |
| 6,010,902 A | 1/2000 | Ledbetter et al. |
| 6,037,453 A | 3/2000 | Jardieu et al. |
| 6,060,285 A | 5/2000 | Lenz et al. |
| 6,106,833 A | 8/2000 | Ring et al. |

(Continued)

FOREIGN PATENT DOCUMENTS

| | | |
|---|---|---|
| EP | 0606046 | 7/1994 |
| EP | 0780386 | 6/1997 |

(Continued)

OTHER PUBLICATIONS

Chang et al (MABS, 2016, 8:787-798, published online Mar. 10, 2016).*
O'Brien et al (Clinical Advances in Hematology & Oncology, 2011, 9:22-31).*
Ricci et al (Therapeutics and Clinical Risk Management, 2009, 5:187-207).*
Int'l Search Report dated Mar. 5, 2019.
Ivanovski M, Silvestri F, Pozzato G, Anand S, Mazzaro C, Burrone OR, et al. Somatic hypermutation, clonal diversity, and preferential expression of the VH 51p1/NL kv325 immunoglobulin gene combination in hepatitis C virus-associated immunocytomas. Blood 1998; 91 :2433-42.
Jansen et al., Immunological Reviews 62: 185-216 (1982).

(Continued)

*Primary Examiner* — Laura B Goddard
(74) *Attorney, Agent, or Firm* — Baker Donelson

(57) ABSTRACT

The present invention comprises methods of using a humanized monoclonal antibody that binds to the human immunoglobulin heavy chain variable region germline gene VH1-69 to treat B-cell disorders.

12 Claims, 16 Drawing Sheets

Specification includes a Sequence Listing.

(56) References Cited

U.S. PATENT DOCUMENTS

| | | | |
|---|---|---|---|
| 6,132,992 A | 10/2000 | Ledbetter et al. | |
| 6,193,967 B1 | 2/2001 | Morganelli | |
| 6,210,668 B1 | 4/2001 | Lindhofer et al. | |
| 6,403,588 B1 | 6/2002 | Hayakawa et al. | |
| 6,602,684 B1 | 8/2003 | Umana et al. | |
| 6,608,053 B2 | 8/2003 | Hayakawa et al. | |
| 6,608,056 B1 | 8/2003 | Hayakawa et al. | |
| 6,653,320 B2 | 11/2003 | Hayakawa et al. | |
| 6,703,414 B2 | 3/2004 | Powis et al. | |
| 6,770,641 B2 | 8/2004 | Hayakawa et al. | |
| 6,838,457 B2 | 1/2005 | Hayakawa et al. | |
| 6,894,055 B2 | 5/2005 | Melese et al. | |
| 6,908,932 B2 | 6/2005 | Melese et al. | |
| 6,946,292 B2 | 9/2005 | Kanda et al. | |
| 7,037,915 B2 | 5/2006 | Hayakawa et al. | |
| 7,064,191 B2 | 6/2006 | Shinkawa et al. | |
| 7,141,576 B2 | 11/2006 | Lackey et al. | |
| 7,173,029 B2 | 2/2007 | Hayakawa et al. | |
| 7,227,003 B2 | 6/2007 | Le et al. | |
| 7,691,568 B2 | 4/2010 | Niwa et al. | |
| 7,749,753 B2 | 7/2010 | Kanda et al. | |
| 7,846,434 B2 | 12/2010 | Espling et al. | |
| 8,846,871 B2 | 9/2014 | Siebel et al. | |
| 9,527,924 B2 * | 12/2016 | Marasco | C07K 16/1018 |
| 10,179,822 B2 * | 1/2019 | Marasco | C07K 16/1018 |
| 2003/0003097 A1 | 1/2003 | Reff et al. | |
| 2003/0157108 A1 | 8/2003 | Presta | |
| 2004/0092561 A1 | 5/2004 | Ruckle et al. | |
| 2004/0093621 A1 | 5/2004 | Shitara et al. | |
| 2004/0110704 A1 | 6/2004 | Yamane et al. | |
| 2004/0132140 A1 | 7/2004 | Satoh et al. | |
| 2005/0123546 A1 | 6/2005 | Umana et al. | |
| 2007/0298040 A1 | 12/2007 | Le et al. | |
| 2013/0243749 A1 * | 9/2013 | Marasco | C07K 16/1018 424/131.1 |

FOREIGN PATENT DOCUMENTS

| | | |
|---|---|---|
| EP | 818442 | 12/1998 |
| EP | 0931788 | 8/1999 |
| EP | 1004578 | 6/2000 |
| EP | 1417976 | 5/2004 |
| JP | 08175990 | 7/1996 |
| JP | 08176070 | 7/1999 |
| JP | 2001247477 | 9/2001 |
| WO | 90/05719 | 5/1990 |
| WO | 91/00360 | 1/1991 |
| WO | 92/00373 | 1/1992 |
| WO | 93/08829 | 5/1993 |
| WO | 94/02602 | 2/1994 |
| WO | 94/11026 | 5/1994 |
| WO | 95/22618 | 8/1995 |
| WO | 96/27583 | 9/1996 |
| WO | 96/33172 | 10/1996 |
| WO | 96/33735 | 10/1996 |
| WO | 96/34096 | 10/1996 |
| WO | 97/15658 | 5/1997 |
| WO | 97/22596 | 6/1997 |
| WO | 97/30035 | 8/1997 |
| WO | 1997/30087 | 8/1997 |
| WO | 97/32856 | 9/1997 |
| WO | 98/03516 | 1/1998 |
| WO | 98/07697 | 2/1998 |
| WO | 98/13354 | 4/1998 |
| WO | 98/30566 | 7/1998 |
| WO | 98/33768 | 8/1998 |
| WO | 98/34915 | 8/1998 |
| WO | 98/34918 | 8/1998 |
| WO | 98/35985 | 8/1998 |
| WO | 1998/58964 | 12/1998 |
| WO | 99/07675 | 2/1999 |
| WO | 1999/22764 | 5/1999 |
| WO | 99/29667 | 6/1999 |
| WO | 99/52910 | 10/1999 |
| WO | 99/53049 | 10/1999 |
| WO | 052889 | 10/1999 |
| WO | 54342 | 10/1999 |
| WO | 0042072 | 7/2000 |
| WO | 0047212 | 8/2000 |
| WO | 2000/61739 | 10/2000 |
| WO | 2001/29246 | 4/2001 |
| WO | 01/60814 | 8/2001 |
| WO | 2003/011878 | 2/2003 |
| WO | 11878 | 2/2003 |
| WO | 2003/034997 | 5/2003 |
| WO | 2003/035618 | 5/2003 |
| WO | 2003/037886 | 5/2003 |
| WO | 74679 | 9/2003 |
| WO | 2003/085119 | 10/2003 |
| WO | 084570 | 10/2003 |
| WO | 2004/006916 | 1/2004 |
| WO | 2004/007491 | 1/2004 |
| WO | 2004/017950 | 3/2004 |
| WO | 029207 | 4/2004 |
| WO | 2004/056312 | 7/2004 |
| WO | 2004/099249 | 11/2004 |
| WO | 2005/035586 | 4/2005 |
| WO | 2005/035778 | 4/2005 |
| WO | 2005/053742 | 6/2005 |
| WO | 2006/019447 | 2/2006 |
| WO | 2006/046031 | 5/2006 |
| WO | 2006/046035 | 5/2006 |
| WO | 2006/046040 | 5/2006 |
| WO | 2006/047350 | 5/2006 |
| WO | 2006/105338 | 10/2006 |
| WO | 2007/041635 | 4/2007 |
| WO | 2007/042806 | 4/2007 |
| WO | 2007/042810 | 4/2007 |
| WO | 2011/53380 | 5/2011 |

OTHER PUBLICATIONS

Jilani I, O'Brien S, Manshuri T, Thomas DA, Thomazy VA, Imam M, et al. Transient down-modulation of CD20 by rituximab in patients with chronic lymphocytic leukemia. Blood 2003; 102:3514-20.

Jones PT, Dear PH, Foote J, Neuberger MS, Winter G. Replacing the complementarity—determining regions in a human antibody with those from a mouse. Nature 1986; 321 :522-5.

Kaplitt, M. G.. et al., Nat. Genet. 8: 148 (1994).

Killen and Lindstrom, Jour. Immun. 133: 1335-2549 (1984).

Kohler and Milstein, Nature, 256:495 (1975).

Kozbor, et al., 1983 Immunol Today 4: 72.

Kozbor, J. Immunol., 133 :3001 (1984).

Krause, G., et al. "Action of novel CD37 antibodies on chronic lymphocytic leukemia cells." Leukemia 26.3 (2012): 546-549.

Lanasa MC. Novel insights into the biology of CLL. Hematology Am Soc Hematol Educ Program 2010; 2010:70-6.

Lanasa, Mark C., et al. "Immunophenotypic and gene expression analysis of monoclonal B-cell lymphocytosis shows biologic characteristics associated with good prognosis CLL" Leukemia 25.9 (2011): 1459-1466.

Lazar, Greg A., et al. "Engineered antibody Fc variants with enhanced effector function." Proceedings of the National Academy of Sciences 103.11 (2006): 4005-4010.

LeGal LaSalle et al., Science, 259:988 (1993).

Levy R, Ganjoo KN, Leonard JP, Vose JM, Flinn TvV, Ambinder RF, et al. Active idiotypic vaccination versus control immunotherapy for follicular lymphoma. J Clin Oncol 2014; 32: 1797-803.

Lim, F., et al., in DNA Cloning: Mammalian Systems, D. Glover, Ed. (Oxford Univ. Press, Oxford England) (1995).

Lonberg and Huszar, Intern. Rev. Immunol. 13 65-93 (1995).

Lonberg et al., Nature 368 856-859 (1994).

Long BR, Stoddart CA. Alpha interferon and HIV infection cause activation of human T cells in NSG-BLT mice. Journal of virology 2012; 86:3327-36.

Mader A, Kunert R. Humanization strategies for an anti-idiotypic antibody mimicking HIV-1 gp41. Protein Eng Des Sel 2010; 23 :947-54.

(56) References Cited

OTHER PUBLICATIONS

Malmqvist, Magnus. "Biospecific interaction analysis using biosensor technology." Nature 361.6408 (1993): 186-187.
Marasco R, Vaccari P, Luppi M, Zucchini P, Castelli I, Barozzi P, et al. Immunoglobulin gene mutations and frequent use of VHI-69 and VH4-34 segments in hepatitis C virus-positive and hepatitis C virus-negative nodal marginal zone B-cell lymphoma. Am J Pathol 2001; 159:253-61.
Marks et aL, Bio/Technology 10, 779-783 (1992).
Marks et al., J. Mol. Biol., 222:581 (1991).
Martin et al., J. Biol. Chem., 257: 286-288 (1982.
Messmer BT, Albesiano E, Efremov DG, Ghiotto F, Allen SL, Kolitz J, et al. Multiple distinct sets of stereotyped antigen receptors indicate a role for antigen in promoting chronic lymphocytic leukemia. J Exp Med 2004; 200:519-25.
Messmer, Bradley T., et al. "The pattern and distribution of immunoglobulin VH gene mutations in chronic lymphocytic leukemia B cells are consistent with the canonical somatic hypermutation process." Blood 103.9 (2004): 3490-3495.
Morrison et al., Am. J. Physiol. 266:292-305 (1994).
Morrison, Nature 368, 812-13 (1994).
Munson and Pollard, Anal. Biochem., 107:220 (1980).
Murray F, Darzentas N, Hadzidimitriou A, Tobin G, Boudjogra M, Scielzo C, et al. Stereotyped patterns of somatic hypermutation in subsets of patients with chronic lymphocytic leukemia: implications for the role of antigen selection in leukemogenesis. Blood 2008; 111: 1524-33.
Neuberger, Nature Biotechnology 14, 826 (1996).
Pos W, Luken BM, Kremer Hovinga JA, Turenhout EA, Scheiflinger F, Dong JF, et al. VFI1-69 germline encoded antibodies directed towards ADAMTSI3 in patients with acquired thrombotic thrombocytopenic purpura. Journal of thrombosis and haemostasis : JTH 2009; 7:421-8.
Potter KN, Orchard J, Critchley E, Mockridge CI, Jose A, Stevenson FK. Features of the overexpressed VI-69 genes in the unmutated subset of chronic lymphocytic leukemia are distinct from those in the healthy elderly repertoire. Blood 2003; 101 :3082-4.
Presta LG, Chen H, O'Connor SJ, Chisholm V, Meng YG, Krummen L, et al. Humanization of an anti-vascular endothelial growth factor monoclonal antibody for the therapy of solid tumors and other disorders. Cancer Res 1997; 57:4593-9.
Ramakrishnan, S. et al., Cancer Res. 44:201-208 (1984).
Reif ME, Camer K, Chambers KS, Chinn PC, Leonard JE, Raab R, et al. Depletion of B cells in vivo by a chimeric mouse human monoclonal antibody to CD20. Blood 1994; 83 :435-45.
Shields, Robert L., et al. "High resolution mapping of the binding site on human IgG1 for Fc?RI, Fc?RII, Fc?RIII, and FcRn and design of IgG1 variants with improved binding to the Fc?R." Journal of Biological Chemistry 276.9 (2001): 6591-6604.
Shopes, J. Immunol., 148: 2918-2922 (1992).
Stamatopoulos K, Belessi C, Moreno C, Boudjograh M, Guida G, Smilevska T, et al. Over 20% of patients with chronic lymphocytic leukemia carry stereotyped receptors: Pathogenetic implications and clinical correlations. Blood 2007; 109:259-70. 22.
Stevenson et al., Anti-Cancer Drug Design, 3 : 219-230 (1989).
Sui J, Li W, Murakami A, Tamin A, Matthews LJ, Wong SK, et al. Potent neutralization of severe acute respiratory syndrome (SARS) coronavirus by a human mAb to SI protein that blocks receptor association. Proceedings of the National Academy of Sciences of the United States of America 2004; 101 :2536-41.
Taube R, Zhu Q, Xu C, Diaz-Griffero F, Sui J, Kamau E, et al. Lentivirus display: stable expression of human antibodies on the surface of human cells and virus particles. PLoS One 2008; 3 :e3181.
Timmerman JM, Czerwinski DK, Davis TA, Hsu FJ, Benike C, Hao ZM, et al. Idiotype—pulsed dendritic cell vaccination for B-cell lymphoma: clinical and immune responses in 35 patients. Blood 2002; 99: 1517-26.

Traunecker, André, Antonio Lanzavecchia, and Klaus Karjalainen. "Bispecific single chain molecules (Janusins) target cytotoxic lymphocytes on HIV infected cells." The EMBO Journal 10.12 (1991): 3655-3659.
Umaria, Pablo, et al. "Engineered glycoforms of an antineuroblastoma IgG1 with optimized antibody-dependent cellular cytotoxic activity." Nature biotechnology 17.2 (1999): 176-180.
Vitetta et al., Science 238: 1098 (1987).
Nhitelegg NR, Rees AR. WAM: an improved algorithm for modelling antibodies on the WEB. Protein Eng 2000; 13 :819-24.
Widhopf GF, 2nd, Kipps TJ. Normal B cells express 51pl-encoded lg heavy chains that are distinct from those expressed by chronic lymphocytic leukemia B cells. J Immunol 2001; 166:95-102.
"Conjugate Vaccines", Contributions to Microbiology and Immunology, J. M. Cruse and R. E. Lewis, Jr (eds), Carger Press, New York, (1989).
American Cancer Society: Cancer Facts and Figures 2015. Atlanta, GA: American Cancer Society, 2015.
Antibodies: A Laboratory Manual, Harlow E, and Lane D, 1988, Cold Spring Harbor Laboratory Press, Cold Spring Harbor, NY.
Bagnara D, Kaufman MS, Calissano C, Marsilio S, Patten PE, Simone R, et al. A novel adoptive transfer model of chronic lymphocytic leukemia suggests a key role for T lymphocytes in the disease. Blood 2011; 117:5463-72.
Barbas et al., Proc. Natl. Acad. Sci. USA 89:9339-43 (1992).
Becker PD, Legrand N, van Geelen CM, Noerder M, Huntington ND, Lim A, et al. Generation of human antigen-specific monoclonal IgM antibodies using vaccinated "human immune system" mice. PLoS One 2010; 5.
Bertilaccio MT, Scielzo C, Simonetti G, Ten Hacken E, Apollonio B, Ghia P, et al. Xenograft models of chronic lymphocytic leukemia: problems, pitfalls and future directions. Leukemia 2013; 27:534-40.
Biswas S, Chang H, Sarkis PT, Fikrig E, Zhu Q, Marasco WA. Humoral immune responses in humanized BLT mice immunized with West Nile virus and HIV-1 envelope proteins are largely mediated via human CD5+ B cells. Immunology 2011; 134:419-33.
Bobo et al., Proc. Natl. Acad. Sci. USA 91 :2076-2080 (1994).
Boyd SD, Gaeta BA, Jackson KJ, Fire AZ, Marshall EL, Merker JD, et al. Individual variation in the germline lg gene repertoire inferred from variable region gene rearrangements. J Immunol 2010; 184:6986-92.
Brezinschek HP, Brezinschek RI, Dorner T, Lipsky PE. Similar characteristics of the CDR3 of V(H)I-69/DP-10 rearrangements in normal human peripheral blood and chronic lymphocytic leukaemia B cells. Br J Haematol 1998; 102:516-21.
Brodeur et al., Monoclonal Antibody Production Techniques and Applications, Marcel Dekker, Inc., New York, (1987) pp. 51-63.
Byrd, John C., et al. "A phase 1 and pharmacodynamic study of depsipeptide (FK228) in chronic lymphocytic leukemia and acute myeloid leukemia." Blood 105.3 (2005): 959-967.
Byrd John C., et al. "Flavopiridol administered using a pharmacologically derived schedule is associated with marked clinical efficacy in refractory, genetically high-risk chronic lymphocytic leukemia." Blood 109.2 (2007): 399-404.
Byrd, John C., et al. "Rituximab using a thrice weekly dosing schedule in B-cell chronic lymphocytic leukemia and small lymphocytic lymphoma demonstrates clinical activity and acceptable toxicity." Journal of Clinical Oncology 19.8 (2001): 2153-2164.
Caron et al., J. Exp Med., 176: 1191-1195 (1992).
Carter P, Presta L, Gorman CM, Ridgway JB, Henner D, Wong WL, et al. Humanization of an anti-pl85HER2 antibody for human cancer therapy. Proc Natl Acad Sci U S A 1992; 89:4285-9.
Chang DK, Sui J, Geng S, Muvaffak A, Bai M, Fuhlbrigge RC, et al. Humanization of an anti-CCR4 antibody that kills cutaneous T-cell lymphoma cells and abrogates suppression by T-regulatory cells. Mol Cancer Ther 2012; 11 :2451-61.
Chang H, Biswas S, Tallarico AS, Sarkis PT, Geng S, Panditrao MM, et al. Human B-cell ontogeny in humanized NOD/SCID gammac(null) mice generates a diverse yet auto/poly- and HIV-1-reactive antibody repertoire. Genes Immun 2012; 13 :399-410.
Chiorazzi Nicholas, Kanti R. Rai, and Manlio Ferrarini. "Chronic lymphocytic leukemia." New England Journal of Medicine 352.8 (2005): 804-815.

(56) References Cited

OTHER PUBLICATIONS

Cole, et al., 1985 In: Monoclonal Antibodies and Cancer Therapy, Alan R. Liss, Inc., pp. 77-96.
Cote, et al., 1983. Proc Natl Acad Sci USA 80: 2026-2030.
D. Wilkinson (The Scientist, published by the Scientist, Inc. ,Philadelphia PA, vol. 14, No. 8 (Apr. 17, 2000), pp. 25-28).
Damle, Rajendra N., et al. "Ig V Gene Mutation Status and CD38 Expression As Novel Prognostic Indicators in Chronic Lymphocytic Leukemia: Presented in part at the 40th Annual Meeting of The American Society of Hematology, held in Miami Beach, FL, Dec. 4-8, 1998." Blood, The Journal of the American Society of Hematology 94.6 (1999): 1840-1847.
Darzentas N, Hadzidimitriou A, Murray F, Hatzi K, Josefsson P, Laoutaris N, et al. A different ontogenesis for chronic lymphocytic leukemia cases carrying stereotyped antigen receptors: molecular and computational evidence. Leukemia 2010; 24: 125-32.
Davidson, et al., Nat. Genet 3 :219 (1993).
Davies et al. (1990) Annual Rev Biochem 59:439-473.
Durig J, Ebeling P, Grabellus F, Sorg UR, Mollmann M, Schutt P, et al. A novel nonobese diabetic/severe combined immunodeficient xenograft model for chronic lymphocytic leukemia reflects important clinical characteristics of the disease. Cancer Res 2007; 67:8653-61.
Epstein et al., Proc. Natl. Acad. Sci. USA, 82: 3688 (1985).
Fais, Franco, et al. "Chronic lymphocytic leukemia B cells express restricted sets of mutated and unmutated antigen receptors." The Journal of clinical investigation 102.8 (1998): 1515-1525.
Fishwild et al, Nature Biotechnology 14, 845-51 (1996).
Forconi F, Potter KN, Wheatley I, Darzentas N, Sozzi E, Stamatopoulos K, et al. The normal IGHVI-69-derived B-cell repertoire contains stereotypic patterns characteristic of unmutated CLL. Blood 2010; 115:71-7.
Garcia-Escobar, I., et al. "Therapeutic management of chronic lymphocytic leukaemia: state of the art and future perspectives." Critical reviews in oncology/hematology 80.1 (2011): 100-113.
Geller, A. I. et al., J. Neurochem, 64:487 (1995).
Geller, A. I. et al., Proc Natl. Acad. Sci. : U.S.A. 90:7603 (1993).
Seller, A. L, et al., Proc Natl. Acad. Sci USA 87: 1149 (1990).
Ghia, Paolo, et al. "Geographic patterns and pathogenetic implications of IGHV gene usage in chronic lymphocytic leukemia: the lesson of the IGHV3-21 gene." Blood 105.4 (2005): 1678-1685.
Goding, Monoclonal Antibodies: Principles and Practice, Academic Press, (1986) pp. 59-103.
Golay J, Lazzari M, Facchinetti V, Bemasconi S, Borleri G, Barbui T, et al. CD20 levels determine the in vitro susceptibility to rituximab and complement of B-cell chronic lymphocytic leukemia: further regulation by CD55 and CD59. Blood 2001; 98:3383-9.

Guex N, Peitsch MC Swiss-Model and the Swiss-Pdb Viewer: an environment for comparative protein modeling. Electrophoresis 1997; 18:2714-23.
Hallek, Michael, et al. "Guidelines for the diagnosis and treatment of chronic lymphocytic leukemia: a report from the International Workshop on Chronic Lymphocytic Leukemia updating the National Cancer Institute—Working Group 1996 guidelines." Blood, The Journal of the American Society of Hematology 111.12 (2008): 5446-5456.
Hamblin, Terry J., et al. "Unmutated Ig VH genes are associated with a more aggressive form of chronic lymphocytic leukemia." Blood, The Journal of the American Society of Hematology 94.6 (1999): 1848-1854.
Han T, Abdel-Motal UM, Chang DK, Sui J, Muvaffak A, Campbell J, et al. Human anti-CCR4 minibody gene transfer for the treatment of cutaneous T-cell lymphoma. PLoS One 2012; 7:e44455.
Hayashi T, Treon SP, Hideshima T, Tai YT, Akiyama M, Richardson P, et al. Recombinant humanized anti-CD40 monoclonal antibody triggers autologous antibody-dependent cell-mediated cytotoxicity against multiple myeloma cells. Br J Haematol 2003; 121 :592-6.
Herman, Sarah EM, et al. "Phosphatidylinositol 3-kinase-d inhibitor CAL-101 shows promising preclinical activity in chronic lymphocytic leukemia by antagonizing intrinsic and extrinsic cellular survival signals." Blood, The Journal of the American Society of Hematology 116.12 (2010): 2078-2088.
Hezareh M, Hessell AJ, Jensen RC, van de Winkel JG, Parren PW. Effector function activities of a panel of mutants of a broadly neutralizing antibody against human immunodeficiency virus type 1. J Virol 2001; 75: 12161-8.
Hoogenboom and Winter, J. Mol. Biol., 227:381 (1991).
Ruse, et al., 1989 Science 246: 1275-1281.
Huston et al. (1988) Proc Nat Acad Sci USA 85(16):5879-5883.
Hwang et al., Proc. Natl Acad. Sci. USA, 77: 4030 (1980).
Widhopf GF, 2nd, Rassenti LZ, Toy TL, Gribben JG, Wierda WG, Kipps TJ. Chronic lymphocytic leukemia B cells of more than 1% of patients express virtually identical immunoglobulins. Blood 2004; 104:2499-504.
Yaguchi, Shin-ichi, et al. "Antitumor activity of ZSTK474, a new phosphatidylinositol 3-kinase inhibitor." Journal of the National Cancer Institute 98.8 (2006): 545-556.
Yamane-Ohnuki, Naoko, et al. "Establishment of FUT8 knockout Chinese hamster ovary cells: An ideal host cell line for producing completely defucosylated antibodies with enhanced antibody-dependent cellular cytotoxicity." Biotechnology and bioengineering 87.5 (2004): 614-622.
Yang, et al., J. Virol. 69:2004 (1995).
Zebedee et al., Proc. Natl. Acad. Sci. USA 89:3175-79 (1992).
Brian C. Miller, et al. "CD19-Targeted Cart Cells: A New Tool in the Fight against B Cell Malignancies", Oncology Research and Treatment, vol. 38, No. 12, Nov. 18, 2015, pp. 683-690.

* cited by examiner

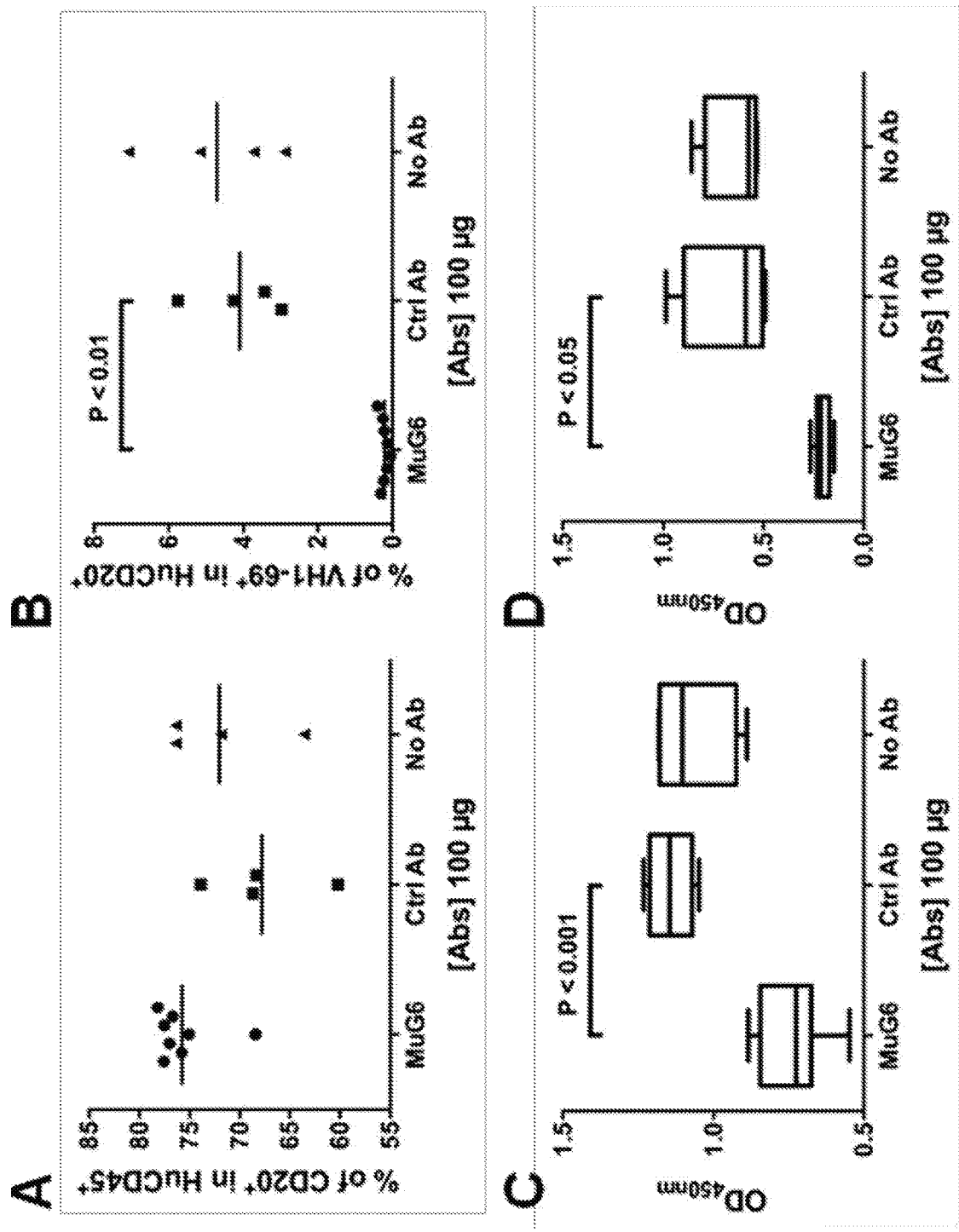
Figure 1. The In vivo function of MuG6 in the humanized GTL mice model.

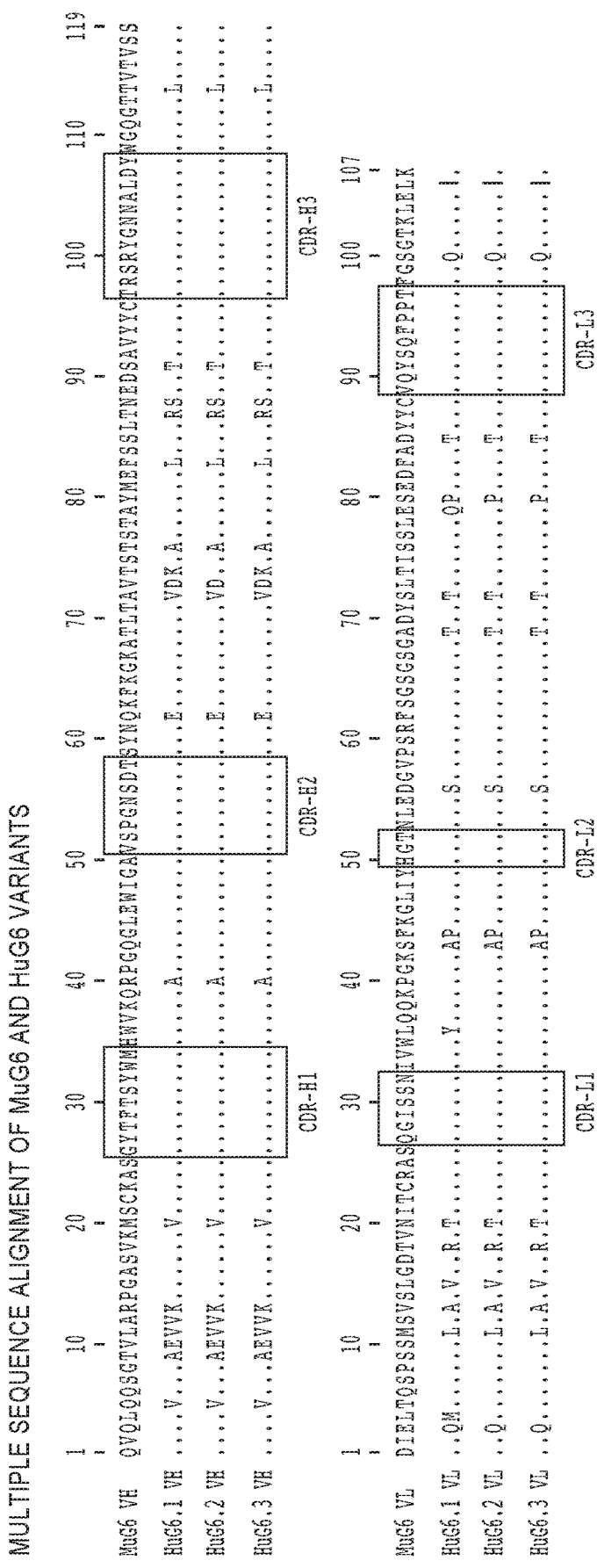
Figure 2. Amino acid sequence alignment of the rearranged mouse and humanized variable heavy (VH) and variable light kappa (VK) domains.

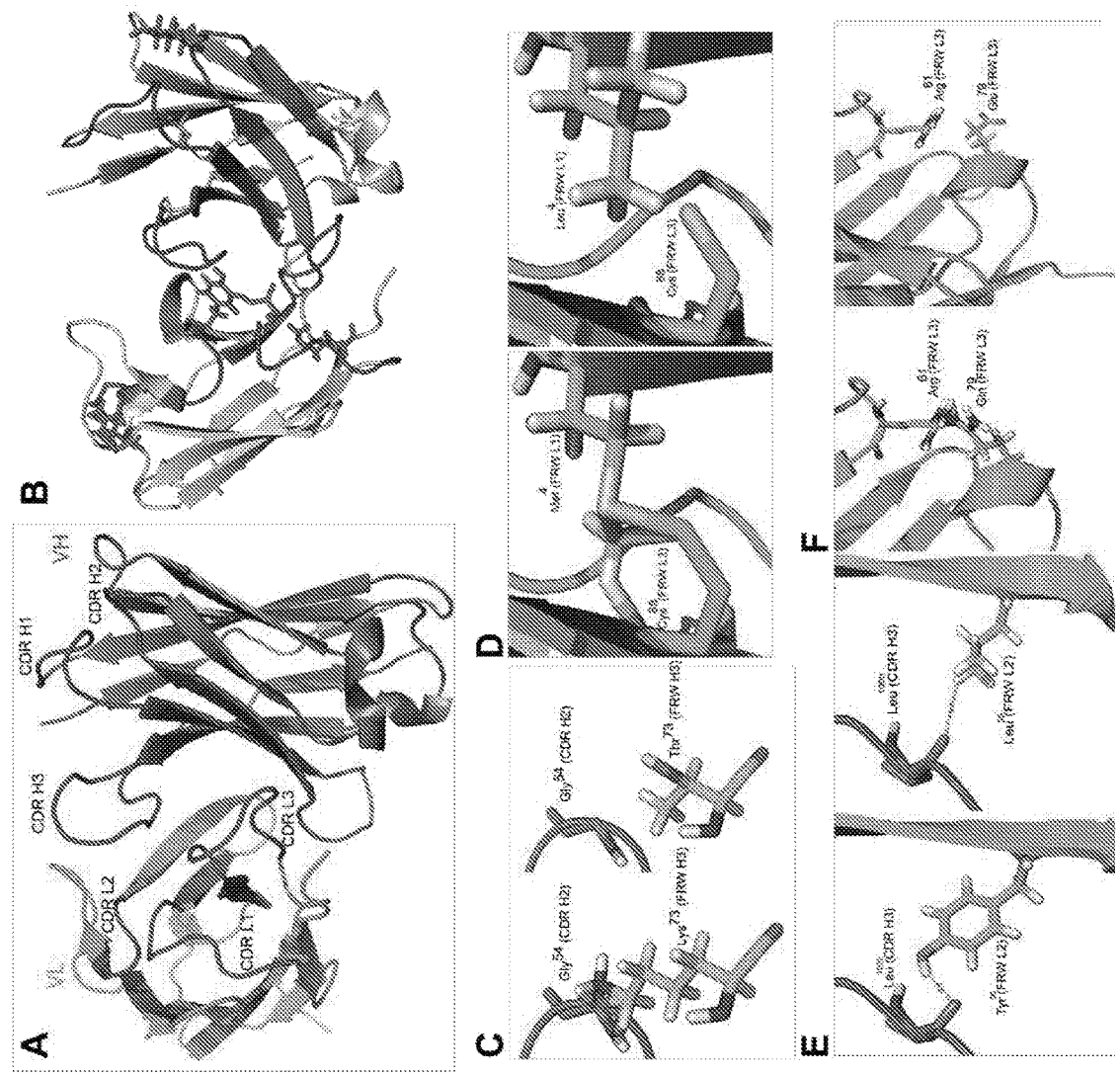
Figure 3. Antibody structural homology model.

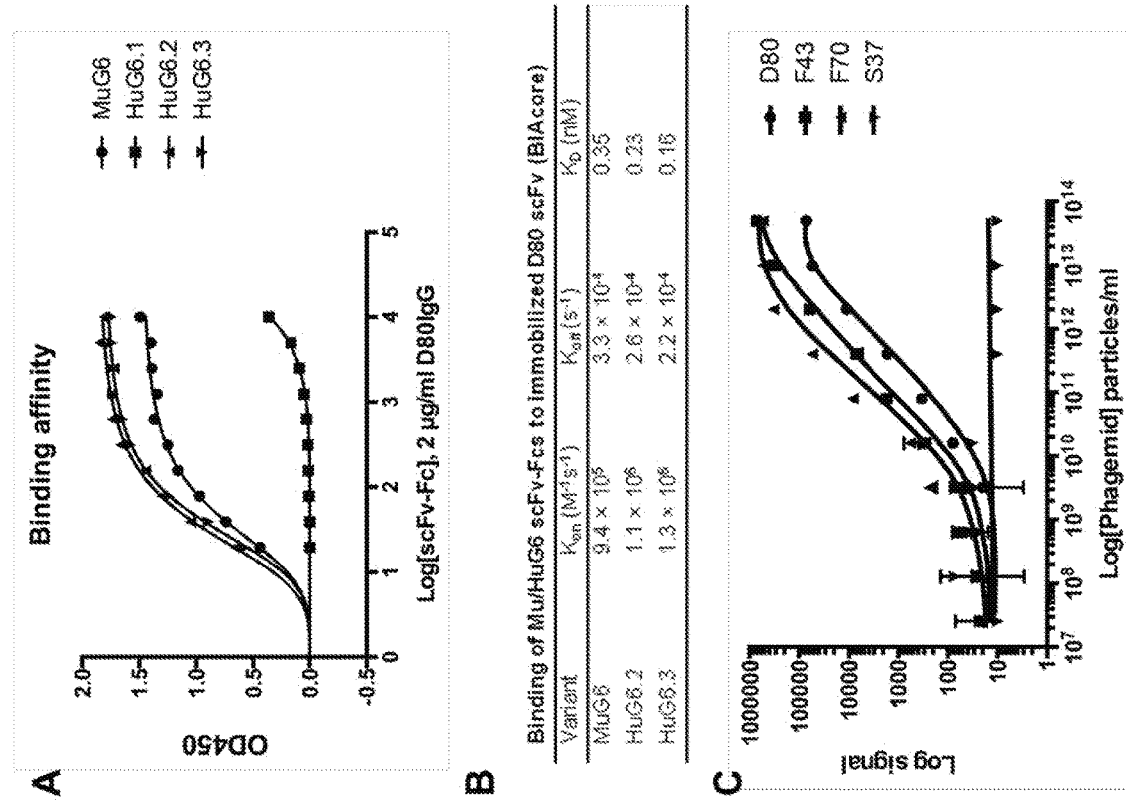
Figure 4. Binding affinity and kinetics of MuG6 and HuG6s

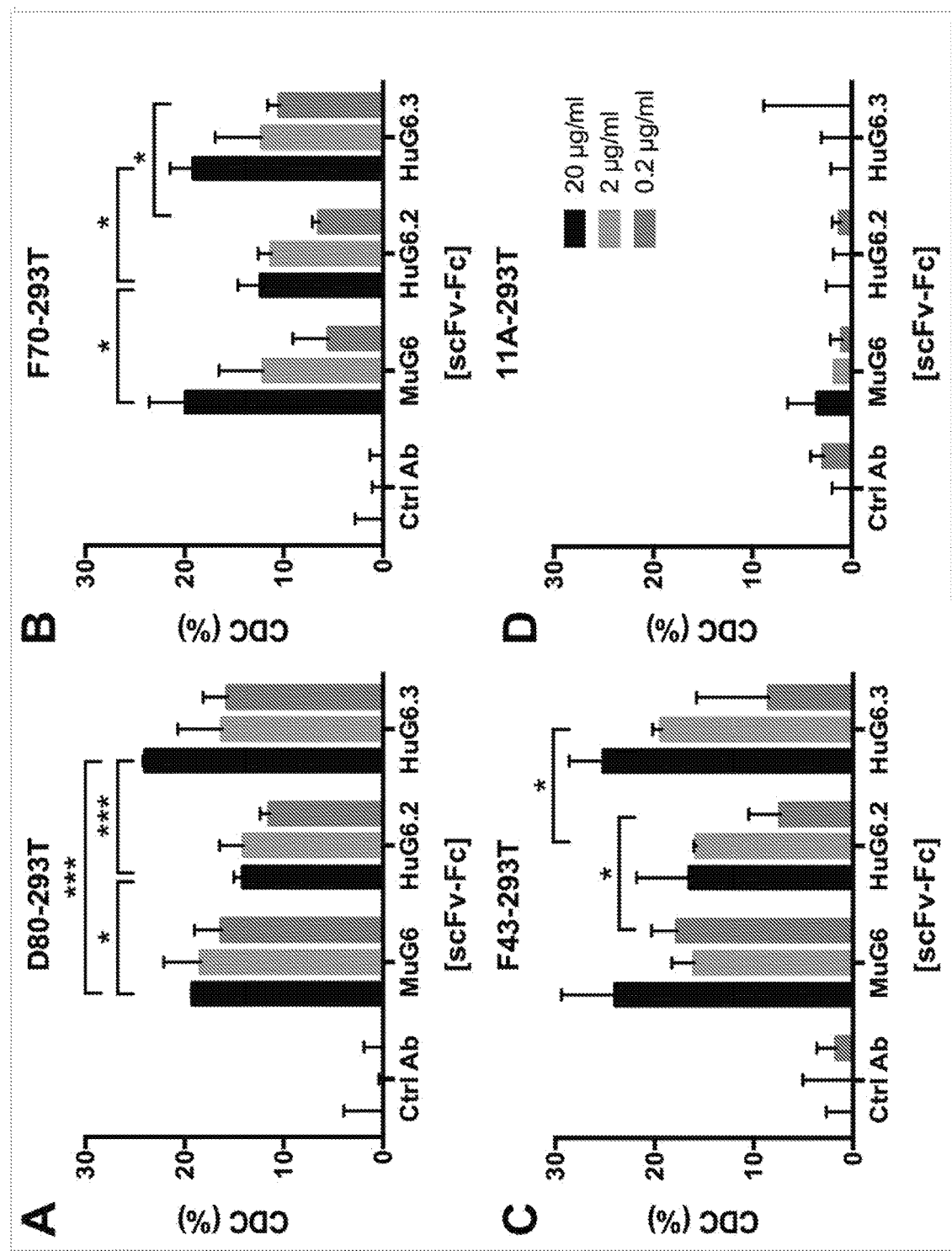
Figure 5. Mu/HuG6s mediate killing of *IGHV1-69*-expressing cells via CDC.

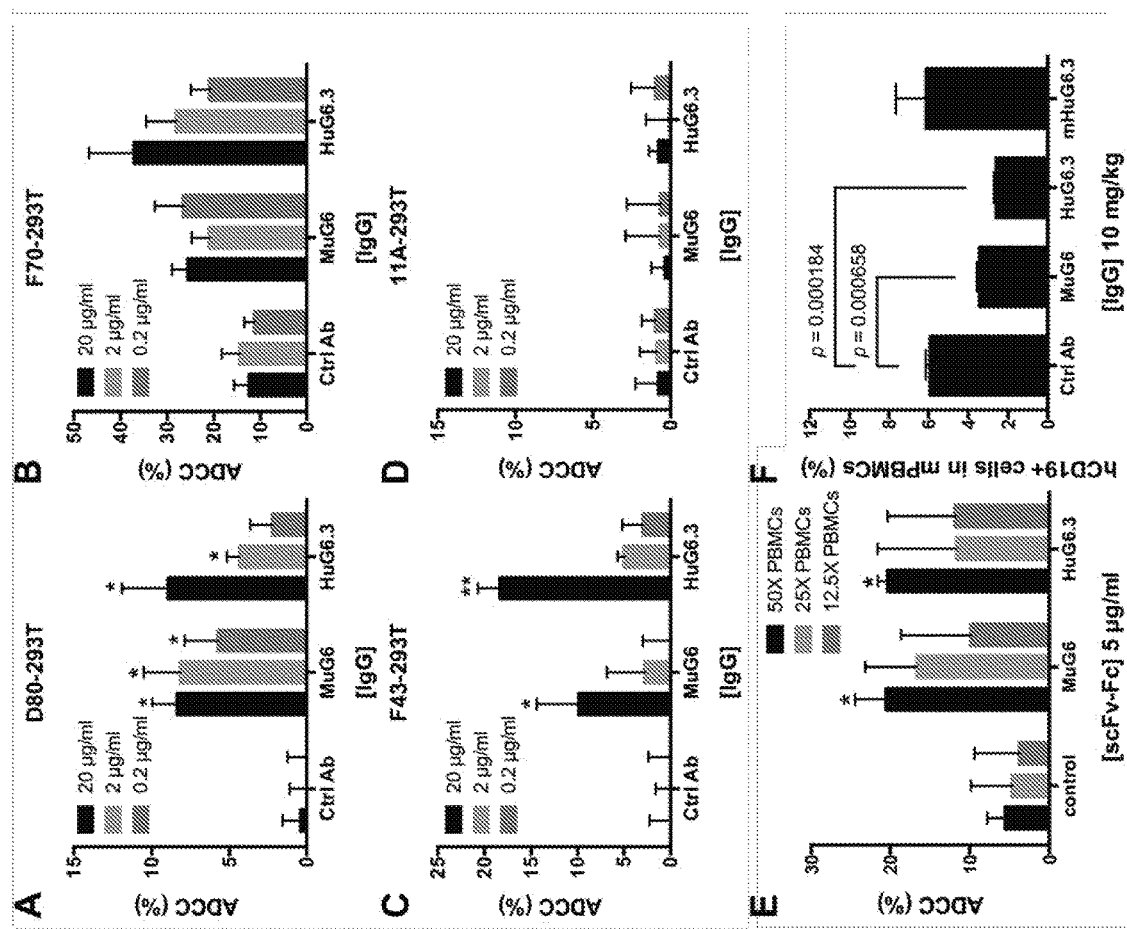
Figure 6. Mu/HuG6s mediate killing of *IGHV1-69*-expressing cells and B-CLL cells via ADCC.

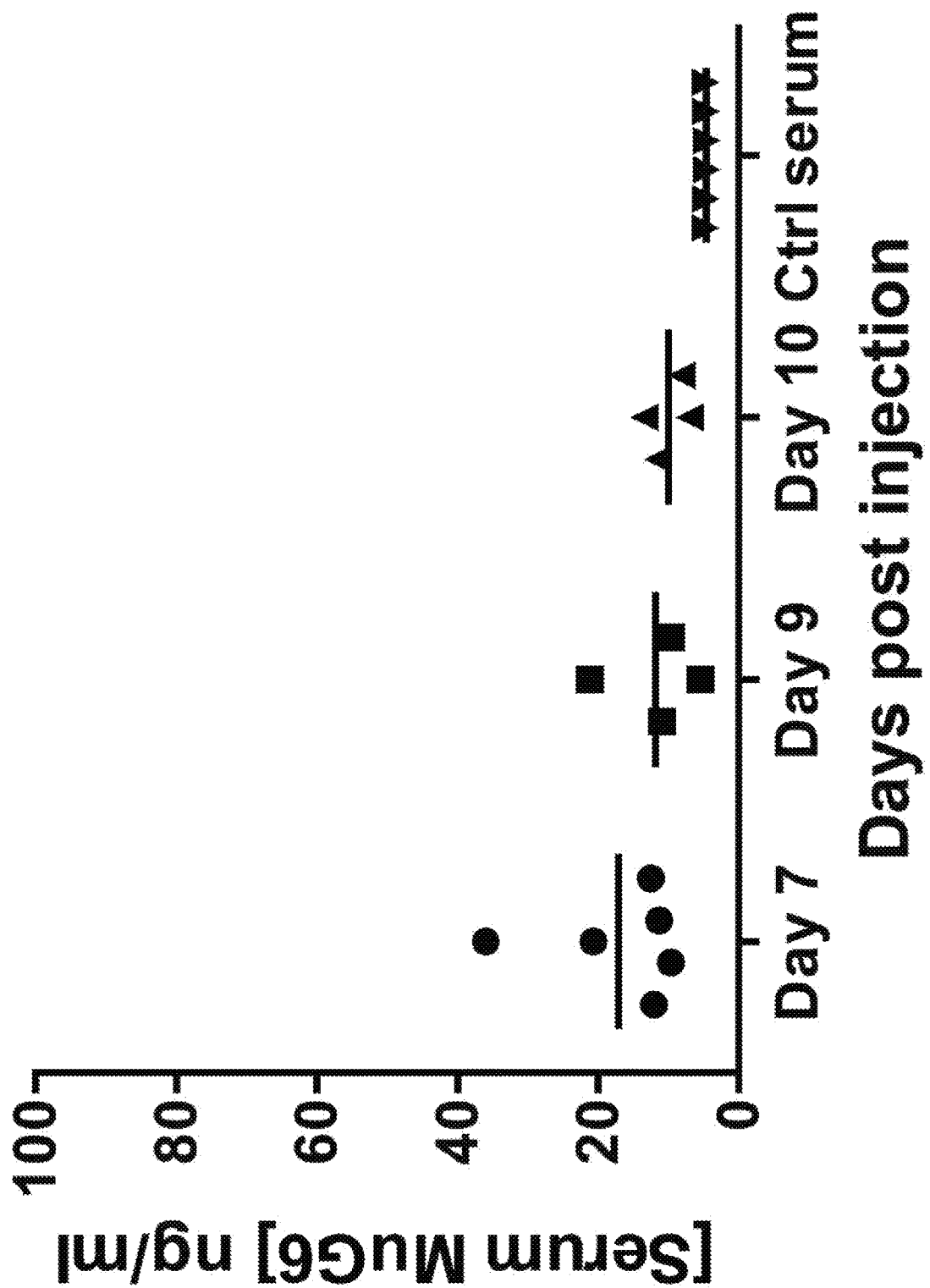
Figure 7. The MuG6 concentration in GTL mice serum.

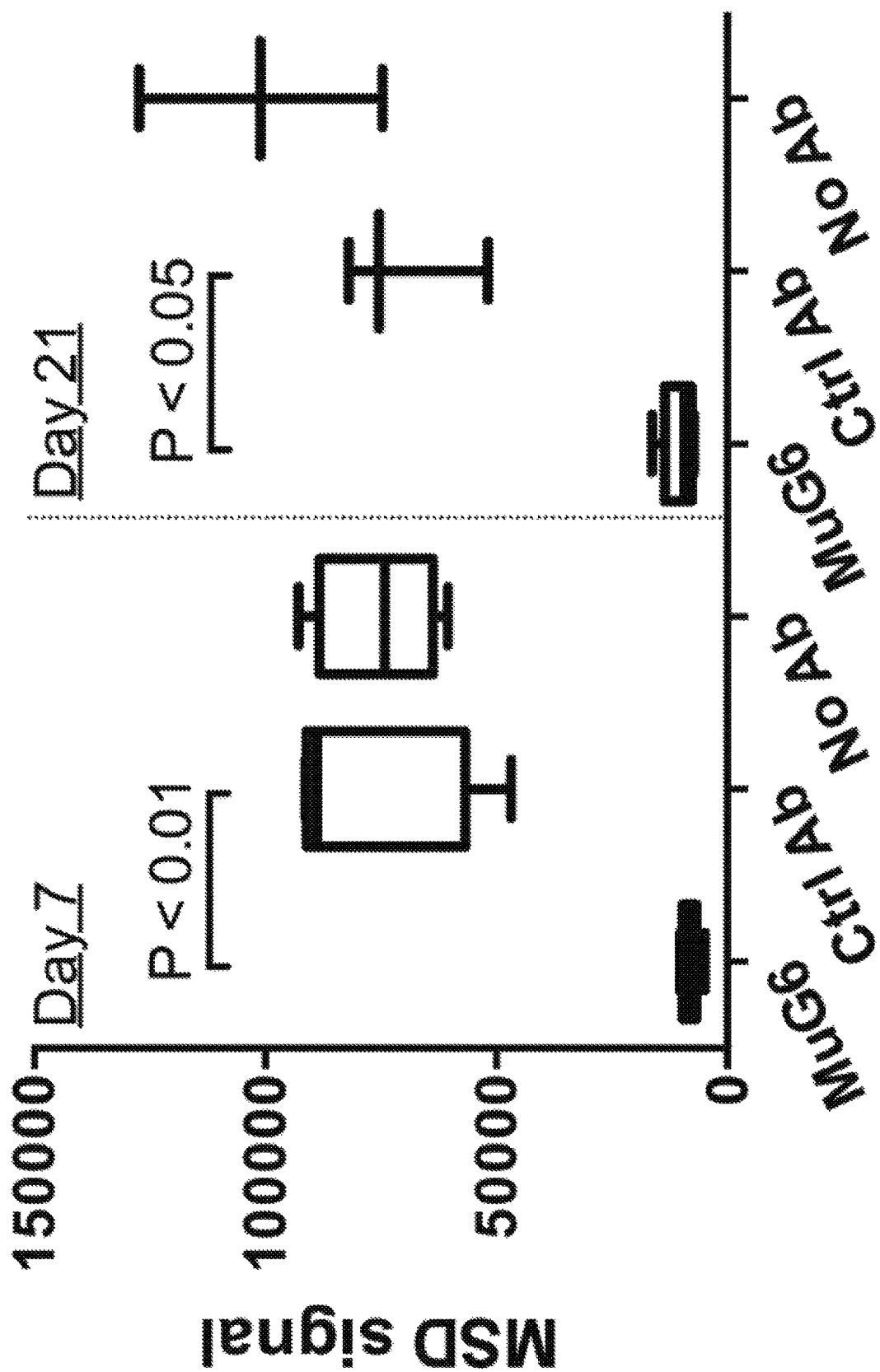
Figure 8. Antigen-specific antibody responses in humanized GTL mice using Meso Scale Discovery system.

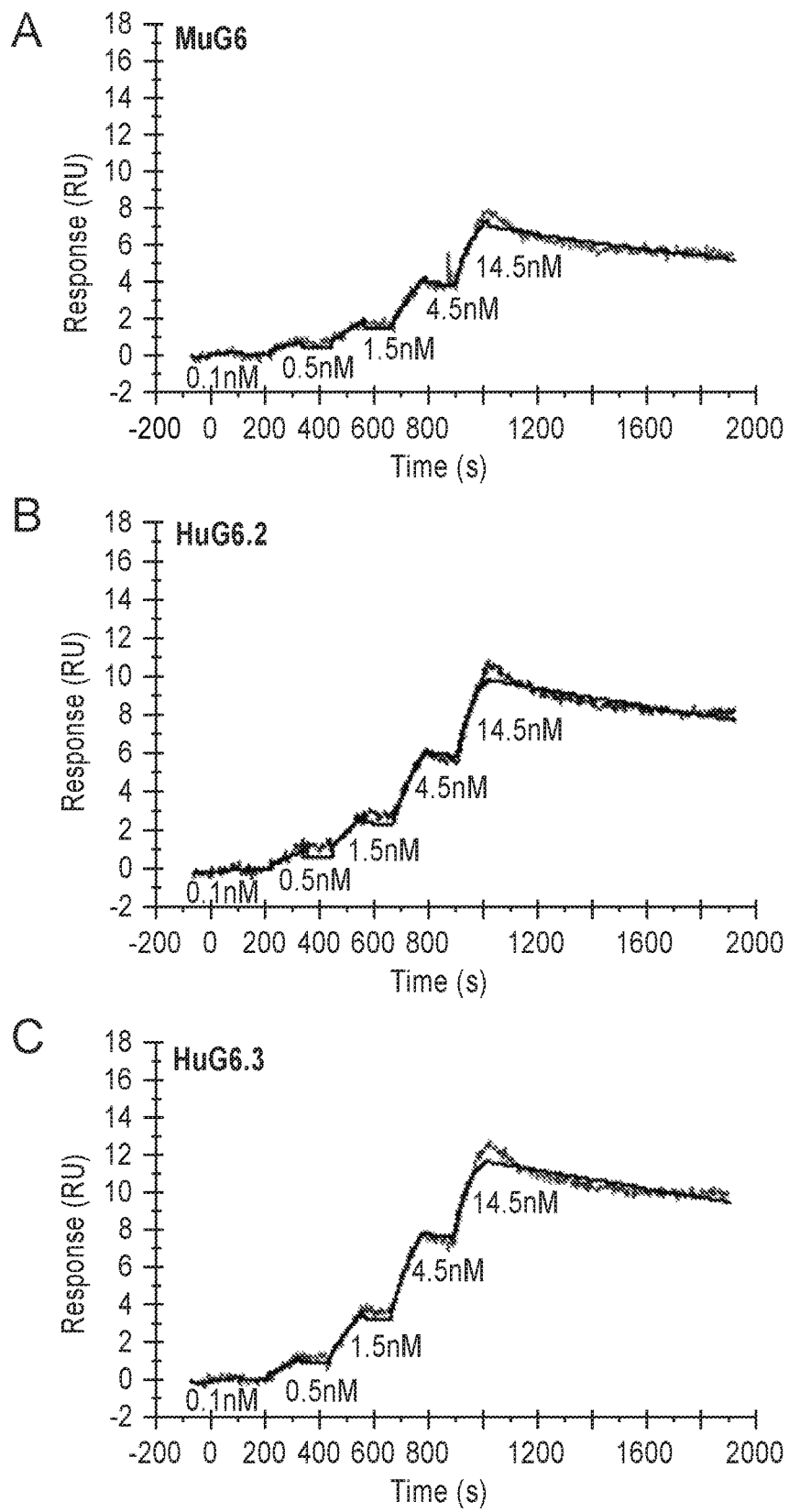
Figure 9. Characterization of the interaction of Mu/HuG6s with G6-id+ scFv using BIAcore T100

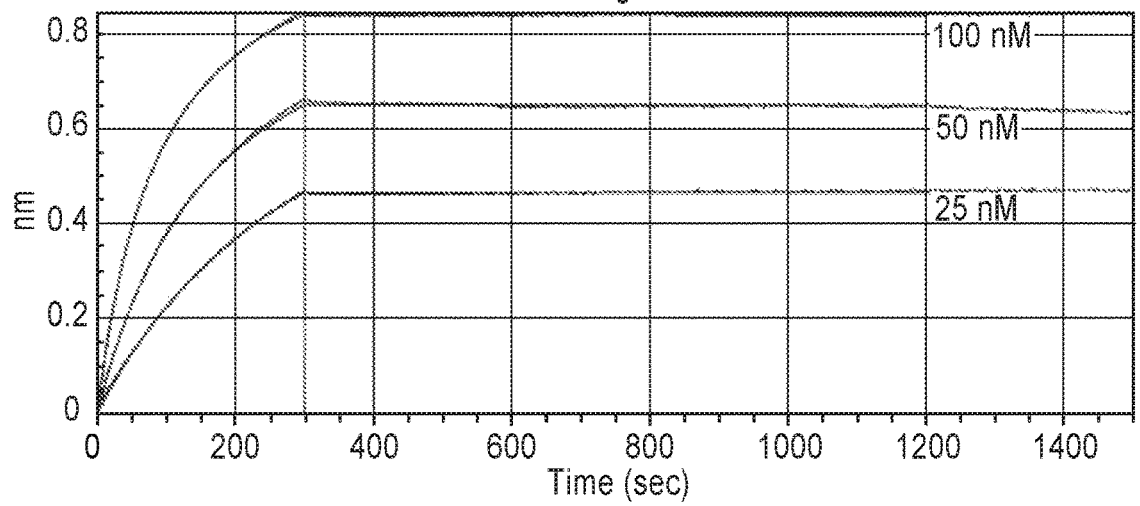
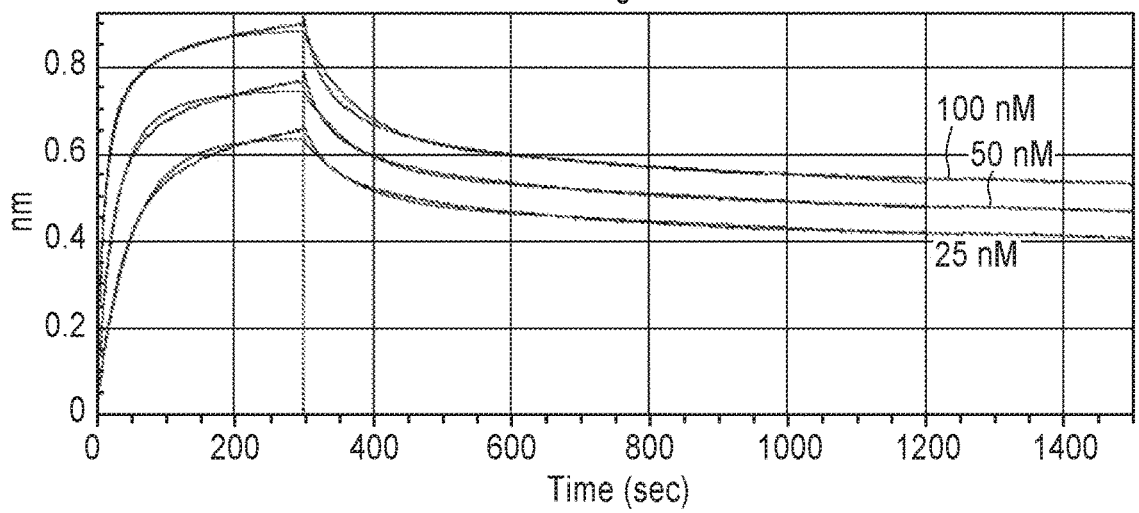
C
The kinetic values of *IGHV1-69* encoding scFv-Fcs to HuG6.3.
| | Kon (1/Ms) | Kdis (1/s) | KD (M) |
|---|---|---|---|
| D80 scFv-Fc | 8.77E+05 | 1.69E-04 | 1.93E-10 |
| F43 scFv-Fc | 2.48E+05 | 1.00E-07 | 1.00E-12 |
Figure 10. Characterization of the interaction of HuG6.3 with G6-id$^+$ IgG1s using Octet Red.

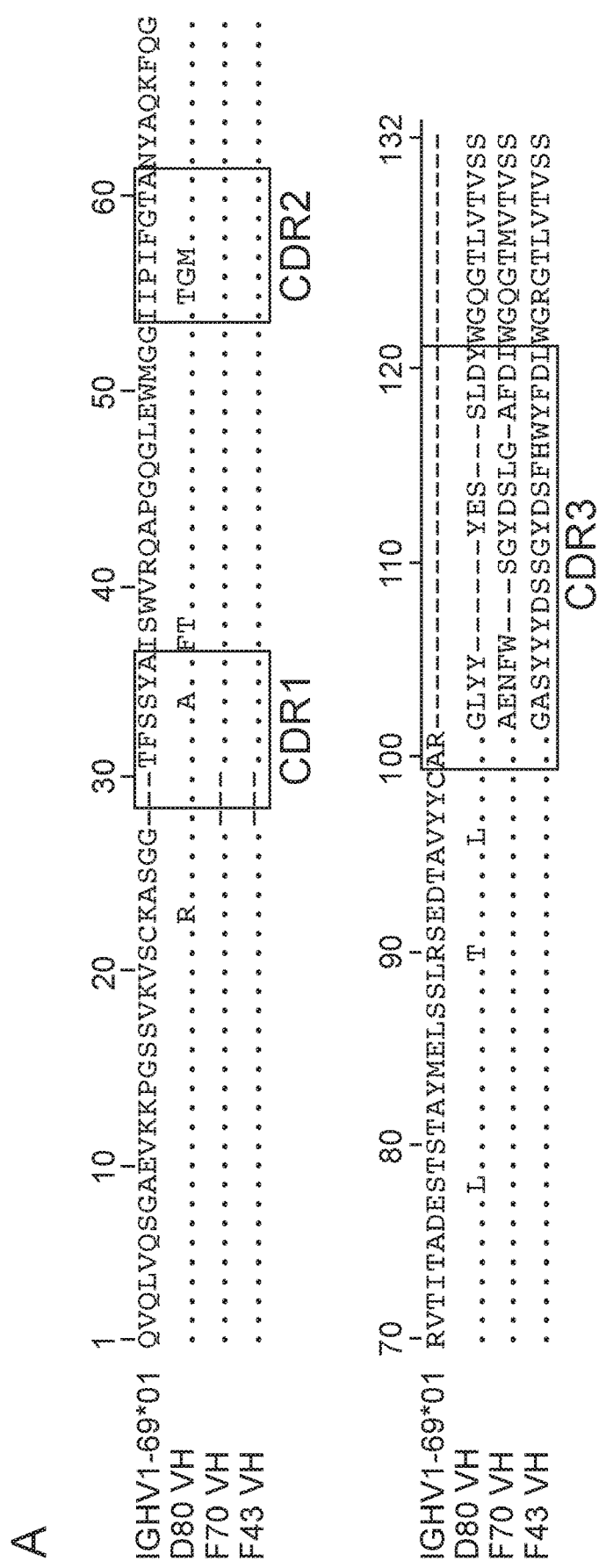
Figure 11. The construction of *IGHV1-69* encoding idiotopes and their expression.

Figure 11. The construction of *IGHV1-69* encoding idiotopes and their expression.

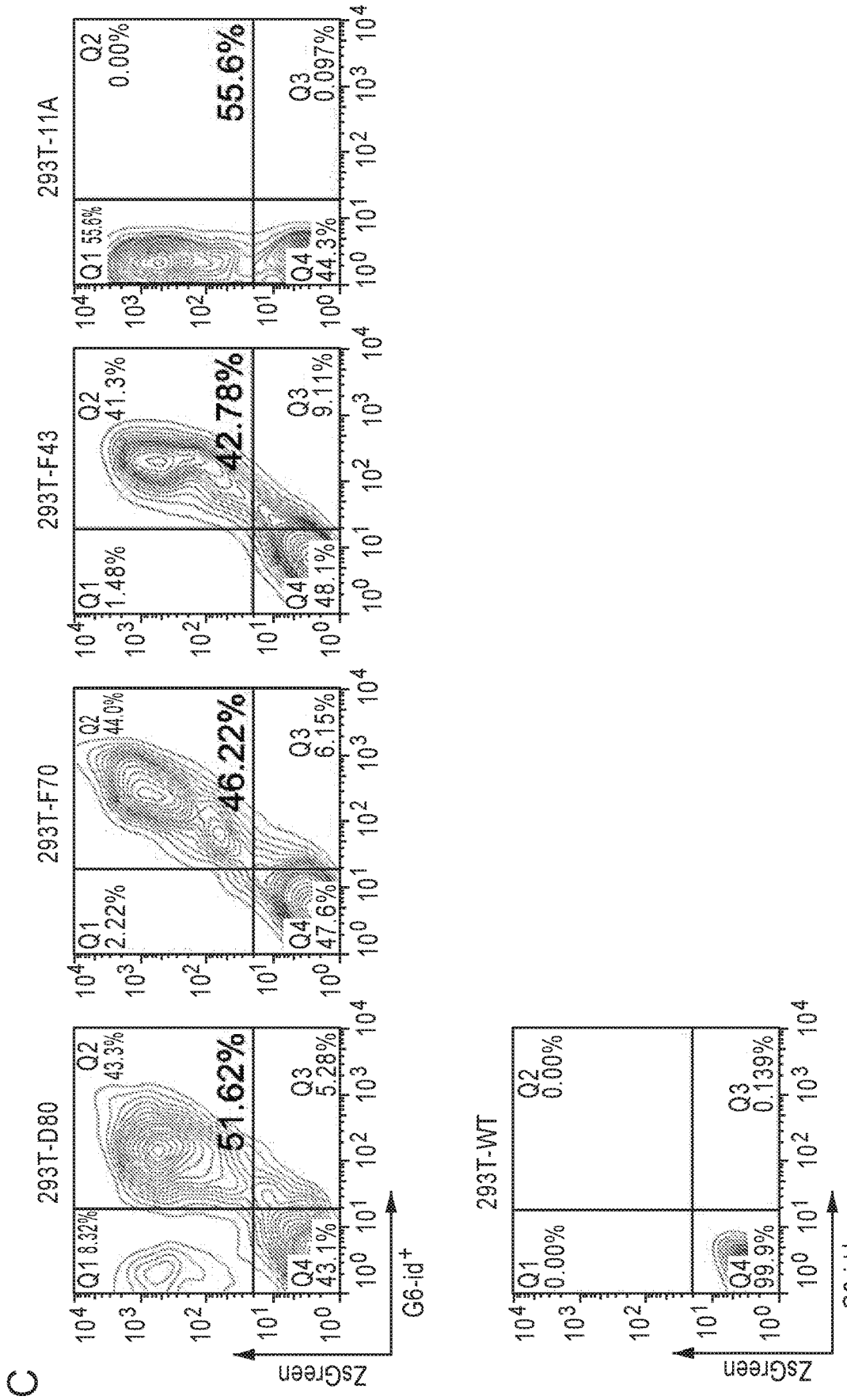
Figure 11. The construction of *IGHV1-69* encoding idiotopes and their expression.

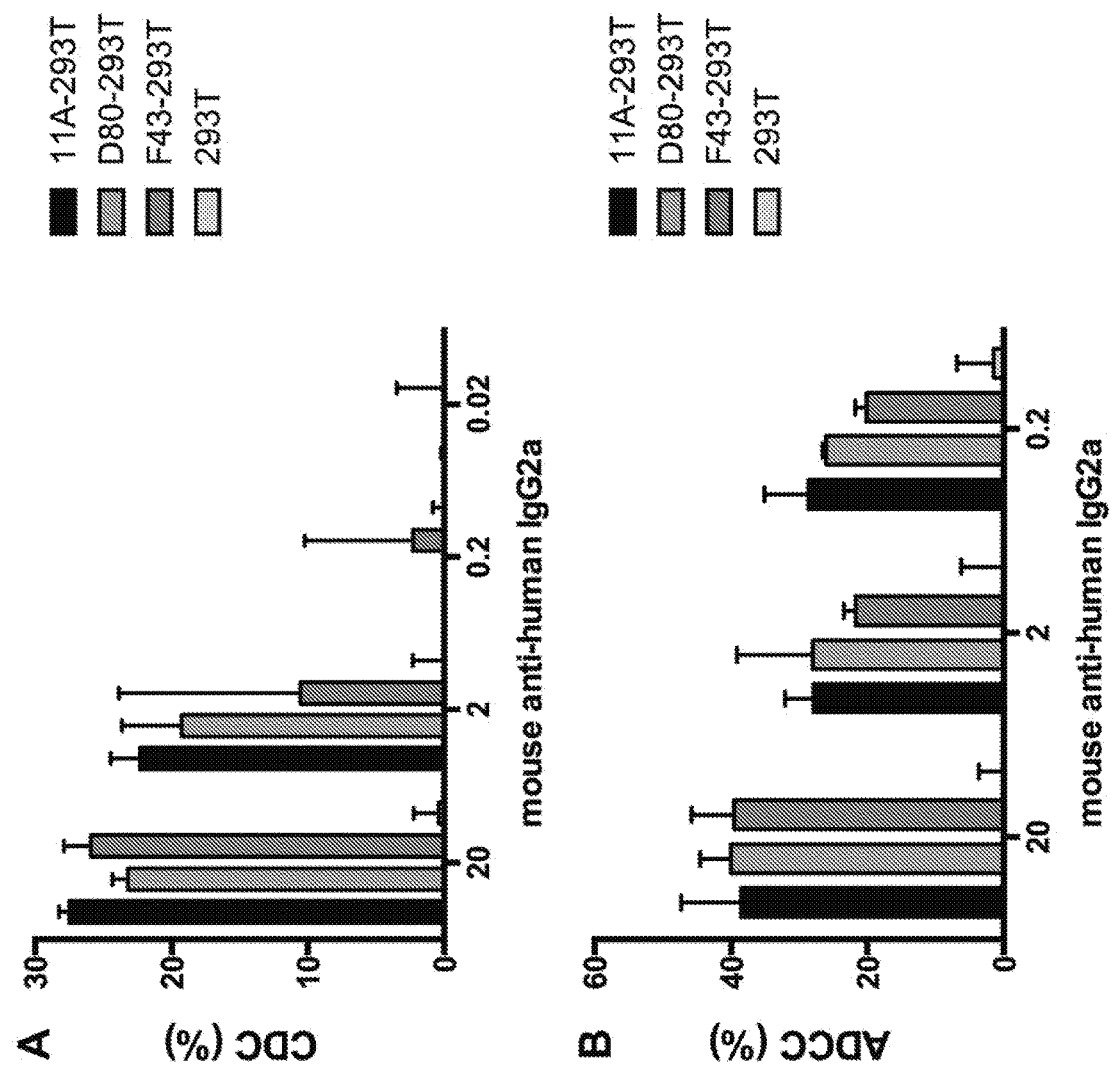
Figure 12. Control IgG mediate killing of *IGHV1-69*-expressing cells.

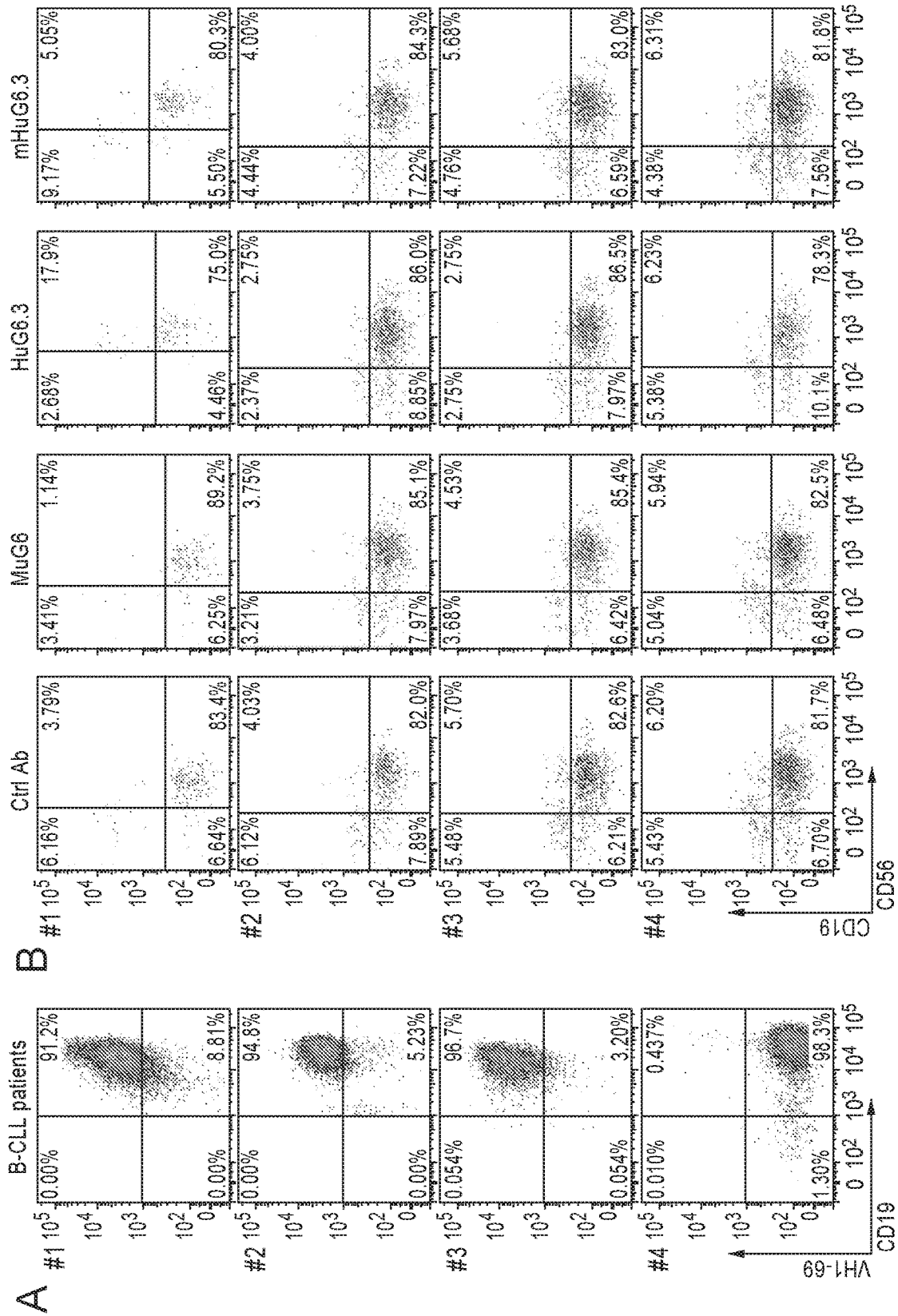
Figure 13. *In vivo* examination of MuG6 and HuG6.3 mediated depletion of B-CLL cells.

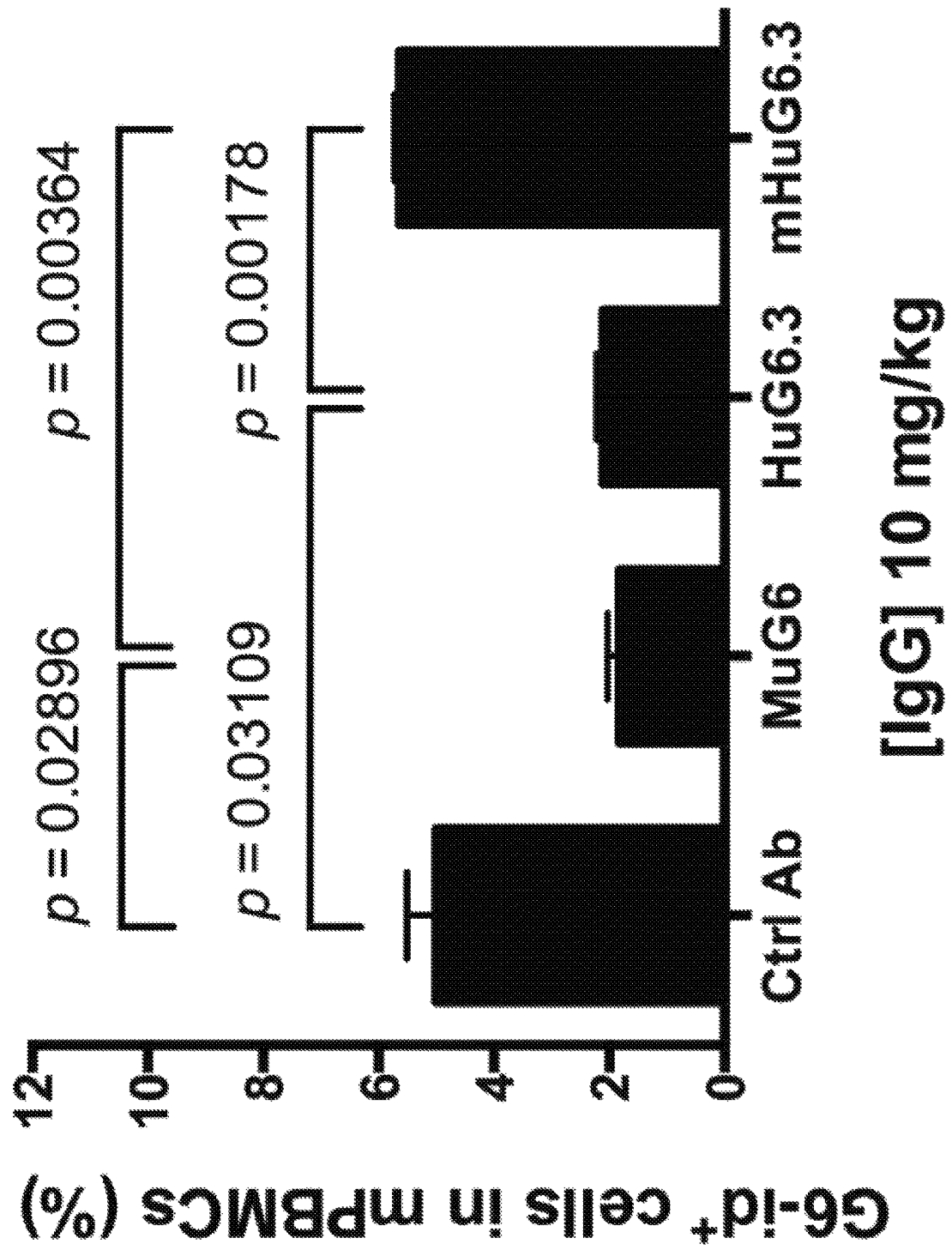
Figure 14. MuG6 and HuG6s mediate killing of IGHV1-69 B-CLL cells in vivo.

```
                         SEQUENCE LISTING

<160> NUMBER OF SEQ ID NOS: 23

<210> SEQ ID NO 1
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Gly Tyr Thr Phe Thr Ser Tyr Trp
1               5

<210> SEQ ID NO 2
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Val Ser Pro Gly Asn Ser Asp Thr
1               5

<210> SEQ ID NO 3
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Thr Arg Ser Arg Tyr Gly Asn Asn Ala Leu Asp Tyr
1               5                   10
```

<210> SEQ ID NO 4
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Gln Gly Ile Ser Ser Asn Ile Val Trp
1               5

<210> SEQ ID NO 5
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

His Gly Thr
1

<210> SEQ ID NO 6
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Val Gln Tyr Ser Gln Phe Pro Pro Thr
1               5

<210> SEQ ID NO 7
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 7
gacatccaga tgacccagag ccccagcagc ctgagcgcca gcgtgggcga cagagtgacc      60
atcacctgca gagccagcca gggcatcagc agcaacatcg tgtggtacca gcagaagccc     120
ggcaaggccc ccaagggcct gatctaccac ggcaccaacc tggagagcgg cgtgcccagc     180
agattcagcg gcagcggcag cggcaccgac tacaccctga ccatcagcag cctgcagccc     240
gaggacttcg ccacctacta ctgcgtgcag tacagccagt tcccccccac cttcggccag     300
ggcaccaagc tggagatcaa g                                                321

<210> SEQ ID NO 8
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Asp Ile Gln Met Thr Gln Ser Pro Ser Ser Leu Ser Ala Ser Val Gly
1               5                   10                  15

```
Asp Arg Val Thr Ile Thr Cys Arg Ala Ser Gln Gly Ile Ser Ser Asn
            20                  25                  30

Ile Val Trp Tyr Gln Gln Lys Pro Gly Lys Ala Pro Lys Gly Leu Ile
        35                  40                  45

Tyr His Gly Thr Asn Leu Glu Ser Gly Val Pro Ser Arg Phe Ser Gly
    50                  55                  60

Ser Gly Ser Gly Thr Asp Tyr Thr Leu Thr Ile Ser Ser Leu Gln Pro
65              70                  75                  80

Glu Asp Phe Ala Thr Tyr Tyr Cys Val Gln Tyr Ser Gln Phe Pro Pro
                85                  90                  95

Thr Phe Gly Gln Gly Thr Lys Leu Glu Ile Lys
            100                 105
```

<210> SEQ ID NO 9
<211> LENGTH: 354
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 9

```
caggtccagc tcgtccagtc cggcgctgaa gtggtgaaac ccggggcatc cgtcaaagtc     60
tcttgtaagg ctagtggcta caccttcaca tcctactgga tgcattgggt gaaacaggca    120
cctggccagg gactcgaatg gatcggagcc gtgtctcctg gaaattccga cacctcctac    180
aacgaaaaat tcaagggcaa ggcaaccctc actgtggata ctagtgcttc taccgcctac    240
atggaactct catctctccg ctctgaggac actgccgtct actactgtac tcggtcacga    300
tacgggaaca acgctctcga ttactgggga cagggcacac tggtcactgt ctct           354
```

<210> SEQ ID NO 10
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

```
Gln Val Gln Leu Val Gln Ser Gly Ala Glu Val Val Lys Pro Gly Ala
1               5                   10                  15

Ser Val Lys Val Ser Cys Lys Ala Ser Gly Tyr Thr Phe Thr Ser Tyr
            20                  25                  30

Trp Met His Trp Val Lys Gln Ala Pro Gly Gln Gly Leu Glu Trp Ile
        35                  40                  45

Gly Ala Val Ser Pro Gly Asn Ser Asp Thr Ser Tyr Asn Glu Lys Phe
    50                  55                  60

Lys Gly Lys Ala Thr Leu Thr Val Asp Thr Ser Ala Ser Thr Ala Tyr
65              70                  75                  80

Met Glu Leu Ser Ser Leu Arg Ser Glu Asp Thr Ala Val Tyr Tyr Cys
                85                  90                  95

Thr Arg Ser Arg Tyr Gly Asn Asn Ala Leu Asp Tyr Trp Gly Gln Gly
            100                 105                 110

Thr Leu Val Thr Val Ser
            115
```

<210> SEQ ID NO 11
<211> LENGTH: 321

<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 11

```
gatattcagc tcacacagag cccatcttct ctgtctgctt ctgtgggcga tcgagtgaca      60
atcacttgtc gggctagtca gggcatttct agcaacattg tgtggctcca gcagaaacct     120
ggcaaagccc caaaaggcct catctaccac ggaaccaacc tggaatctgg cgtgccatct     180
cggtttagtg gatctggatc cgggaccgat tacacactca ccatctcttc actggaacct     240
gaggatttcg ccacctacta ctgtgtccag tactcccagt ttccacccac ttttggacag     300
ggaaccaaac tcgagatcaa a                                               321
```

<210> SEQ ID NO 12
<211> LENGTH: 107
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 12

```
Asp Ile Gln Leu Thr Gln Ser Pro Ser Leu Ser Ala Ser Val Gly
1               5                   10                  15

Asp Arg Val Thr Ile Thr Cys Arg Ala Ser Gln Gly Ile Ser Ser Asn
            20                  25                  30

Ile Val Trp Leu Gln Gln Lys Pro Gly Lys Ala Pro Lys Gly Leu Ile
        35                  40                  45

Tyr His Gly Thr Asn Leu Glu Ser Gly Val Pro Ser Arg Phe Ser Gly
    50                  55                  60

Ser Gly Ser Gly Thr Asp Tyr Thr Leu Thr Ile Ser Ser Leu Glu Pro
65                  70                  75                  80

Glu Asp Phe Ala Thr Tyr Tyr Cys Val Gln Tyr Ser Gln Phe Pro Pro
                85                  90                  95

Thr Phe Gly Gln Gly Thr Lys Leu Glu Ile Lys
            100                 105
```

<210> SEQ ID NO 13
<211> LENGTH: 354
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 13

```
caggtccagc tcgtccagtc cggcgctgaa gtggtgaaac ccggggcatc cgtcaaagtc      60
tcttgtaagg ctagtggcta caccttcaca tcctactgga tgcattgggt gaaacaggca     120
cctggccagg gactcgaatg gatcggagcc gtgtctcctg gaattccgga cacctcctac     180
aacgaaaaat tcaagggcaa ggcaaccctc actgtggaca atctgcctc taccgcctac     240
atggaactct catctctccg ctctgaggat actgctgtgt actactgtac ccggtcacga     300
tacggcaata acgccctcga ttactggggg cagggaactc tggtcactgt gtct           354
```

<210> SEQ ID NO 14
<211> LENGTH: 118
<212> TYPE: PRT

```
<213> ORGANISM: Artificial Sequence
<220> FEATURE:
<223> OTHER INFORMATION: Description of Artificial Sequence: Synthetic
      polypeptide

<400> SEQUENCE: 14

Gln Val Gln Leu Val Gln Ser Gly Ala Glu Val Val Lys Pro Gly Ala
1               5                   10                  15

Ser Val Lys Val Ser Cys Lys Ala Ser Gly Tyr Thr Phe Thr Ser Tyr
            20                  25                  30

Trp Met His Trp Val Lys Gln Ala Pro Gly Gln Gly Leu Glu Trp Ile
        35                  40                  45

Gly Ala Val Ser Pro Gly Asn Ser Asp Thr Ser Tyr Asn Glu Lys Phe
    50                  55                  60

Lys Gly Lys Ala Thr Leu Thr Val Asp Lys Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Thr Arg Ser Arg Tyr Gly Asn Asn Ala Leu Asp Tyr Trp Gly Gln Gly
            100                 105                 110

Thr Leu Val Thr Val Ser
        115

<210> SEQ ID NO 15
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

Gln Val Gln Leu Gln Gln Ser Gly Thr Val Leu Ala Arg Pro Gly Ala
1               5                   10                  15

Ser Val Lys Met Ser Cys Lys Ala Ser Gly Tyr Thr Phe Thr Ser Tyr
            20                  25                  30

Trp Met His Trp Val Lys Gln Arg Pro Gly Gln Gly Leu Glu Trp Ile
        35                  40                  45

Gly Ala Val Ser Pro Gly Asn Ser Asp Thr Ser Tyr Asn Gln Lys Phe
    50                  55                  60

Lys Gly Lys Ala Thr Leu Thr Ala Val Thr Ser Thr Ser Thr Ala Tyr
65                  70                  75                  80

Met Glu Phe Ser Ser Leu Thr Asn Glu Asp Ser Ala Val Tyr Tyr Cys
                85                  90                  95

Thr Arg Ser Arg Tyr Gly Asn Asn Ala Leu Asp Tyr Trp Gly Gln Gly
            100                 105                 110

Thr Thr Val Thr Val Ser Ser
        115

<210> SEQ ID NO 16
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

Gln Val Gln Leu Val Gln Ser Gly Ala Glu Val Val Lys Pro Gly Ala
1               5                   10                  15
```

-continued

```
Ser Val Lys Val Ser Cys Lys Ala Ser Gly Tyr Thr Phe Thr Ser Tyr
            20                  25                  30

Trp Met His Trp Val Lys Gln Ala Pro Gly Gln Gly Leu Glu Trp Ile
        35                  40                  45

Gly Ala Val Ser Pro Gly Asn Ser Asp Thr Ser Tyr Asn Glu Lys Phe
    50                  55                  60

Lys Gly Lys Ala Thr Leu Thr Val Asp Lys Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Thr Arg Ser Arg Tyr Gly Asn Asn Ala Leu Asp Tyr Trp Gly Gln Gly
                100                 105                 110

Thr Leu Val Thr Val Ser Ser
        115

<210> SEQ ID NO 17
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

Gln Val Gln Leu Val Gln Ser Gly Ala Glu Val Val Lys Pro Gly Ala
1               5                   10                  15

Ser Val Lys Val Ser Cys Lys Ala Ser Gly Tyr Thr Phe Thr Ser Tyr
            20                  25                  30

Trp Met His Trp Val Lys Gln Ala Pro Gly Gln Gly Leu Glu Trp Ile
        35                  40                  45

Gly Ala Val Ser Pro Gly Asn Ser Asp Thr Ser Tyr Asn Glu Lys Phe
    50                  55                  60

Lys Gly Lys Ala Thr Leu Thr Val Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Thr Arg Ser Arg Tyr Gly Asn Asn Ala Leu Asp Tyr Trp Gly Gln Gly
                100                 105                 110

Thr Leu Val Thr Val Ser Ser
        115

<210> SEQ ID NO 18
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

Gln Val Gln Leu Val Gln Ser Gly Ala Glu Val Val Lys Pro Gly Ala
1               5                   10                  15

Ser Val Lys Val Ser Cys Lys Ala Ser Gly Tyr Thr Phe Thr Ser Tyr
            20                  25                  30

Trp Met His Trp Val Lys Gln Ala Pro Gly Gln Gly Leu Glu Trp Ile
        35                  40                  45

Gly Ala Val Ser Pro Gly Asn Ser Asp Thr Ser Tyr Asn Glu Lys Phe
    50                  55                  60
```

```
Lys Gly Lys Ala Thr Leu Thr Val Asp Lys Ser Ala Ser Thr Ala Tyr
 65                  70                  75                  80

Met Glu Leu Ser Ser Leu Arg Ser Glu Asp Thr Ala Val Tyr Tyr Cys
                 85                  90                  95

Thr Arg Ser Arg Tyr Gly Asn Asn Ala Leu Asp Tyr Trp Gly Gln Gly
            100                 105                 110

Thr Leu Val Thr Val Ser Ser
        115

<210> SEQ ID NO 19
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

Asp Ile Glu Leu Thr Gln Ser Pro Ser Ser Met Ser Val Ser Leu Gly
1               5                   10                  15

Asp Thr Val Asn Ile Thr Cys Arg Ala Ser Gln Gly Ile Ser Ser Asn
            20                  25                  30

Ile Val Trp Leu Gln Gln Lys Pro Gly Lys Ser Phe Lys Gly Leu Ile
        35                  40                  45

Tyr His Gly Thr Asn Leu Glu Asp Gly Val Pro Ser Arg Phe Ser Gly
    50                  55                  60

Ser Gly Ser Gly Ala Asp Tyr Ser Leu Thr Ile Ser Ser Leu Glu Ser
65                  70                  75                  80

Glu Asp Phe Ala Asp Tyr Tyr Cys Val Gln Tyr Ser Gln Phe Pro Pro
                85                  90                  95

Thr Phe Gly Ser Gly Thr Lys Leu Glu Leu Lys
            100                 105

<210> SEQ ID NO 20
<211> LENGTH: 98
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg

<210> SEQ ID NO 21
<211> LENGTH: 123
```

```
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (28)..(30)
<223> OTHER INFORMATION: Any amino acid

<400> SEQUENCE: 21

Gln Val Gln Leu Val Gln Ser Gly Ala Glu Val Lys Lys Pro Gly Ser
1               5                   10                  15

Ser Val Lys Val Ser Cys Arg Ala Ser Gly Gly Xaa Xaa Xaa Thr Phe
            20                  25                  30

Ser Ala Tyr Ala Phe Thr Trp Val Arg Gln Ala Pro Gly Gln Gly Leu
        35                  40                  45

Glu Trp Met Gly Gly Ile Thr Gly Met Phe Gly Thr Ala Asn Tyr Ala
    50                  55                  60

Gln Lys Phe Gln Gly Arg Val Thr Ile Thr Ala Asp Glu Leu Thr Ser
65                  70                  75                  80

Thr Ala Tyr Met Glu Leu Ser Ser Leu Thr Ser Glu Asp Thr Ala Leu
                85                  90                  95

Tyr Tyr Cys Ala Arg Gly Leu Tyr Tyr Glu Ser Ser Leu Asp Tyr
            100                 105                 110

Trp Gly Gln Gly Thr Leu Val Thr Val Ser Ser
            115                 120

<210> SEQ ID NO 22
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ala Glu Asn Phe Trp Ser Gly Tyr Asp Ser Leu Gly Ala Phe
            100                 105                 110

Asp Ile Trp Gly Gln Gly Thr Met Val Thr Val Ser Ser
        115                 120                 125

<210> SEQ ID NO 23
<211> LENGTH: 129
<212> TYPE: PRT
<213> ORGANISM: Artificial Sequence
<220> FEATURE:
<223> OTHER INFORMATION: Description of Artificial Sequence: Synthetic
      polypeptide
```

```
<400> SEQUENCE: 23

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Ala Ser Tyr Tyr Tyr Asp Ser Ser Gly Tyr Asp Ser Phe
            100                 105                 110

His Trp Tyr Phe Asp Leu Trp Gly Arg Gly Thr Leu Val Thr Val Ser
        115                 120                 125

Ser
```

COMPOSITION AND METHODS OF TREATING B CELL DISORDERS

RELATED APPLICATIONS

This application is a national stage entry of International Application PCT/US2017/050093, filed on Sep. 5, 2017, which claims benefit of, and priority to, U.S. Ser. No. 62/383,004 filed on Sep. 2, 2016 and U.S. Ser. No. 62/384,397 filed on Sep. 7, 2016 the contents of which are each hereby incorporated by reference in their entireties.

GOVERNMENT INTEREST

This invention was made with government support under grant number W911NF-10-1-0266 awarded by The Department of The Army. The government has certain rights in the invention.

SEQUENCE LISTING

The instant application contains a Sequence Listing which has been filed electronically in ASCII format and is hereby incorporated by reference in its entirety. Said ASCII copy, created on May 20, 2019, is named 5031461-039-US3_SL.txt and is 19,100 bytes in size.

FIELD OF THE INVENTION

This invention relates generally to humanized anti-human VH1-69 antibodies as well as to methods of using same to treat B cell disorders.

BACKGROUND OF THE INVENTION

B-cell chronic lymphocytic leukemia (B-CLL) is the most common leukemia in the United States, accounting for approximately 30% of all adult leukemia cases. Over 14,620 individuals develop B-CLL annually, there are circa 4,650 deaths and no curative therapies. The small molecule inhibitors, such as BTK and PI3-kinase inhibitors, and Bcl-2 family inhibitors, as well as purine nucleoside analogs (PNAs), that are used as the standard treatment for B-CLL patients have shown response rates ranging between 9 to 70%. However, treatment with such agents is invariably associated with side effects that range from mild to severe, and eventual emergence of drug resistance. In addition, immunotherapies against B-CLL, including ofatumumab (Arzerra®, anti-CD20), rituximab (Rituxan®, anti-CD20), and alemtuzumab (Campath®, anti-CD52), show a common caveat that the targeted cell surface markers are indistinctively expressed on both normal and malignant B cells or very poorly expressed on B-CLL cells. Therefore, there is an immediate need for an alternative therapy that is specific towards malignant cells in B-CLL patients.

There is a need to rapidly develop therapeutic strategies to elicit protective host's immunity, both passively and actively.

SUMMARY OF THE INVENTION

The invention features a method of selectively killing a B-cell expressing a IGHV1-69 BCR by contacting the B-cell or administering to a subject in need thereof a huG6 antibody.

The subject has a cancer, an autoimmune disorder or an inflammatory disorder. For example the subject has chronic lymphocytic leukemia of B-cell phenotype (B-CLL), thrombotic thrombocytopenic purpura (TPP), idiopathic thrombocytopenia purpura (ITP) or cryoglobulinemia.

The antibody is monovalent, bivalent, a single chain antibody, or a component of a chimeric antigen receptor.

The antibody is administered prior to, concurrently with, or subsequent to the administration of a chemotherapeutic agent.

In various aspects the antibody has a humanized heavy chain with three CDRs having an amino acid sequence GYTFTSYW (SEQ ID NO: 1); VSPGNSDT (SEQ ID NO: 2); and TRSRYGNNALDY (SEQ ID NO: 3); and a humanized light chain with three CDRs that include an amino acid sequence of QGISSNIVW (SEQ ID NO: 4); HGT (SEQ ID NO: 5); and VQYSQFPPT (SEQ ID NO: 6).

In other aspects wherein the huG6 antibody has a heavy chain variable region comprising the amino acid sequence of SEQ ID NO:14 and a light chain variable region comprising the amino acid sequence of SEQ ID NO:8; a heavy chain variable region comprising the amino acid sequence of SEQ ID NO: 10 and a light chain variable region comprising the amino acid sequence of SEQ ID NO: 11; or a heavy chain variable region comprising the amino acid sequence of SEQ ID NO: 14 and a light chain variable region comprising the amino acid sequence of SEQ ID NO:12.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description and claims.

BRIEF DESCRIPTION OF THE DRAWINGS

FIG. 1. The in vivo function of MuG6 in the humanized GTL mice model. (A) GTL mice were injected with MuG6, control mouse IgG, or the equal amount of PBS. After 7 days, mouse blood were harvested and the percentage of human B cells in the total human lymphocytes was analyzed via flow cytometry. (B) The percentage of IGHV1-69 expressing cells was measured in the total human B cells from GTL mice blood. (C) IGHV1-69 encoded human IgM and (D) IgG responses as detected by ELISA in GTL plasma samples obtained on day 7 after antibody injection. Each symbol is representative of a single GTL mouse. P value is determined by two-tailed Mann-Whitney U-test to analyze significant differences between median values of the datasets. Individual plasma samples were tested at a 1:100 dilution.

FIG. 2. Amino acid sequence alignment of the rearranged mouse and humanized variable heavy (VH) and variable light kappa (VK) domains. The complementarity determining regions (CDRs) of heavy and light chains are marked in black rectangles. There are 18 mutations in the heavy chain and 18 mutations in light chain between HuG6.1 and MuG6. One residue is changed (VH-Threonine73 to Lysine73) between HumanG6.2 and HumanG6.3. FIG. 2 discloses SEQ ID NOS 15-19, 8, 12 and 12, respectively, in order of appearance.

FIG. 3. Antibody structural homology model. (A) The 3D structure of MuG6 is generated from web antibody modeling program (WAM). Light chain, heavy chain, and CDRs are colored in green, blue, and red, respectively. (B) The energy homology model of HuG6.1 is minimized with GROMOS force field energetics (identical orientation as the MuG6 homology model). Residues with steric clashes, bad field problems, and buried side chain with no hydrogen bonds are colored in red, yellow, and orange, respectively. (C-F) The residues with steric clashes are identified in the humanized G6.1 structural homology model. (C) Lys73 (FRW-H3) steric clashed with Gly54 (CDR-H2) (left) is mutated back to Thr73 (right). (D) Met4 (FRW-L1) steric clashed with Cys88 (FRW-L3) (left) is mutated back to Leu3 (right). (E) Tyr36 (FRW-L2) has a potential non-relevant hydrogen bond with Leu100B (CDR-H3) (left) and is mutated back to Leu36 (right). (F) Gln79 (FRW-L3) is steric clashed with Arg61 (FRW-L3) (left). Arg residue is conserved across different homologous antibodies but Gln79 is not. Thus, Gln79 was back mutated to Glu79 (right).

FIG. 4. Binding affinity and kinetics of MuG6 and HuG6s. (A) Qualitative binding analysis of MuG6 and HuG6s scFv-Fc antibodies (0-10 µg/ml) to D80 IgG (2 µg/ml) through ELISA. (B) BIAcore surface plasmon resonance kinetic data for MuG6, HuG6.2, and HuG6.3 scFv-Fcs binding to immobilized D80 scFv. (C) Relative binding relationships between HuG6.3 and IGHV1-69 encoding scFvs, D80, F43 and F70, were measured by MSD.

FIG. 5. Mu/HuG6s mediate killing of IGHV1-69-expressing cells via CDC. 293T cells were transfected to express the IGHV1-69 G6-id+ idiotype, including (A) D80-293T, (B) F70-293T, and (C) F43-293T, and (D) non-IGHV1-69 encoded 11A-293T. IGHV1-69-G6-id+ expressing cells were incubated with rabbit serum and either Mu/HuG6s or a control human IgG. Percent of cell death was measured using a LDH kit. Bars represent±standard deviation. "*", $p<0.05$; "**", $p<0.01$.

FIG. 6. MuG6 and HuG6s mediate killing of IGHV1-69-expressing cells and B-CLL cells via ADCC. MuG6 and HuG6.3 induce specific ADCC activities against IGHV1-69 G6-id+ cells when compared with control antibody. Freshly isolated human PBMC cells were used as the effector cells in the ADCC assay. (A) D80-293T, (B) F70-293T, (C) F43-293T, and (D) 11A-293T (non-IGHV1-69 encoding 293T cells as negative target cells) were incubated with PBMCs at the ratio of 25 (effector (E) cells) to 1 (target (T) cells). In panel (E) IGHV1-69 G6-id+ B cell from CLL patients were used as target (T) cells and mixed with the PBMCs at an E/T ratio of 25 to 1. Antibodies over a concentration range of 0.2 to 20 µg/mL were tested. (F) Patient B-CLL cells were injected into mice treated with or without G6 antibodies for 16 hours. Mouse blood were harvested and stained with human CD19. The percentage of human CD19 as well as B-CLL cells was quantified. Graph represents data were performed in three individual experiments. mHuG6.3, a L234A and L235A mutation version of HuG6.3. Values are mean (±S.E.M.) of triplicate measurements. "*", $p<0.05$; "**", $p<0.01$.

FIG. 7. The MuG6 concentration in GTL mice serum. At 7, 9, and 10 days after antibody treatment, serum samples from control or MuG6 mAb treated mice were collected. The concentration of MuG6 in mouse serum was measured by ELISA using IGHV1-69-encoded D80 mAb (a cognate antigen that uses the 51p1 sequence with IGHV1-69 germ-line configuration) as the capture antigen. The data represent from individual mice in each group with a line at the average.

FIG. 8. Antigen-specific antibody responses in GTL mice using Meso Scale Discovery system. IGHV1-69 encoding human IgG was detected by MSD in GTL plasma samples obtained on day 7 and 21 after antibody injection. Data shown in the box and whiskers graph represent all GTL experiments and the box extends from lowest percentile to the highest percentile, with a line at the median. P value was determined by two-tailed Mann-Whitney U-test to analyze significant differences between median values of the datasets. Individual plasma samples were tested at 1:10 dilutions.

FIG. 9. Characterization of the interaction of Mu/HuG6s with G6-id+ scFv using BIAcore T100. (A) Representative double reference corrected single cycle kinetic titration (SPR) binding curves (black), monitored on a surface of covalently stabilized G6-id+ scFv, for MuG6, (B) HuG6.2, or (C) HuG6.3 scFv-Fcs at 4° C. in HBS-P buffer. In each case, a three-fold dilution series of scFv-Fcs was injected over the surface, at 30 µl/min and the apparent on- and off-rate constants were by globally fitting (red) a 1:1 kinetic binding model, with mass transport considerations, to the sensorgrams using the analysis software supplied with the instrument.

FIG. 10. Characterization of the interaction of HuG6.3 with G6-id+ IgG1s using Octet Red. The binding patterns of HuG6.3 to F43 scFv-Fc (A) and D80 scFv-Fc (B) were analyzed by an Octet-RED immunosensor. (C) The comparison of the kinetic parameter values for the HuG6.3 and IGHV1-69 encoding scFv-Fcs was performed using the Data Analysis 7.0 program. In each case, a three-fold dilution series of scFv-Fcs was incubated and the apparent on- and off-rate constants were by globally fitting (red) a 2:1 kinetic binding model, with mass transport considerations, to the sensorgrams using the analysis software supplied with the instrument.

FIG. 11. The construction of IGHV1-69 encoding idiotopes and their expression. (A) The consensus sequences of IGHV1-69 (SEQ ID NO: 20) on D80 (SEQ ID NO: 21), F70 (SEQ ID NO: 22), and F43 (SEQ ID NO: 23) are 87, 100, and 100%, respectively. (B) The construction sequence of IGHV1-69 in the expressing vector is showed in the left panel. (C) 293T cells were transfected with control or IGHV1-69 expression vectors. After 48 hours, the photos were taken in the bright field (left) and the fluorescence microscope (right). (D) The expression levels of IGHV1-69 in transfected cells were analyzed in flow cytometry.

FIG. 12. Control IgG mediate killing of IGHV1-69-expressing cells. Anti-human Fc control IgG mediated tolerant CDC and ADCC activities against IGHV1-69 encoding CLL cells. Either rabbit serum or freshly isolated human PBMC cells were used for cytotoxicity assays. (A) The CDC and (B) ADCC activities was mediated by the anti-human Fc control IgG on transfected and expressed the IGHV1-69idiotopes, including D80-293T and F43-293T, non-IGHV1-69 encoded 11A-293T and untransfected 293 T cells. Bars represent±standard deviation.

FIG. 13. In vivo examination of MuG6 and HuG6.3 mediating depletion of B-CLL cells. (A) B-CLL cells were harvested from B-CLL patients and stained by anti-CD19 and anti-VH1-69 antibodies. (B) Both G6-id+ (patient #1, 2, and 3) and G6-id− (patient #4) B-CLL cells (1×10⁶) were mixed with human nature killer cells (5×106, isolated from healthy donors) and injected into NSG mice. Mice then received 10 mg/kg control IgG1, MuG6 IgG1, HuG6.3 IgG1, or Fc-mutated HuG6.3 IgG1. After 16 hours incubation, mouse blood were harvested and mouse PBMCs were stained with anti-human CD19 and CD56 to separate the B-CLL and NK cells.

FIG. 14. MuG6 and HuG6s mediate killing of IGHV1-69 B-CLL cells in vivo. The percentage of G6-id+ B-CLL cells was quantified. Graph represents data were performed in two individual experiments from two B-CLL patients. Bars represent mean±S.D.

DETAILED DESCRIPTION

The present invention provides humanized monoclonal antibodies specific against human immunoglobulin heavy chain variable region germline gene VH1-69. In particular, the invention provides a humanized anti-human VH1-69 idiotype antibody G6 (referred to herein as huG6). Specifically, this invention is based upon the discovery that huG6 antibodies can deplete cells encoding IGHV1-69 BCRs. Since circa 6.16±0.55 of the circulating IGH repertoire from healthy individuals express IGHV1-69 BCRs, an therapeutic reagent that targets this B cell subset will not lead to global B cell depletion, and therefore offers the potential for a new precision medicine for B-cell disorders such as B-cell disorders such as chronic lymphocytic leukemia of B-cell phenotype (B-CLL), thrombotic thrombocytopenic purpura (TPP), idiopathic thrombocytopenia purpura (ITP), or cryoglobulinemia.

Accordingly, in one aspect the invention provides a method of treating any disease in which IGHV1-69 antibodies are involved in pathogenesis, for example, B-cell disorders such as chronic lymphocytic leukemia of B-cell phenotype (B-CLL), thrombotic thrombocytopenic purpura (TPP), idiopathic thrombocytopenia purpura (ITP), and cryoglobulinemia.

huG6 Antibodies

The heavy chain CDRs of the huG6 antibody have the following sequences: CDRH1: GYTFTSYW (SEQ ID NO: 1); CDRH2: VSPGNSDT (SEQ ID NO: 2); and CDRH3: TRSRYGNNALDY (SEQ ID NO: 3). The light chain CDRs of the huG6 antibody have the following sequences: CDRL1: QGISSNIVW (SEQ ID NO: 4); CDRL2: HGT (SEQ ID NO:5); and CDRL3: VQYSQFPPT (SEQ ID NO: 6). The nucleotide VH and VL sequences were optimized for mammalian codon usage.

huG6.1 $V_L$ nucleotide sequence:
(SEQ ID NO: 7)
GACATCCAGATGACCCAGAGCCCCAGCAGCCTGAGCGCCAGCGTGGGCGA

CAGAGTGACCATCACCTGCAGAGCCAGCCAGGGCATCAGCAGCAACATCG

TGTGGTACCAGCAGAAGCCCGGCAAGGCCCCCAAGGGCCTGATCTACCAC

GGCACCAACCTGGAGAGCGGCGTGCCCAGCAGATTCAGCGGCAGCGGCAG

CGGCACCGACTACACCCTGACCATCAGCAGCCTGCAGCCCGAGGACTTCG

CCACCTACTACTGCGTGCAGTACAGCCAGTTCCCCCCCACCTTCGGCCAG

GGCACCAAGCTGGAGATCAAG huG6.1 $V_L$ amino acid sequence:
(SEQ ID NO: 8)
DIQMTQSPSSLSASVGDRVTITCRASQGISSNIVWYQQKPGKAPKGLIYH

GTNLESGVPSRFSGSGSGTDYTLTISSLQPEDFATYYCVQYSQFPPTFGQ

GTKLEIK huG6.2 $V_L$ nucleotide sequence:
(SEQ ID NO: 9)
CAGGTCCAGCTCGTCCAGTCCGGCGCTGAAGTGGTGAAACCCGGGGCATC

CGTCAAAGTCTCTTGTAAGGCTAGTGGCTACACCTTCACATCCTACTGGA

TGCATTGGGTGAAACAGGCACCTGGCCAGGGACTCGAATGGATCGGAGCC

GTGTCTCCTGGAAATTCCGACACCTCCTACAACGAAAAATTCAAGGGCAA

GGCAACCCTCACTGTGGATACTAGTGCTTCTACCGCCTACATGGAACTCT

CATCTCTCCGCTCTGAGGACACTGCCGTCTACTACTGTACTCGGTCACGA

TACGGGAACAACGCTCTCGATTACTGGGGACAGGGCACACTGGTCACTGT

CTCT huG6.2 $V_H$ amino acid sequence:
(SEQ ID NO: 10)
QVQLVQSGAEVVKPGASVKVSCKASGYTFTSYWMHWVKQAPGQGLEWIGA

VSPGNSDTSYNEKFKGKATLTVDTSASTAYMELSSLRSEDTAVYYCTRSR

YGNNALDYWGQGTLVTVS huG6.2 $V_L$ and huG6.3 $V_L$ nucleotide sequence:
(SEQ ID NO: 11)
GATATTCAGCTCACACAGAGCCCATCTTCTCTGTCTGCTTCTGTGGGCGA

TCGAGTGACAATCACTTGTCGGGCTAGTCAGGGCATTTCTAGCAACATTG

TGTGGCTCCAGCAGAAACCTGGCAAAGCCCCAAAAGGCCTCATCTACCAC

GGAACCAACCTGGAATCTGGCGTGCCATCTCGGTTTAGTGGATCTGGATC

CGGGACCGATTACACACTCACCATCTCTTCACTGGAACCTGAGGATTTCG

CCACCTACTACTGTGTCCAGTACTCCCAGTTTCCACCCACTTTTGGACAG

GGAACCAAACTCGAGATCAAA huG6.2 $V_L$ and huG6.3 $V_L$ amino acid sequence:
(SEQ ID NO: 12)
DIQLTQSPSSLSASVGDRVTITCRASQGISSNIVWLQQKPGKAPKGLIYH

GTNLESGVPSRFSGSGSGTDYTLTISSLEPEDFATYYCVQYSQFPPTFGQ

GTKLEIK huG6.1 $V_H$ and huG6.3 $V_H$ nucleotide sequence:
(SEQ ID NO: 13)
CAGGTCCAGCTCGTCCAGTCCGGCGCTGAAGTGGTGAAACCCGGGGCATC

CGTCAAAGTCTCTTGTAAGGCTAGTGGCTACACCTTCACATCCTACTGGA

TGCATTGGGTGAAACAGGCACCTGGCCAGGGACTCGAATGGATCGGAGCC

GTGTCTCCTGGAAATTCCGACACCTCCTACAACGAAAAATTCAAGGGCAA

GGCAACCCTCACTGTGGACAAATCTGCCTCTACCGCCTACATGGAACTCT

CATCTCTCCGCTCTGAGGATACTGCTGTGTACTACTGTACCCGGTCACGA

TACGGCAATAACGCCCTCGATTACTGGGGGCAGGGAACTCTGGTCACTGT

GTCT huG6.1 $V_H$ and huG6.3 $V_H$ amino acid sequence:
(SEQ ID NO: 14)
QVQLVQSGAEVVKPGASVKVSCKASGYTFTSYWMHWVKQAPGQGLEWIGA

VSPGNSDTSYNEKFKGKATLTVDKSASTAYMELSSLRSEDTAVYYCTRSR

YGNNALDYWGQGTLVTVS

Methods of Treatment

The antibodies can be used to prevent, diagnose, or treat medical disorders in a subject, especially in humans. Specifically, the invention provides for both prophylactic and therapeutic methods of treating a subject at risk of (or susceptible to) of a disease A further aspect of the invention is a method of inducing cell killing of B cells in vivo, comprising contacting B cells with a huG6 antibody and/or conjugate thereof of the present invention, thereby killing the B cells. The B-cells express a IGHV1-69 BCR The invention also provides methods of treating diseases by administration of a huG6 antibody or fragment thereof and/or conjugate thereof to a mammal, such as a human patient suffering from a disease. In any of the methods for treating an autoimmune disease or a IGHV1-69 BCR expressing cancer, in one aspect, the antibody is huG6.1, huG6.2 or huG6.3. Thus, one aspect is a method of treating a IGHV1-69 BCR positive cancer, comprising administering to a patient suffering from the cancer, a therapeutically effective amount of a huG6 antibody and/or conjugate thereof of the invention. In a preferred aspect, the IGHV1-69 BCR positive cancer is B-cell chronic lymphocytic leukemia (B-CLL). In additional aspects, the treatment method further comprises administering to the patient at least one chemotherapeutic agent.

Also provided is a method of treating an autoimmune or inflammatory disease, comprising administering to a patient suffering from the autoimmune or inflammatory disease, a therapeutically effective amount of the huG6 antibody or fragment and/or conjugate thereof as discussed herein. The autoimmune or inflammatory disease is selected from the group consisting of rheumatoid arthritis, juvenile rheumatoid arthritis, systemic lupus erythematosus (SLE), Wegener's disease, inflammatory bowel disease, idiopathic thrombocytopenic purpura (ITP), thrombotic thrombocytopenic purpura (TTP), autoimmune thrombocytopenia, multiple sclerosis, psoriasis, IgA nephropathy, IgM polyneuropathies, myasthenia gravis, vasculitis, diabetes mellitus, Reynaud's syndrome, Crohn's disease, ulcerative colitis, gastritis, Hashimoto's thyroiditis, ankylosing spondylitis, hepatitis C-associated cryoglobulinemic vasculitis, chronic focal encephalitis, bullous pemphigoid, hemophilia A, membranoproliferative glomerulnephritis, adult and juvenile dermatomyositis, adult polymyositis, chronic urticaria, primary biliary cirrhosis, neuromyelitis optica, Graves' dysthyroid disease, bullous pemphigoid, membranoproliferative glonerulonephritis, Churg-Strauss syndrome, asthma, psoriatic arthritis, dermatitis, respiratory distress syndrome, meningitis, encephalitis, uveitis, eczema, atherosclerosis, leukocyte adhesion deficiency, juvenile onset diabetes, Reiter's disease, Behcet's disease, hemolytic anemia, atopic dermatitis, pemphigus vulgaris, Wegener's granulomatosis, Omenn's syndrome, chronic renal failure, acute infectious mononucleosis, HIV and herpes-associated disease, systemic sclerosis, Sjorgen's syndrome and glomerulonephritis.

In preferred embodiments the disease or disorder to be treated is chronic lymphocytic leukemia of B-cell phenotype (B-CLL), thrombotic thrombocytopenic purpura (TPP) or cryoglobulinemia.

In the treatment methods, the huG6 antibodies and/or conjugate thereof can be administered alone or in conjunction with a second therapeutic agent such as a second antibody, or a chemotherapeutic agent or an immunosuppressive agent. The second antibody or fragment and/or conjugate thereof can be one that binds CD20, CD52 or a different B cell antigen, or a NK or T cell antigen. In one aspect, the second antibody or fragment and/or conjugate thereof is a radiolabeled anti-CD20 or CD52 antibody. In other aspects, the second antibody is conjugated to a cytotoxic agent including a toxin.

The present invention includes a method of inhibiting unwanted B cells and/or abnormal cell growth or treating a proliferative disorder in a mammal (e.g., human) comprising administering to said mammal a therapeutically effective amount of the huG6 antibody and/or conjugates (and/or solvates and salts thereof) or a composition thereof, alone or in combination with a second therapeutic agent.

The antibody is huG6.1, huG6.2 or huG6.3. In some aspect the antibody includes a heavy chain variable region (SEQ ID NOS: 10 or 14), encoded by the nucleic acid sequence SEQ ID NOS: 9 or 131, and a light chain variable region (SEQ ID NO: 12 or 8) encoded by the nucleic acid sequence SEQ ID NO: 11 or 7. The heavy chain CDRs of the antibody have the following sequences: SEQ ID NOS: 1, 2 and 3. The light chain CDRs of the antibody have the following sequences: SEQ ID NOS: 4, 5 and 6. Preferably the three heavy chain CDRs include an amino acid sequence of at least 90%, 92%, 95%, 97%, 98%, 99%, or more identical to the amino acid sequence of SEQ ID NOS: 1, 2 and 3 and a light chain with three CDRs that include an amino acid sequence of at least 90%, 92%, 95%, 97%, 98%, 99%, or more identical to the amino acid sequence of SEQ ID NOS: 4, 5 and 6.

Antibodies

As used herein, the term "antibody" refers to immunoglobulin molecules and immunologically active portions of immunoglobulin (Ig) molecules, i.e., molecules that contain an antigen binding site that specifically binds (immunoreacts with) an antigen. By "specifically binds" or "immunoreacts with" is meant that the antibody reacts with one or more antigenic determinants of the desired antigen and does not react with other polypeptides. Antibodies include, but are not limited to, polyclonal, monoclonal, chimeric, dAb (domain antibody), single chain, $F_{ab}$, $F_{ab'}$ and $F_{(ab')2}$ fragments, scFvs, and $F_{ab}$ expression libraries.

A single chain Fv ("scFv") polypeptide molecule is a covalently linked $V_H$::$V_L$ heterodimer, which can be expressed from a gene fusion including $V_H$- and $V_L$-encoding genes linked by a peptide-encoding linker. (See Huston et al. (1988) Proc Nat Acad Sci USA 85(16):5879-5883). A number of methods have been described to discern chemical structures for converting the naturally aggregated, but chemically separated, light and heavy polypeptide chains from an antibody V region into an scFv molecule, which will fold into a three dimensional structure substantially similar to the structure of an antigen-binding site. See, e.g., U.S. Pat. Nos. 5,091,513; 5,132,405; and 4,946,778.

Very large naïve human scFv libraries have been and can be created to offer a large source of rearranged antibody genes against a plethora of target molecules. Smaller libraries can be constructed from individuals with infectious diseases in order to isolate disease-specific antibodies. (See Barbas et al., Proc. Natl. Acad. Sci. USA 89:9339-43 (1992); Zebedee et al., Proc. Natl. Acad. Sci. USA 89:3175-79 (1992)).

In general, antibody molecules obtained from humans relate to any of the classes IgG, IgM, IgA, IgE and IgD, which differ from one another by the nature of the heavy chain present in the molecule. Certain classes have subclasses as well, such as $IgG_1$, $IgG_2$, and others. Furthermore, in humans, the light chain may be a kappa chain or a lambda chain. The term "antigen-binding site" or "binding portion" refers to the part of the immunoglobulin molecule that participates in antigen binding. The antigen binding site is formed by amino acid residues of the N-terminal variable ("V") regions of the heavy ("H") and light ("L") chains. Three highly divergent stretches within the V regions of the heavy and light chains, referred to as "hypervariable regions," are interposed between more conserved flanking stretches known as "framework regions," or "FRs". Thus, the term "FR" refers to amino acid sequences which are naturally found between, and adjacent to, hypervariable regions in immunoglobulins. In an antibody molecule, the three hypervariable regions of a light chain and the three hypervariable regions of a heavy chain are disposed relative to each other in three dimensional space to form an antigen-binding surface. The antigen-binding surface is complementary to the three-dimensional surface of a bound antigen, and the three hypervariable regions of each of the heavy and light chains are referred to as "complementarity-determining regions," or "CDRs." Specifically, the CDRs of the antibody heavy chains are referred to as CDRH1, CDRH2 and CDRH3, respectively. Similarly, the CDRs of the antibody light chains are referred to as CDRL1, CDRL2 and CDRL3, respectively.

In some aspects, the Fc region is an isotype selected from IgM, IgA, IgG, IgE, or other isotype. Certain classes have subclasses as well, such as $IgG_1$, $IgG_2$, $IgG_3$ and $IgG_4$ and others.

In certain aspects, the antibody comprises an altered (e.g., mutated) Fc region. For example, in some aspects, the Fc region has been altered to reduce or enhance the effector functions of the antibody.

Alternatively or additionally, it may be useful to combine amino acid modifications with one or more further amino acid modifications that alter C1q binding and/or the complement dependent cytotoxicity (CDC) function of the Fc region of an antigen binding molecule. The starting polypeptide of particular interest may be one that binds to C1q and displays complement dependent cytotoxicity. Polypeptides with pre-existing C1q binding activity, optionally further having the ability to mediate CDC, may be modified such that one or both of these activities are enhanced. Amino acid modifications that alter C1q and/or modify its complement dependent cytotoxicity function are described, for example, in WO0042072, which is hereby entirely incorporated by reference.

One can design an Fc region of an antibody of the present invention with altered effector function, e.g., by modifying C1q binding and/or Fc.gamma.R binding and thereby changing CDC activity and/or ADCC activity. "Effector functions" are responsible for activating or diminishing a biological activity (e.g., in a subject). Examples of effector functions include, but are not limited to: C1q binding; complement dependent cytotoxicity (CDC); Fc receptor binding; antibody-dependent cell-mediated cytotoxicity (ADCC); phagocytosis; down regulation of cell surface receptors (e.g., B cell receptor; BCR), etc. Such effector functions may require the Fc region to be combined with a binding domain (e.g., an antibody variable domain) and can be assessed using various assays (e.g., Fc binding assays, ADCC assays, CDC assays, etc.).

For example, one can generate a variant Fc region of the engineered huG6 antibody such that the antibody dependent cell-mediated cytotoxicity (ADCC) activity of the mAb is altered. For example, the mutation is an LALA mutation in the CH2 domain.

For example, one can generate a variant Fc region of the engineered huG6 antibody with improved C1q binding and improved Fc.gamma.RIII binding (e.g., having both improved ADCC activity and improved CDC activity). Alternatively, if it is desired that effector function be reduced or ablated, a variant Fc region can be engineered with reduced CDC activity and/or reduced ADCC activity. In other aspects, only one of these activities may be increased, and, optionally, also the other activity reduced (e.g., to generate an Fc region variant with improved ADCC activity, but reduced CDC activity, and vice versa). An exemplary Fc mutant is the triple residue change, S239D, A330L, and I332D (EU numbering system) in which ADCC is enhanced and CDC activity is diminished. Non-limiting methods for designing such mutants can be found, for example, in Lazar et al. (2006, Proc. Natl. Acad. Sci. U.S.A. 103(11): 4005-4010) and Okazaki et al. (2004, J. Mol. Biol. 336(5):1239-49). See also WO 03/074679, WO 2004/029207, WO 2004/099249, WO2006/047350, WO 2006/019447, WO 2006/105338, WO 2007/041635.

Fc mutations can also be introduced in engineered antibodies to alter their interaction with the neonatal Fc receptor (FcRn) and improve their pharmacokinetic properties. A collection of human Fc variants with improved binding to the FcRn have been described and include, for example, Shields et al., 2001. High resolution mapping of the binding site on human IgG1 for Fc.gamma.RI, Fc.gamma.RII, Fc.gamma.RIII, and FcRn and design of IgG1 variants with improved binding to the Fc.gamma.R, J. Biol. Chem. 276: 6591-6604), which is hereby entirely incorporated by reference.

Optionally, the antibody or antigen binding fragment according to the invention has at least one an amino acid mutation. Typically, the mutation is in the constant region. The mutation results in an antibody that has an altered effector function. An effector function of an antibody is altered by altering, i.e., enhancing or reducing, the affinity of the antibody for an effector molecule such as an Fc receptor or a complement component. For example, the mutation results in an antibody that is capable of reducing cytokine release from a T-cell. For example, the mutation is in the heavy chain at amino acid residue 234, 235, 265, or 297 or combinations thereof. Preferably, the mutation results in an alanine residue at either position 234, 235, 265 or 297, or a glutamate residue at position 235, or a combination thereof.

Preferably, the antibody provided herein contains one or more mutations that prevent heavy chain constant region-mediated release of one or more cytokine(s) in vivo.

In some embodiments, antibodies used herein include, for example, a $L^{234} L^{235} \rightarrow A^{234} E^{235}$ mutation in the Fc region, such that cytokine release upon exposure to antibody is significantly reduced or eliminated. The $L^{234} L^{235} \rightarrow A^{234} E^{235}$ mutation in the Fc region of the antibodies provided herein reduces or eliminates cytokine release when the antibodies are exposed to human leukocytes, whereas the mutations described below maintain significant cytokine release capacity. For example, a significant reduction in cytokine release is defined by comparing the release of cytokines upon exposure to the antibody having a $L^{234} L^{235} \rightarrow A^{234} E^{235}$ mutation in the Fc region to level of cytokine release upon exposure to another antibody having one or more of the mutations described below. Other mutations in the Fc region include, for example, $L^{234} L^{235} \rightarrow A^{234} A^{235}$, $L^{235} \rightarrow E^{235}$, $N^{297} \rightarrow A^{297}$, and $D^{265} \rightarrow A^{265}$.

Another type of amino acid substitution serves to alter the glycosylation pattern of the Fc region of an antibody. Glycosylation of an Fc region is typically either N-linked or O-linked. N-linked generally refers to the attachment of the carbohydrate moiety to the side chain of an asparagine residue. The recognition sequences for enzymatic attachment of the carbohydrate moiety to the asparagine side chain peptide sequences are asparagine-X-serine and asparagine- X-threonine, where X is any amino acid except proline. Thus, the presence of either of these peptide sequences in a polypeptide creates a potential glycosylation site. O-linked glycosylation generally refers to the attachment of one of the sugars N-aceylgalactosamine, galactose, or xylose to a hydroxyamino acid, most commonly serine or threonine, although 5-hydroxyproline or 5-hydroxylysine may also be used.

The glycosylation pattern of an antibody or fragment thereof may be altered, for example, by deleting one or more glycosylation site(s) found in the polypeptide, and/or adding one or more glycosylation site(s) that are not present in the polypeptide. Removal of glycosylation sites in the Fc region of a antibody or antibody fragment is conveniently accomplished by altering the amino acid sequence such that it eliminates one or more of the above-described tripeptide sequences (for N-linked glycosylation sites). An exemplary glycosylation variant has an amino acid substitution of residue N297 to A297 (EU numbering system) of the heavy chain. The removal of an O-linked glycosylation site may also be achieved by the substitution of one or more glycosylated serine or threonine residues with any amino acid besides serine or threonine.

Where the antibody comprises an Fc region, the carbohydrate attached thereto may be altered. For example, antibodies with a mature carbohydrate structure that lacks fucose attached to an Fc region of the antibody are described in, for example, U.S. patent application Ser. No. US 2003/0157108 (Presta, L.) and US 2004/0093621 (Kyowa Hakko Kogyo Co., Ltd). Antibodies with a bisecting N-acetylglucosamine (GlcNAc) in the carbohydrate attached to an Fc region of the antibody are referenced in, for example, WO 2003/011878, Jean-Mairet et al. and U.S. Pat. No. 6,602,684, Umana et al. Antibodies with at least one galactose residue in the oligosaccharide attached to an Fc region of the antibody are reported in, for example, WO 1997/30087, Patel et al. See also, WO 1998/58964 and WO 1999/22764 (Raju, S.) concerning antibodies with altered carbohydrate attached to the Fc region thereof. See also, for example, US 2005/0123546 (Umana et al.) regarding antigen-binding molecules with modified glycosylation.

In certain aspects, a glycosylation variant comprises an Fc region, wherein a carbohydrate structure attached to the Fc region lacks fucose. Such variants have improved ADCC function. Examples of publications related to "defucosylated" or "fucose-deficient" antibodies include: US 2003/0157108; WO 2000/61739; WO 2001/29246; US 2003/0115614; US 2002/0164328; US 2004/0093621; US 2004/0132140; US 2004/0110704; US 2004/0110282; US 2004/0109865; WO 2003/085119; WO 2003/084570; WO 2005/035586; WO 2005/035778; WO2005/053742; Okazaki et al., J. Mol. Biol., 336:1239-1249 (2004); Yamane Ohnuki et al., Biotech. Bioeng., 87: 614 (2004). Non-limiting examples of cell lines producing defucosylated antibodies include Lec13 CHO cells deficient in protein fucosylation (Ripka et al. Arch. Biochem. Biophys. 249:533-545 (1986); U.S. patent application Ser. No. US 2003/0157108 AI, Presta, L; and WO 2004/056312 AI, Adams et al., especially at Example 11), knockout cell lines, such as alpha-1,6-fucosyltransferase gene, FUT8, knockout CHO cells (Yamane-Ohnuki et al., Biotech. Bioeng., 87: 614 (2004)), and through the use of fucosylation pathway inhibitors such as, for example, castanospermine in cell culture media (US Pat. Appl. No. 2009/0041765).

In certain aspects, the antibody of the present invention is expressed in cells that express beta (1,4)-N-acetylglucosaminyltransferase III (GnT III), such that GnT III adds GlcNAc to the human engineered antigen specific antibody. Methods for producing antibodies in such a fashion are provided in WO/9954342, WO/03011878, patent publication 20030003097A1, and Umana et al., Nature Biotechnology, 17:176-180, February 1999.

An idiotype is the genetically determined variation of intramolecular structures in the variable regions of immunoglobulins. T. However, idiotype variation involves the amino acid sequence and protein structure (so-called determinants) especially in the area of the antigen-binding site, also referred to as the "idiotope". The term "idiotype" designates the complete set of determinants of a variable region of an antibody molecule.

An anti-idiotype antibody may be generated with a process that uses a purified human monoclonal antibody or a human hybridoma cell line that expresses a human monoclonal antibody. For example a process for generation of an anti-idiotype antibody may involve culturing a human hybridoma cell line that secretes a human monoclonal antibody into its supernatant and purifying this antibody, for example, using affinity chromatography, ion exchange chromatography, gel filtration, or a combination thereof. This purified human monoclonal antibody may then be used to immunize a non-human mammal, such as a mouse or a rat, by means of, for instance, an intraperitoneal injection or in vitro directly on isolated B lymphocytes. B lymphocytes may then be isolated from the non-human mammal sacrificed up to four days after the last immunization, and the isolated B lymphocytes may be brought into contact with myeloma cells of same species (e.g., mouse or rat) under conditions that lead to fusion of the myeloma cells with the B lymphocytes to generate a non-human hybridoma cell. These non-human hybridoma cells can then be cultured and tested (e.g., using ELISA) for expression of idiotype Ig antibodies, e.g., IgM, IgA, or IgG antibodies, after, for example, three weeks of culturing. These Ig antibodies can be tested for specific binding to the human hybridoma cells and to various antibodies, including the human monoclonal antibody used to immunize the non-human mammal.

As used herein, the term "epitope" includes any protein determinant capable of specific binding to an immunoglobulin, an scFv, or a T-cell receptor. Epitopic determinants usually consist of chemically active surface groupings of molecules such as amino acids or sugar side chains and usually have specific three dimensional structural characteristics, as well as specific charge characteristics. For example, antibodies may be raised against N-terminal or C-terminal peptides of a polypeptide.

As used herein, the terms "immunological binding," and "immunological binding properties" refer to the non-covalent interactions of the type which occur between an immunoglobulin molecule and an antigen for which the immunoglobulin is specific. The strength, or affinity of immunological binding interactions can be expressed in terms of the dissociation constant ($K_d$) of the interaction, wherein a smaller $K_d$ represents a greater affinity. Immunological binding properties of selected polypeptides can be quantified using methods well known in the art. One such method entails measuring the rates of antigen-binding site/antigen complex formation and dissociation, wherein those rates depend on the concentrations of the complex partners, the affinity of the interaction, and geometric parameters that equally influence the rate in both directions. Thus, both the "on rate constant" ($K_{on}$) and the "off rate constant" ($K_{off}$) can be determined by calculation of the concentrations and the actual rates of association and dissociation. (See Nature 361:186-87 (1993)). The ratio of $K_{off}/K_{on}$ enables the cancellation of all parameters not related to affinity, and is equal to the dissociation constant $K_d$. (See, generally, Davies et al. (1990) Annual Rev Biochem 59:439-473). An antibody of the present invention is said to specifically bind to an epitope when the equilibrium binding constant ($K_d$) is ≤1 μM, preferably ≤100 nM, more preferably ≤10 nM, and most preferably ≤100 pM to about 1 pM, as measured by assays such as radioligand binding assays or similar assays known to those skilled in the art.

Those skilled in the art will recognize that it is possible to determine, without undue experimentation, if a human monoclonal antibody has the same specificity as a human monoclonal antibody of the invention by ascertaining whether the former prevents the latter from binding to a human immunoglobulin variable region polypeptide. If the human monoclonal antibody being tested competes with the human monoclonal antibody of the invention, as shown by a decrease in binding by the human monoclonal antibody of the invention, then it is likely that the two monoclonal antibodies bind to the same, or to a closely related, epitope.

Various procedures known within the art may be used for the production of polyclonal or monoclonal antibodies directed against a protein of the invention, or against derivatives, fragments, analogs homologs or orthologs thereof. (See, for example, Antibodies: A Laboratory Manual, Harlow E, and Lane D, 1988, Cold Spring Harbor Laboratory Press, Cold Spring Harbor, N.Y., incorporated herein by reference).

Antibodies can be purified by well-known techniques, such as affinity chromatography using protein A or protein G, which provide primarily the IgG fraction of immune serum. Subsequently, or alternatively, the specific antigen which is the target of the immunoglobulin sought, or an epitope thereof, may be immobilized on a column to purify the immune specific antibody by immunoaffinity chromatography. Purification of immunoglobulins is discussed, for example, by D. Wilkinson (The Scientist, published by The Scientist, Inc., Philadelphia Pa., Vol. 14, No. 8 (Apr. 17, 2000), pp. 25-28).

The term "monoclonal antibody" or "MAb" or "monoclonal antibody composition", as used herein, refers to a population of antibody molecules that contain only one molecular species of antibody molecule consisting of a unique light chain gene product and a unique heavy chain gene product. In particular, the complementarity determining regions (CDRs) of the monoclonal antibody are identical in all the molecules of the population. MAbs contain an antigen binding site capable of immunoreacting with a particular epitope of the antigen characterized by a unique binding affinity for it.

Monoclonal antibodies can be prepared using hybridoma methods, such as those described by Kohler and Milstein, Nature, 256:495 (1975). In a hybridoma method, a mouse, hamster, or other appropriate host animal, is typically immunized with an immunizing agent to elicit lymphocytes that produce or are capable of producing antibodies that will specifically bind to the immunizing agent. Alternatively, the lymphocytes can be immunized in vitro.

The immunizing agent will typically include the protein antigen, a fragment thereof or a fusion protein thereof. Generally, either peripheral blood lymphocytes are used if cells of human origin are desired, or spleen cells or lymph node cells are used if non-human mammalian sources are desired. The lymphocytes are then fused with an immortalized cell line using a suitable fusing agent, such as polyethylene glycol, to form a hybridoma cell (Goding, *Monoclonal Antibodies: Principles and Practice*, Academic Press, (1986) pp. 59-103). Immortalized cell lines are usually transformed mammalian cells, particularly myeloma cells of rodent, bovine and human origin. Usually, rat or mouse myeloma cell lines are employed. The hybridoma cells can be cultured in a suitable culture medium that preferably contains one or more substances that inhibit the growth or survival of the unfused, immortalized cells. For example, if the parental cells lack the enzyme hypoxanthine guanine phosphoribosyl transferase (HGPRT or HPRT), the culture medium for the hybridomas typically will include hypoxanthine, aminopterin, and thymidine ("HAT medium"), which substances prevent the growth of HGPRT-deficient cells.

Preferred immortalized cell lines are those that fuse efficiently, support stable high level expression of antibody by the selected antibody-producing cells, and are sensitive to a medium such as HAT medium. More preferred immortalized cell lines are murine myeloma lines, which can be obtained, for instance, from the Salk Institute Cell Distribution Center, San Diego, Calif. and the American Type Culture Collection, Manassas, Va. Human myeloma and mouse-human heteromyeloma cell lines also have been described for the production of human monoclonal antibodies. (See Kozbor, J. Immunol., 133:3001 (1984); Brodeur et al., Monoclonal Antibody Production Techniques and Applications, Marcel Dekker, Inc., New York, (1987) pp. 51-63)).

The culture medium in which the hybridoma cells are cultured can then be assayed for the presence of monoclonal antibodies directed against the antigen. Preferably, the binding specificity of monoclonal antibodies produced by the hybridoma cells is determined by immunoprecipitation or by an in vitro binding assay, such as radioimmunoassay (MA) or enzyme-linked immunoabsorbent assay (ELISA). Such techniques and assays are known in the art. The binding affinity of the monoclonal antibody can, for example, be determined by the Scatchard analysis of Munson and Pollard, Anal. Biochem., 107:220 (1980). Moreover, in therapeutic applications of monoclonal antibodies, it is important to identify antibodies having a high degree of specificity and a high binding affinity for the target antigen.

After the desired hybridoma cells are identified, the clones can be subcloned by limiting dilution procedures and grown by standard methods. (See Goding, *Monoclonal Antibodies: Principles and Practice*, Academic Press, (1986) pp. 59-103). Suitable culture media for this purpose include, for example, Dulbecco's Modified Eagle's Medium and RPMI-1640 medium. Alternatively, the hybridoma cells can be grown in vivo as ascites in a mammal.

The monoclonal antibodies secreted by the subclones can be isolated or purified from the culture medium or ascites fluid by conventional immunoglobulin purification procedures such as, for example, protein A-Sepharose, hydroxylapatite chromatography, gel electrophoresis, dialysis, or affinity chromatography.

Monoclonal antibodies can also be made by recombinant DNA methods, such as those described in U.S. Pat. No. 4,816,567. DNA encoding the monoclonal antibodies of the invention can be readily isolated and sequenced using conventional procedures (e.g., by using oligonucleotide probes that are capable of binding specifically to genes encoding the heavy and light chains of murine antibodies). The hybridoma cells of the invention serve as a preferred source of such DNA. Once isolated, the DNA can be placed into expression vectors, which are then transfected into host cells such as simian COS cells, Chinese hamster ovary (CHO) cells, or myeloma cells that do not otherwise produce immunoglobulin protein, to obtain the synthesis of monoclonal antibodies in the recombinant host cells. The DNA also can be modified, for example, by substituting the coding sequence for human heavy and light chain constant domains in place of the homologous murine sequences (see U.S. Pat. No. 4,816,567; Morrison, Nature 368, 812-13 (1994)) or by covalently joining to the immunoglobulin coding sequence all or part of the coding sequence for a non-immunoglobulin polypeptide. Such a non-immunoglobulin polypeptide can be substituted for the constant domains of an antibody of the invention, or can be substituted for the variable domains of one antigen-combining site of an antibody of the invention to create a chimeric bivalent antibody.

Fully human antibodies are antibody molecules in which the entire sequence of both the light chain and the heavy chain, including the CDRs, arise from human genes. Such antibodies are termed "humanized antibodies", "human antibodies", or "fully human antibodies" herein. Human monoclonal antibodies can be prepared by using trioma technique; the human B-cell hybridoma technique (see Kozbor, et al., 1983 Immunol Today 4: 72); and the EBV hybridoma technique to produce human monoclonal antibodies (see Cole, et al., 1985 In: MONOCLONAL ANTIBODIES AND CANCER THERAPY, Alan R. Liss, Inc., pp. 77-96). Human monoclonal antibodies may be utilized and may be produced by using human hybridomas (see Cote, et al., 1983. Proc Natl Acad Sci USA 80: 2026-2030) or by transforming human B-cells with Epstein Barr Virus in vitro (see Cole, et al., 1985 In: MONOCLONAL ANTIBODIES AND CANCER THERAPY, Alan R. Liss, Inc., pp. 77-96).

In addition, human antibodies can also be produced using additional techniques, including phage display libraries. (See Hoogenboom and Winter, J. Mol. Biol., 227:381 (1991); Marks et al., J. Mol. Biol., 222:581 (1991)). Similarly, human antibodies can be made by introducing human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545,807; 5,545,806; 5,569,825; 5,625,126; 5,633,425; 5,661,016, and in Marks et al., Bio/Technology 10, 779-783 (1992); Lonberg et al., Nature 368 856-859 (1994); Morrison, Nature 368, 812-13 (1994); Fishwild et al, Nature Biotechnology 14, 845-51 (1996); Neuberger, Nature Biotechnology 14, 826 (1996); and Lonberg and Huszar, Intern. Rev. Immunol. 13 65-93 (1995).

Human antibodies may additionally be produced using transgenic nonhuman animals which are modified so as to produce fully human antibodies rather than the animal's endogenous antibodies in response to challenge by an antigen. (See PCT publication WO94/02602). The endogenous genes encoding the heavy and light immunoglobulin chains in the nonhuman host have been incapacitated, and active loci encoding human heavy and light chain immunoglobulins are inserted into the host's genome. The human genes are incorporated, for example, using yeast artificial chromosomes containing the requisite human DNA segments. An animal which provides all the desired modifications is then obtained as progeny by crossbreeding intermediate transgenic animals containing fewer than the full complement of the modifications. The preferred embodiment of such a nonhuman animal is a mouse, and is termed the Xenomouse™ as disclosed in PCT publications WO 96/33735 and WO 96/34096. This animal produces B cells which secrete fully human immunoglobulins. The antibodies can be obtained directly from the animal after immunization with an immunogen of interest, as, for example, a preparation of a polyclonal antibody, or alternatively from immortalized B cells derived from the animal, such as hybridomas producing monoclonal antibodies. Additionally, the genes encoding the immunoglobulins with human variable regions can be recovered and expressed to obtain the antibodies directly, or can be further modified to obtain analogs of antibodies such as, for example, single chain FIT (scFv) molecules.

An example of a method of producing a nonhuman host, exemplified as a mouse, lacking expression of an endogenous immunoglobulin heavy chain is disclosed in U.S. Pat. No. 5,939,598. It can be obtained by a method, which includes deleting the J segment genes from at least one endogenous heavy chain locus in an embryonic stem cell to prevent rearrangement of the locus and to prevent formation of a transcript of a rearranged immunoglobulin heavy chain locus, the deletion being effected by a targeting vector containing a gene encoding a selectable marker; and producing from the embryonic stem cell a transgenic mouse whose somatic and germ cells contain the gene encoding the selectable marker.

One method for producing an antibody of interest, such as a human antibody, is disclosed in U.S. Pat. No. 5,916,771. This method includes introducing an expression vector that contains a nucleotide sequence encoding a heavy chain into one mammalian host cell in culture, introducing an expression vector containing a nucleotide sequence encoding a light chain into another mammalian host cell, and fusing the two cells to form a hybrid cell. The hybrid cell expresses an antibody containing the heavy chain and the light chain.

In a further improvement on this procedure, a method for identifying a clinically relevant epitope on an immunogen, and a correlative method for selecting an antibody that binds immunospecifically to the relevant epitope with high affinity, are disclosed in PCT publication WO 99/53049.

The antibody can be expressed by a vector containing a DNA segment encoding the single chain antibody described above.

These can include vectors, liposomes, naked DNA, adjuvant-assisted DNA, gene gun, catheters, etc. Vectors include chemical conjugates such as described in WO 93/64701, which has targeting moiety (e.g. a ligand to a cellular surface receptor), and a nucleic acid binding moiety (e.g. polylysine), viral vector (e.g. a DNA or RNA viral vector), fusion proteins such as described in PCT/US 95/02140 (WO 95/22618) which is a fusion protein containing a target moiety (e.g. an antibody specific for a target cell) and a nucleic acid binding moiety (e.g. a protamine), plasmids, phage, etc. The vectors can be chromosomal, non-chromosomal or synthetic.

Preferred vectors include viral vectors, fusion proteins and chemical conjugates. Retroviral vectors include moloney murine leukemia viruses. DNA viral vectors are preferred. These vectors include pox vectors such as orthopox or avipox vectors, herpesvirus vectors such as a herpes simplex I virus (HSV) vector (see Geller, A. I. et al., J. Neurochem, 64:487 (1995); Lim, F., et al., in DNA Cloning: Mammalian Systems, D. Glover, Ed. (Oxford Univ. Press, Oxford England) (1995); Geller, A. I. et al., Proc Natl. Acad. Sci.: U.S.A. 90:7603 (1993); Geller, A. I., et al., Proc Natl. Acad. Sci USA 87:1149 (1990), Adenovirus Vectors (see LeGal LaSalle et al., Science, 259:988 (1993); Davidson, et al., Nat. Genet 3:219 (1993); Yang, et al., J. Virol. 69:2004 (1995) and Adeno-associated Virus Vectors (see Kaplitt, M. G. et al., Nat. Genet. 8:148 (1994).

Pox viral vectors introduce the gene into the cells cytoplasm. Avipox virus vectors result in only a short term expression of the nucleic acid. Adenovirus vectors, adeno-associated virus vectors and herpes simplex virus (HSV) vectors are preferred for introducing the nucleic acid into neural cells. The adenovirus vector results in a shorter term expression (about 2 months) than adeno-associated virus (about 4 months), which in turn is shorter than HSV vectors. The particular vector chosen will depend upon the target cell and the condition being treated. The introduction can be by standard techniques, e.g. infection, transfection, transduction or transformation. Examples of modes of gene transfer include e.g., naked DNA, $CaPO_4$ precipitation, DEAE dextran, electroporation, protoplast fusion, lipofection, cell microinjection, and viral vectors.

The vector can be employed to target essentially any desired target cell. For example, stereotaxic injection can be used to direct the vectors (e.g. adenovirus, HSV) to a desired location. Additionally, the particles can be delivered by intracerebroventricular (icv) infusion using a minipump infusion system, such as a SynchroMed Infusion System. A method based on bulk flow, termed convection, has also proven effective at delivering large molecules to extended areas of the brain and may be useful in delivering the vector to the target cell. (See Bobo et al., Proc. Natl. Acad. Sci. USA 91:2076-2080 (1994); Morrison et al., Am. J. Physiol. 266:292-305 (1994)). Other methods that can be used include catheters, intravenous, parenteral, intraperitoneal and subcutaneous injection, and oral or other known routes of administration.

Techniques can be adapted for the production of single-chain antibodies specific to an antigenic protein of the invention (see e.g., U.S. Pat. No. 4,946,778). In addition, methods can be adapted for the construction of $F_{ab}$ expression libraries (see e.g., Huse, et al., 1989 Science 246: 1275-1281) to allow rapid and effective identification of monoclonal $F_{ab}$ fragments with the desired specificity for a protein or derivatives, fragments, analogs or homologs thereof. Antibody fragments that contain the idiotypes to a protein antigen may be produced by techniques known in the art including, but not limited to: (i) an F(ab')2 fragment produced by pepsin digestion of an antibody molecule; (ii) an $F_{ab}$ fragment generated by reducing the disulfide bridges of an F(ab')2 fragment; (iii) an $F_{ab}$ fragment generated by the treatment of the antibody molecule with papain and a reducing agent and (iv) $F_v$ fragments.

Heteroconjugate antibodies are also within the scope of the present invention. Heteroconjugate antibodies are composed of two covalently joined antibodies. Such antibodies have, for example, been proposed to target immune system cells to unwanted cells (see U.S. Pat. No. 4,676,980), and for treatment of HIV infection (see WO 91/00360; WO 92/200373; EP 03089). It is contemplated that the antibodies can be prepared in vitro using known methods in synthetic protein chemistry, including those involving crosslinking agents. For example, immunotoxins can be constructed using a disulfide exchange reaction or by forming a thioether bond. Examples of suitable reagents for this purpose include iminothiolate and methyl-4-mercaptobutyrimidate and those disclosed, for example, in U.S. Pat. No. 4,676,980.

It can be desirable to modify the antibody of the invention with respect to effector function, so as to enhance, e.g., the effectiveness of the antibody in treating cancer. For example, cysteine residue(s) can be introduced into the Fc region, thereby allowing interchain disulfide bond formation in this region. The homodimeric antibody thus generated can have improved internalization capability and/or increased complement-mediated cell killing and antibody-dependent cellular cytotoxicity (ADCC). (See Caron et al., J. Exp Med., 176: 1191-1195 (1992) and Shopes, J. Immunol., 148: 2918-2922 (1992)). Alternatively, an antibody can be engineered that has dual Fc regions and can thereby have enhanced complement lysis and ADCC capabilities. (See Stevenson et al., Anti-Cancer Drug Design, 3: 219-230 (1989)).

The invention also pertains to immunoconjugates comprising an antibody conjugated to a cytotoxic agent such as a toxin (e.g., an enzymatically active toxin of bacterial, fungal, plant, or animal origin, or fragments thereof), or a radioactive isotope (i.e., a radioconjugate).

Enzymatically active toxins and fragments thereof that can be used include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *Momordica charantia* inhibitor, curcin, crotin, *Sapaonaria officinalis* inhibitor, gelonin, mitogellin, restrictocin, phenomycin, enomycin, and the tricothecenes. A variety of radionuclides are available for the production of radioconjugated antibodies. Examples include $^{212}Bi$, $^{131}I$, $^{131}In$, $^{90}Y$, and $^{186}Re$.

Conjugates of the antibody and cytotoxic agent are made using a variety of bifunctional protein-coupling agents such as N-succinimidyl-3-(2-pyridyldithiol) propionate (SPDP), iminothiolane (IT), bifunctional derivatives of imidoesters (such as dimethyl adipimidate HCL), active esters (such as disuccinimidyl suberate), aldehydes (such as glutareldehyde), bis-azido compounds (such as bis (p-azidobenzoyl) hexanediamine), bis-diazonium derivatives (such as bis-(p-diazoniumbenzoyl)-ethylenediamine), diisocyanates (such as tolyene 2,6-diisocyanate), and bis-active fluorine compounds (such as 1,5-difluoro-2,4-dinitrobenzene). For example, a ricin immunotoxin can be prepared as described in Vitetta et al., Science 238: 1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. (See WO94/11026).

Those of ordinary skill in the art will recognize that a large variety of possible moieties can be coupled to the resultant antibodies or to other molecules of the invention. (See, for example, "Conjugate Vaccines", Contributions to Microbiology and Immunology, J. M. Cruse and R. E. Lewis, Jr (eds), Carger Press, New York, (1989), the entire contents of which are incorporated herein by reference).

Coupling may be accomplished by any chemical reaction that will bind the two molecules so long as the antibody and the other moiety retain their respective activities. This linkage can include many chemical mechanisms, for instance covalent binding, affinity binding, intercalation, coordinate binding and complexation. The preferred binding is, however, covalent binding. Covalent binding can be achieved either by direct condensation of existing side chains or by the incorporation of external bridging molecules. Many bivalent or polyvalent linking agents are useful in coupling protein molecules, such as the antibodies of the present invention, to other molecules. For example, representative coupling agents can include organic compounds such as thioesters, carbodiimides, succinimide esters, diisocyanates, glutaraldehyde, diazobenzenes and hexamethylene diamines. This listing is not intended to be exhaustive of the various classes of coupling agents known in the art but, rather, is exemplary of the more common coupling agents. (See Killen and Lindstrom, Jour. Immun. 133:1335-2549 (1984); Jansen et al., Immunological Reviews 62:185-216 (1982); and Vitetta et al., Science 238:1098 (1987)). Preferred linkers are described in the literature. (See, for example, Ramakrishnan, S. et al., Cancer Res. 44:201-208 (1984) describing use of MBS (M-maleimidobenzoyl-N-hydroxysuccinimide ester). See also, U.S. Pat. No. 5,030,719, describing use of halogenated acetyl hydrazide derivative coupled to an antibody by way of an oligopeptide linker. Particularly preferred linkers include: (i) EDC (1-ethyl-3-(3-dimethylamino-propyl) carbodiimide hydrochloride; (ii) SMPT (4-succinimidyloxycarbonyl-alpha-methyl-alpha-(2-pridyl-dithio)-toluene (Pierce Chem. Co., Cat. (21558G); (iii) SPDP (succinimidyl-6 [3-(2-pyridyldithio) propionamido]hexanoate (Pierce Chem. Co., Cat #21651G); (iv) Sulfo-LC-SPDP (sulfosuccinimidyl 6 [3-(2-pyridyldithio)-propianamide] hexanoate (Pierce Chem. Co. Cat. #2165-G); and (v) sulfo-NHS (N-hydroxysulfo-succinimide: Pierce Chem. Co., Cat. #24510) conjugated to EDC.

The linkers described above contain components that have different attributes, thus leading to conjugates with differing physio-chemical properties. For example, sulfo-NHS esters of alkyl carboxylates are more stable than sulfo-NHS esters of aromatic carboxylates. NETS-ester containing linkers are less soluble than sulfo-NHS esters. Further, the linker SMPT contains a sterically hindered disulfide bond, and can form conjugates with increased stability. Disulfide linkages, are in general, less stable than other linkages because the disulfide linkage is cleaved in vitro, resulting in less conjugate available. Sulfo-NHS, in particular, can enhance the stability of carbodimide couplings. Carbodimide couplings (such as EDC) when used in conjunction with sulfo-NHS, forms esters that are more resistant to hydrolysis than the carbodimide coupling reaction alone.

The antibodies disclosed herein can also be formulated as immunoliposomes. Liposomes containing the antibody are prepared by methods known in the art, such as described in Epstein et al., Proc. Natl. Acad. Sci. USA, 82: 3688 (1985); Hwang et al., Proc. Natl Acad. Sci. USA, 77: 4030 (1980); and U.S. Pat. Nos. 4,485,045 and 4,544,545. Liposomes with enhanced circulation time are disclosed in U.S. Pat. No. 5,013,556.

Particularly useful liposomes can be generated by the reverse-phase evaporation method with a lipid composition comprising phosphatidylcholine, cholesterol, and PEG-derivatized phosphatidylethanolamine (PEG-PE). Liposomes are extruded through filters of defined pore size to yield liposomes with the desired diameter. Fab' fragments of the antibody of the present invention can be conjugated to the liposomes as described in Martin et al., J. Biol. Chem., 257: 286-288 (1982) via a disulfide-interchange reaction.

Pharmaceutical Compositions

The antibodies or agents of the invention (also referred to herein as "active compounds"), and derivatives, fragments, analogs and homologs thereof, can be incorporated into pharmaceutical compositions suitable for administration. Such compositions typically comprise the antibody or agent and a pharmaceutically acceptable carrier. As used herein, the term "pharmaceutically acceptable carrier" is intended to include any and all solvents, dispersion media, coatings, antibacterial and antifungal agents, isotonic and absorption delaying agents, and the like, compatible with pharmaceutical administration. Suitable carriers are described in the most recent edition of Remington's Pharmaceutical Sciences, a standard reference text in the field, which is incorporated herein by reference. Preferred examples of such carriers or diluents include, but are not limited to, water, saline, ringer's solutions, dextrose solution, and 5% human serum albumin. Liposomes and non-aqueous vehicles such as fixed oils may also be used. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

A pharmaceutical composition of the invention is formulated to be compatible with its intended route of administration. Examples of routes of administration include parenteral, e.g., intravenous, intradermal, subcutaneous, oral (e.g., inhalation), transdermal (i.e., topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfate; chelating agents such as ethylenediaminetetraacetic acid (EDTA); buffers such as acetates, citrates or phosphates, and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringeability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

The pharmaceutical compositions can be included in a container, pack, or dispenser together with instructions for administration.

The invention further pertains to novel agents identified by any of the aforementioned screening assays and uses thereof for treatments as described herein.

Definitions

The term "conjugate" as used herein refers to a compound or a derivative thereof that is linked to a cell binding agent (i.e., an huG6 antibody or fragment thereof) and is defined by a generic formula: C-L-CBA, wherein C=compound, L=linker, and CBA=cell binding agent or anti-CD20 antibody or fragment. In some embodiments, the generic formula: D-L-CBA, wherein D=drug, L=linker and CBA=cell binding agent or huG6 antibody or fragment, may also be used in the same manner.

A linker is any chemical moiety that is capable of linking a compound, usually a drug, such as a maytansinoid, to a cell-binding agent such as an huG6 antibody or a fragment thereof in a stable, covalent manner. Linkers can be susceptible to or be substantially resistant to acid-induced cleavage, light-induced cleavage, peptidase-induced cleavage, esterase-induced cleavage, and disulfide bond cleavage, at conditions under which the compound or the antibody remains active. Suitable linkers are well known in the art and include, for example, disulfide groups, thioether groups, acid labile groups, photolabile groups, peptidase labile groups and esterase labile groups. Linkers also include charged linkers, and hydrophilic forms thereof as described herein and know in the art.

"Abnormal cell growth", as used herein, unless otherwise indicated, refers to cell growth that is independent of normal regulatory mechanisms (e.g., loss of contact inhibition). This includes, for example, the abnormal growth of: (1) tumor cells (tumors) that proliferate by expressing a mutated tyrosine kinase or overexpression of a receptor tyrosine kinase; (2) benign and malignant cells of other proliferative diseases in which aberrant tyrosine kinase activation occurs; (3) any tumors that proliferate by receptor tyrosine kinases; (4) any tumors that proliferate by aberrant serine/threonine kinase activation; and (5) benign and malignant cells of other proliferative diseases in which aberrant serine/threonine kinase activation occurs.

The present invention can be used to treat and/or prevent a variety of diseases involving cells expressing IGHV1-69 encoded BCRs including tumorigenic diseases and immune diseases, e.g., autoimmune or inflammatory diseases.

The terms "cancer" and "cancerous" refer to or describe the physiological condition in mammals that is typically characterized by unregulated cell growth. A "tumor" comprises one or more cancerous cells. Examples of cancer include, but are not limited to, carcinoma, lymphoma, blastoma, sarcoma, and leukemia or lymphoid malignancies. Examples of "tumorigenic" diseases which can be treated and/or prevented include B cell lymphomas including NHL, precursor B cell lymphoblastic leukemia/lymphoma and mature B cell neoplasms, such as B cell chronic lymphocytic leukemia (CLL)/small lymphocytic lymphoma (SLL), B cell prolymphocytic leukemia, lymphoplasmacytic lymphoma, mantle cell lymphoma (MCL), follicular lymphoma (FL), including low-grade, intermediate-grade and high-grade FL, cutaneous follicle center lymphoma, marginal zone B cell lymphoma (MALT type, nodal and splenic type), hairy cell leukemia, diffuse large B cell lymphoma, Burkitt's lymphoma, plasmacytoma, plasma cell myeloma, post-transplant lymphoproliferative disorder, Waldenstrom's macroglobulinemia, and anaplastic large-cell lymphoma (ALCL).

Examples of "immune disorders" and diseases in which IGHV1-69 encoded BCRs expressing B cells are involved which can be treated and/or prevented include psoriasis, psoriatic arthritis, dermatitis, systemic scleroderma and sclerosis, inflammatory bowel disease (IBD), Crohn's disease, ulcerative colitis, respiratory distress syndrome, meningitis, encephalitis, uveitis, glomerulonephritis, eczema, asthma, atherosclerosis, leukocyte adhesion deficiency, multiple sclerosis, Reynaud's syndrome, Sjogren's syndrome, juvenile onset diabetes, Reiter's disease, Behcet's disease, immune complex nephritis, IgA nephropathy, IgM polyneuropathies, immune-mediated thrombocytopenias, such as acute idiopathic thrombocytopenic purpura and chronic idiopathic thrombocytopenic purpura, hemolytic anemia, myasthenia gravis, lupus nephritis, systemic lupus erythematosus, rheumatoid arthritis (RA), atopic dermatitis, pemphigus, Graves' disease, Hashimoto's thyroiditis, Wegener's granulomatosis, Omenn's syndrome, chronic renal failure, acute infectious mononucleosis, HN, and herpes virus associated diseases. Further examples are severe acute respiratory distress syndrome and choreoretinitis. Yet further examples are diseases and disorders caused by infection of B-cells with virus, such as Epstein-Barr virus (EBV).

A "therapeutic agent" encompasses both a biological agent such as an antibody, a peptide, a protein, an enzyme or a chemotherapeutic agent.

A "chemotherapeutic agent" is a chemical compound useful in the treatment of cancer. Examples of chemotherapeutic agents include Erlotinib (TARCEVA®, Genentech/OSI Pharm.), Bortezomib (VELCADE®, Millennium Pharm.), Fulvestrant (FASLODEX®, AstraZeneca), Sutent (SU11248, Pfizer), Letrozole (FEMARA®, Novartis), Imatinib mesylate (GLEEVEC®, Novartis), PTK787/ZK 222584 (Novartis), Oxaliplatin (Eloxatin®, Sanofi), 5-FU (5-fluorouracil), Leucovorin, Rapamycin (Sirolimus, RAPAMUNE®, Wyeth), Lapatinib (TYKERB®, GSK572016, Glaxo Smith Kline), Lonafarnib (SCH 66336), Sorafenib (BAY43-9006, Bayer Labs), and Gefitinib (IRESSA®, AstraZeneca), AG1478, AG1571 (SU 5271; Sugen), alkylating agents such as thiotepa and CYTOXAN® cyclophosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethylenethiophosphoramide and trimethylomelamine; acetogenins (especially bullatacin and bullatacinone); a camptothecin (including the synthetic analog topotecan); bryostatin; callystatin; CC-1065 (including its adozelesin, carzelesin and bizelesin synthetic analogs); cryptophycins (particularly cryptophycin 1 and cryptophycin 8); dolastatin; duocarmycin (including the synthetic analogs, KW-2189 and CB1-TM1); eleutherobin; pancratistatin; a sarcodictyin; spongistatin; nitrogen mustards such as chlorambucil, chlomaphazine, chlorophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gammaII and calicheamicin omegall (Angew Chem. Intl. Ed. Engl. (1994) 33:183-186); dynemicin, including dynemicin A; bisphosphonates, such as clodronate; an esperamicin; as well as neocarzinostatin chromophore and related chromoprotein enediyne antibiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, ADRIAMYCIN® (doxorubicin), morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, porfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogs such as denopterin, methotrexate, pteropterin, trimetrexate; purine analogs such as fludarabine, 6-mercaptopurine, thiamniprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK® polysaccharide complex (JHS Natural Products, Eugene, Oreg.); razoxane; rhizoxin; sizofuran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., TAXOL® (paclitaxel; Bristol-Myers Squibb Oncology, Princeton, N.J.), ABRAXANE® (Cremophor-free), albumin-engineered nanoparticle formulations of paclitaxel (American Pharmaceutical Partners, Schaumberg, Ill.), and TAXOTERE® (doxetaxel; Rhone-Poulenc Rorer, Antony, France); chloranmbucil; GEMZAR® (gemcitabine); 6-thioguanine; mercaptopurine; methotrexate; platinum analogs such as cisplatin and carboplatin; vinblastine; etoposide (VP-16); ifosfamide; mitoxantrone; vincristine; NAVELBINE® (vinorelbine); novantrone; teniposide; edatrexate; daunomycin; aminopterin; capecitabine (XELODA®); ibandronate; CPT-11; topoisomerase inhibitor RFS 2000; difluoromethylornithine (DMFO); retinoids such as retinoic acid; and pharmaceutically acceptable salts, acids and derivatives of any of the above.

Also included in the definition of "chemotherapeutic agent" are: (i) anti-hormonal agents that act to regulate or inhibit hormone action on tumors such as anti-estrogens and selective estrogen receptor modulators (SERMs), including, for example, tamoxifen (including NOLVADEX®; tamoxifen citrate), raloxifene, droloxifene, 4-hydroxytamoxifen, trioxifene, keoxifene, LY117018, onapristone, and FARESTON® (toremifene citrate); (ii) aromatase inhibitors that inhibit the enzyme aromatase, which regulates estrogen production in the adrenal glands, such as, for example, 4(5)-imidazoles, aminoglutethimide, MEGASE® (megestrol acetate), AROMASIN® (exemestane; Pfizer), formestanie, fadrozole, RIVISOR® (vorozole), FEMARA® (letrozole; Novartis), and ARIMIDEX® (anastrozole; AstraZeneca); (iii) anti-androgens such as flutamide, nilutamide, bicalutamide, leuprolide, and goserelin; as well as troxacitabine (a 1,3-dioxolane nucleoside cytosine analog); (iv) protein kinase inhibitors; (v) lipid kinase inhibitors; (vi) antisense oligonucleotides, particularly those which inhibit expression of genes in signaling pathways implicated in aberrant cell proliferation, such as, for example, PKC-alpha, Ralf and H-Ras; (vii) ribozymes such as VEGF expression inhibitors (e.g., ANGIOZYME®) and HER2 expression inhibitors; (viii) vaccines such as gene therapy vaccines, for example, ALLOVECTIN®, LEUVECTIN®, and VAXID®; PROLEUKIN® rIL-2; a topoisomerase 1 inhibitor such as LURTOTECAN®; ABARELIX® rmRH; (ix) anti-angiogenic agents such as bevacizumab (AVASTIN®, Genentech); and (x) pharmaceutically acceptable salts, acids and derivatives of any of the above. Other anti-angiogenic agents include MMP-2 (matrix-metalloproteinase 2) inhibitors, MMP-9 (matrix-metalloproteinase 9) inhibitors, COX-II (cyclooxygenase II) inhibitors, and VEGF receptor tyrosine kinase inhibitors. Examples of such useful matrix metalloproteinase inhibitors that can be used in combination with the present compounds/compositions are described in WO 96/33172, WO 96/27583, EP 818442, EP 1004578, WO 98/07697, WO 98/03516, WO 98/34918, WO 98/34915, WO 98/33768, WO 98/30566, EP 606,046, EP 931,788, WO 90/05719, WO 99/52910, WO 99/52889, WO 99/29667, WO 99/07675, EP 945864, U.S. Pat. Nos. 5,863,949, 5,861,510, and EP 780,386, all of which are incorporated herein in their entireties by reference. Examples of VEGF receptor tyrosine kinase inhibitors include 4-(4-bromo-2-fluoroanilino)-6-methoxy-7-(1-methylpiperidin-4-ylmethoxy)quinazoline (ZD6474; Example 2 within WO 01/32651), 4-(4-fluoro-2-methylindol-5-yloxy)-6-methoxy-7-(3-pyrrolidin-1-ylpropoxy)-quinazoline (AZD2171; Example 240 within WO 00/47212), vatalanib (PTK787; WO 98/35985) and SU11248 (sunitinib; WO 01/60814), and compounds such as those disclosed in PCT Publication Nos. WO 97/22596, WO 97/30035, WO 97/32856, and WO 98/13354).

Other examples of chemotherapeutic agents include inhibitors of PI3K (phosphoinositide-3 kinase), such as those reported in Yaguchi et al (2006) Jour. of the Nat. Cancer Inst. 98(8):545-556; U.S. Pat. Nos. 7,173,029; 7,037,915; 6,608,056; 6,608,053; 6,838,457; 6,770,641; 6,653,320; 6,403,588; WO 2006/046031; WO 2006/046035; WO 2006/046040; WO 2007/042806; WO 2007/042810; WO 2004/017950; US 2004/092561; WO 2004/007491; WO 2004/006916; WO 2003/037886; US 2003/149074; WO 2003/035618; WO 2003/034997; US 2003/158212; EP 1417976; US 2004/053946; JP 2001247477; JP 08175990; JP 08176070; U.S. Pat. No. 6,703,414; and WO 97/15658, all of which are incorporated herein in their entireties by reference. Specific examples of such PI3K inhibitors include SF-1126 (PI3K inhibitor, Semafore Pharmaceuticals), BEZ-235 (PI3K inhibitor, Novartis), XL-147 (PI3K inhibitor, Exelixis, Inc.).

The term "epitope" refers to a protein determinant capable of specific binding to an antibody. Epitopes usually consist of chemically active surface groupings of molecules such as amino acids or sugar side chains and usually have specific three dimensional structural characteristics, as well as specific charge characteristics.

"Blocking" antibody or an "antagonist" antibody is one which inhibits or reduces biological activity of the antigen it binds such as CD20. Preferred blocking antibodies or antagonist antibodies substantially or completely inhibit the biological activity of the antigen. Desirably, the biological activity is reduced by 10%, 20%, 30%, 50%, 70%, 80%, 90%, 95%, or even 100%.

An "agonist antibody", as used herein, is an antibody which mimics at least one of the functional activities of a reference polypeptide of interest.

An "anti-idiotypic (anti-Id) antibody" is an antibody which recognizes unique determinants generally associated with the antigen-binding site of an antibody. An Id antibody can be prepared by immunizing an animal of the same species and genetic type (e.g., mouse strain) as the source of the mAb with the mAb to which an anti-Id is being prepared. The immunized animal will recognize and respond to the idiotypic determinants of the immunizing antibody by producing an antibody to these idiotypic determinants (the anti-Id antibody). See, for example, U.S. Pat. No. 4,699,880, which is herein entirely incorporated by reference. The anti-Id antibody may also be used as an "immunogen" to induce an immune response in yet another animal, producing a so-called anti-anti-Id antibody. The anti-anti-Id may be epitopically identical to the original mAb which induced the anti-Id. Thus, by using antibodies to the idiotypic determinants of a mAb, it is possible to identify other clones expressing antibodies of identical specificity.

An "isolated" antibody is one separated and/or recovered from its natural environment. Contaminant components of its natural environment are materials which would interfere with diagnostic or therapeutic uses for the antibody, and may include enzymes, hormones, and other proteinaceous or nonproteinaceous solutes. In preferred aspects, the antibody will be purified (1) to greater than 95% by weight of antibody as determined by, for example, the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE (sodium dodecyl sulfate polyacrylamide gel electrophoresis) under reducing or nonreducing conditions using Coomassie blue or, preferably, silver stain. Isolated antibody includes the CD20 antibody in situ within recombinant cells since at least one component of the antibody's natural environment will not be present. Ordinarily, however, isolated antibody will be prepared by at least one purification step.

As used herein, the term "engineered antibody" or "altered antibody" includes an antibody with significant human frameworks and constant regions (CL, CH domains (e.g., CH1, CH2, CH3), and hinge), and CDRs derived from antigen binding antibodies such as anti-CD20 antibodies or fragments thereof. Fully human frameworks comprise frameworks that correspond to human germline sequences as well as sequences with somatic mutations. CDRs may be derived from one or more CDRs that associate with or bind to antigen in or outside of the context of any antibody framework. For example, the CDRs of the human engineered antibody of the present invention directed to CD20 may be derived from CDRs that bind antigen in the context of a mouse antibody framework and then are engineered to bind antigen in the context of a human framework. Often, the human engineered antibody is substantially non-immunogenic in humans.

Similarly, antibodies designated primate (monkey, baboon, chimpanzee, etc.), rodent (mouse, rat, rabbit, guinea pig, hamster, and the like) and other mammals designate such species, sub-genus, genus, sub-family, and family specific antibodies. Further, chimeric antibodies can include any combination of the above. Such changes or variations optionally and preferably retain or reduce the immunogenicity in humans or other species relative to non-modified antibodies. A human engineered antibody is distinct from a chimeric or humanized antibody.

An engineered antibody can be produced by a non-human animal or prokaryotic or eukaryotic cell that is capable of expressing functionally rearranged human or human engineered immunoglobulin (e.g., heavy chain and/or light chain) genes. Further, when a engineered antibody is a single chain antibody, it can comprise a linker peptide that is not found in native human or non-human antibodies. For example, an Fv can comprise a linker peptide, such as two to about eight glycine or other amino acid residues, which connects the variable region of the heavy chain and the variable region of the light chain. Such linker peptides are considered to be of human origin.

Bispecific, heterospecific, heteroconjugate or similar antibodies can also be used that are monoclonal, preferably, human, human engineered, resurfaced or humanized, antibodies that have binding specificities for at least two different antigens. In the present case, one of the binding specificities is for at least one antigenic protein, the other one is for another antigenic protein. Methods for making bispecific antibodies are known in the art. Traditionally, the recombinant production of bispecific antibodies is based on the co-expression of two immunoglobulin heavy chain-light chain pairs, where the two heavy chains have different specificities (Milstein and Cuello, Nature 305:537 (1983)). Because of the random assortment of immunoglobulin heavy and light chains, these hybridomas (quadromas) produce a potential mixture of about 10 different antibody molecules, of which only one has the correct bispecific structure. The purification of the correct molecule is usually done by affinity chromatography steps or as otherwise described herein. Similar procedures are disclosed, e.g., in WO 93/08829, U.S. Pat. Nos. 6,210,668, 6,193,967, 6,132,992, 6,106,833, 6,060,285, 6,037,453, 6,010,902, 5,989,530, 5,959,084, 5,959,083, 5,932,448, 5,833,985, 5,821,333, 5,807,706, 5,643,759, 5,601,819, 5,582,996, 5,496,549, 4,676,980, WO 91/00360, WO 92/00373, EP 03089, Traunecker et al., EMBO J. 10:3655 (1991), Suresh et al., Methods in Enzymology 121:210 (1986), U.S. 20090258026, U.S. 20060140946 and U.S. 20070298040, each entirely incorporated herein by reference.

Antibody "effector functions" refer to those biological activities attributable to the Fc region (a native sequence Fc region or amino acid sequence variant Fc region) of an antibody, and vary with the antibody isotype. Examples of antibody effector functions include: C1q binding and complement dependent cytotoxicity (CDC); Fc receptor binding; antibody-dependent cell-mediated cytotoxicity (ADCC); phagocytosis; down regulation of cell surface receptors (e.g. B cell receptor); and B cell activation.

"Human effector cells" are leukocytes which express one or more FcRs and perform effector functions. In certain aspects, the cells express at least FcγRIII and perform ADCC effector function(s). Examples of human leukocytes which mediate ADCC include peripheral blood mononuclear cells (PBMC), natural killer (NK) cells, monocytes, cytotoxic T cells and neutrophils. The effector cells may be isolated from a native source, e.g., from blood.

All of the above U.S. patents, U.S. patent application publications, U.S. patent applications, and foreign patents, foreign patent applications referred to in this specification, are incorporated herein by reference in their entirety.

All publications cited in the specification are indicative of the level of skill of those skilled in the art to which this invention pertains. All these publications are herein incorporated by reference in their entirety to the same extent as if each individual publication were specifically and individually indicated to be incorporated by reference.

EXAMPLES

Example 1: Material and Methods

Cells 293T (CRL-11268) cell line was purchased from American Type Culture Collection and incubated in 10% FBS Dulbecco's Modified Eagle's Medium. 293F cell line was purchased from Invitrogen™ and incubated in 293 FreeStyle serum-free medium (Life Technologies, Carlsbad, Calif.). IGHV1-69 positive B-CLL cells were isolated from B-CLL patients, obtained from Dr. Jennifer Brown (Dana-Farber Cancer Institute, Department of Medical Oncology) and cultured in IMDM, GlutaMAX medium (Life Technologies) supplemented with 10% Human AB Serum (Gemini Bio-Products, West Sacramento, Calif.), penicillin and streptomycin at concentrations of 100 U/ml and 100 mg/ml (Sigma-Aldrich, St. Louis, Mo.), 50 µg/ml Transferrin (Roche, Mannheim, Germany) and 5 µg/ml Human Insulin (Roche). All patients had signed written informed consent to an institutional review board-approved tissue acquisition protocol.

Expression and Purification of Antibodies

MuG6, HuG6 variants, IGHV1-69 idiotypic antibodies (D80, F70, and F43) and control antibody (11A) were produced as described previously. Briefly, scFv-Fcs were constructed by cloning the scFv into pcDNA3.1-Hinge vector in frame with human IgG1 Fc region without CH1 domain. IgG1s were generated by cloning heavy chain variable region (VH) and light chain variable region (VL) into TCAE5.3 vector. Fc-mutated HuG6.3 was constructed in TCAE5.3 with Leu234Ala and Leu235Ala mutations on CH2 domain. Antibodies (scFv-Fc and IgG1) were produced in 293F cells and MuG6 was harvested from the supernatant of MuG6 hybridoma. All the antibodies were further purified by protein A sepharose affinity chromatography (GE Healthcare, Newark, N.J.). In addition, D80 scFv was cloned into C-terminal histidine tagged pET22b(+) bacterial expression vector (Novagen, Madison, Wis.), expressed in E. coli BL21(DE3) (Novagen), and purified from supernatant of lysed cells using Nickel affinity chromatography via ÄKTA-Purifier FPLC (GE Healthcare).

Construction of the Humanized GTL Mouse Model and the Verification of G6 In Vivo Activity Using Flow Cytometry The humanized mice were constructed in 5- to 7-week-old female NSG mice (NOD.Cg-Prkdc$^{scid}$ Il2rg$^{tm1Wjl}$/SzJ, Jackson Laboratories, Bar Harbor, Me., as described previously,[67-69] after sublethal whole body irradiation (325 rads) with a Gammacell 40 Exactor (Best Theratronics, Ottawa, ON, Canada) and by injecting CD34$^+$ hematopoietic stem cells intravenously and implanting 1 mm$^3$ pieces of human fetal thymus and liver tissues under the kidney capsule. Each cohort was produced with tissues from a single donor. CD34$^+$ HSC were isolated from the remaining portion of the same fetal liver using anti-human CD34 microbeads (Miltenyi, Auburn, Calif.) with >98% purity determined by flow cytometry after staining with anti-CD34-PE (Miltenyi). All engrafted mice were housed under Biosafety Level-2 conditions and provided with autoclaved food and water supplemented with Baytril (Bayer, Shawnee Mission, Kans.). All animal experiments were approved by the Institutional Animal Care and Research Committee and the Office of Human Subjects Research at the Dana-Farber Cancer Institute, Boston, Mass.

After 16 weeks post-engraftment, the levels of human immune reconstitution were measured by flow cytometry. The GTL mice were randomly assigned into different groups and treated with recombinant human CD40 ligand (rCD40L for maintaining B cell population). The mice were additionally treated in the presence or absence of 10 µg MuG6 or control antibody by intravenously injection. All the mice were bled out 7 days post-injection; blood samples were centrifuged to separate the plasma fraction, and then the cell pellets were treated with ammonium chloride (ACK) lysing solution (Life Technologies) to enrich for PBMCs. PBMCs and mouse plasma were further stained with fluorochrome-conjugated antibodies to different cell surface markers, followed by multi-color flow cytometry using a LSRII (BD Biosciences, San Jose, Calif.). The following fluorochrome-conjugated antibodies were used: anti-human CD45-APC (clone H130), CD20-phycoerythrin (PE) (MB19-1) (both from eBioscience, San Diego, Calif.), and MuG6-FITC (conjugated using Pierce FITC antibody labeling kit, Thermo Scientific, Hudson, N.H.). Gating was performed on viable lymphoid cells based on the forward and side scatter profiles of the total cells, and stained cells were analyzed within the lymphoid gate. A comparison between the percentages of human $CD45^+$ and endogenous mouse $CD45^+$ was performed to measure the level of immune reconstitution in GTL mice, and other markers were used to analyze the different human B-lymphocyte subsets. Background staining was determined using the corresponding isotype controls or staining cells isolated from non-engrafted animals. Data were analyzed using flowjo version 8.6.3 (Tree Star, Ashland, Oreg.).

ELISA Binding Assay

The binding activities of MuG6 and HuG6 variants (HuG6s, including HuG6.1, HuG6.2, and HuG6.3) were tested and compared using an IGHV1-69 cognate antibody. D80 IgG1 was chosen as an antigen (cross-reactive idiotype) that uses the 51p1 sequence with IGHV1-69 germline configuration. Biotinylation of MuG6 and HuG6s were done with a commercial biotinylation kit (Pierce) and ELISA analysis was performed. Briefly, D80 IgG1 (2 µg/ml) were coated on to a 96-well Maxisorp plate and incubated overnight at 4° C. Unbound protein was washed away with PBST (0.05% Tween-20 in PBS) and blocked with 2% milk for 1 hour at 25° C. Diluted biotinylated MuG6 and HuG6s as scFv-Fc format were added to the wells and incubated at 25° C. for 1 hour. Plates were washed with PBST, added streptavidin-HRP (1:1000), and then incubated at 25° C. for 30 minutes. The results were measured at OD450 using an ELISA reader by developing with tetramethylbenzidine solution. For human IgG and IgM ELISA, plates were coated overnight at 4° C. with capture antibody MuG6 (100 µg/ml) and developed with detection antibodies, anti-human IgM and IgG (Bethyl Labs), conjugated with HRP.

BIAcore Biosensor Assay

The binding of MuG6, HuG6.2, or HuG6.3 scFv-Fcs to D80 scFv was compared using surface plasmon resonance instrument BIAcore T100 optical biosensor (BIAcore AB, Uppsala, Sweden). The experiments were performed at 4° C. in HBS-P buffer (150 mM NaCl, 10 mM HEPES, 0.05% surfactant P20, and 50 µM EDTA). Briefly, the C-terminal histidine-tagged D80 scFv was first immobilized on a NTA sensor chip with around 100 RU captured level. MuG6 and HuG6s were then injected at various concentrations (0.1, 0.5, 1.5, 4.5, and 14.5 nM) via single cycle kinetics wizard program. The capture surface was regenerated using 0.35 M EDTA, followed by the injection of the running buffer. Double reference subtraction of the data was performed to correct for the buffer contribution to the instrument signal to noise ratio. After this initial subtraction, kinetics analysis of the data was performed using the BIAevaluation software version 2.0.3 (Biacore AB) assuming a simple 1:1 analyte binding model.

Meso Scale Discovery Immunoassay

MSD plates were coated overnight at 4° C. with 6 µl of 1.042 µg/ml HuG6.3 IgG1 in PBS. Coated plates were washed and blocked with 75 µl 2% BSA in PBS at 37° C. for 1 h. D80, F43, F70, and S37 (IGHV1-18-encoding scFv) phagemids were diluted in 2% milk PBST and added to the wells. The plates were incubated at 37° C. for 1 h. Plates were washed three times with PBST and then incubated with 10 µl of diluted sulfo-tagged-anti-M13 mAb (6 µg/ml) at 37° C. for 1 h. After another wash step, 1× Read Buffer was added and the electrochemiluminescence was measured with a MSD Sector Imager 2400 or 6000.

CDC and ADCC Assays

The IGHV1-69 cognate antibodies (D80, F70, and F43) and an irrelevant control antibody (11A) were constructed into an expression vector, pHAGE.[36] The scFv of antibodies were inserted between the leader peptide (LP) and the Fc region of a human IgG1 molecule. The Fc domain was linked in-frame to a short segment of extracellular domain of CD28, followed by the respective transmembrane domain and cytoplamic domain of CD28 and the incorporation motif of HIV-1 gp41, forming a sequence as LP-scFvs-CD28-gp41. A reporter gene, IRES-ZsGreen, was further constructed into the vector after the gp41. 293T cells were transfected with DNA encoding for scFvs-Fc-CD28-gp41-IRES-ZsGreen plasmids. At 48 hours post transfection, the expression of D80, F70, F43, and 11A on 293T cells were analyzed by a fluorescence microscope and flow cytometry using APC-conjugated G6 or anti-human IgG (Biolegend, San Diego, Calif.) antibodies. The ZsGreen positive cells were further sorted (via FACS) as target cells.

The LDH release assay was described previously.[48] Briefly, D80-, F70-, F43-, and 11A-expressed 293T cells were used as target cells ($4 \times 10^4$ cells/well) and incubated with medium containing rabbit serum complement (Cedarlane Laboratories, Hornby, Ontario, Canada) in the absence and presence of MuG6 and HuG6s. After 6 hours incubation, the supernatants were harvested and measured using non-radioactive cytotoxicity assay kits (Promega, Madison, Wis.) at 490 nm.

For ADCC, human PBMCs were used as effector cells and incubated with target cells ($2 \times 10^4$ cells/well). Cells were plated into 96-well plates, incubated with antibodies at different concentrations, and then effector cells were added at an effector/target (E/T) ratio of 25:1 for 4 hours incubation at 37° C. The supernatants were harvested and detected by LDH release assay.

In Vivo Activity of HuG6.3 on Xenogeneic B-CLL from Patients

Eight-week-old NSG mice received $1 \times 10^6$ PBMCs from B-CLL patients and $5 \times 10^6$ human nature killer (NK) cells through intravenous injection. PBMCs from B-CLL patients consented as described above were isolated by Ficoll-Paque PLUS (GE Healthcare Life Sciences, Pittsburgh, Pa.). NK cells were isolated using EasySep™ Human NK Cell Enrichment Kit (StemCell Technologies, Vancouver, British Columbia, Canada). Mice were further treated with 10 mg/kg control IgG1, MuG6, HuG6.3, and mHuG6.3 (a mutation version of HuG6.3 with L234A and L235A mutation in Fc domain intravenously. After 16 hours, mouse blood samples were harvested for further staining, including human CD45, CD19, and CD56, and then analyzed by flow cytometry.

Statistics

Data were analyzed using One-Way ANOVA or two-sided unpaired Student's t-test. The difference was considered statistically significant if P value<0.05. "*", "", and "*" indicate p<0.05, 0.01 and 0.001, respectively. All values and bars are represented as mean±standard deviation (S.D.).

Example 2: MUG6 Antibody Mediates Systemic Depletion of IGHV1-69 Encoding B Cells in GTL Mice To determine if MuG6 could mediate in vivo depletion of IGHV1-69 G6-id+ expressing lymphocytes, we utilized a GTL mouse model (NOD.Cg-Prkdc$^{scid}$ Il2rg$^{tm1wjl}$/SzJ (NSG) mice engrafted with human fetal bone marrow, liver, and thymus tissue for generation of human immunity) to investigate the in vivo immunodepletion activity of MuG6 on the reconstituted B cell population. First, the peripheral blood from GTL mice was stained for human CD45+ mononuclear cells at 16 weeks post immune reconstruction to verify levels of engraftment. These GTL mice were then randomly assigned into different groups and treated with MuG6 or control antibody. Seven days after treatment, mouse blood was harvested to analyze serum MuG6 levels, as well as the total CD20+ B cell population and the G6-id+ B cells by fluorescence-activated cell sorting (FACS). Serum MuG6 levels at days 7, 9 and 10 were 12.4, 7.2 and 5.4 ng/ml, respectively, after correcting for background binding by normal mouse serum (FIG. 7). As shown in FIG. 1A, MuG6 treatment did not result in a change in the total B-cell population; however, the G6-id+ B cell subpopulation dramatically decreased in MuG6-treated mice compared to the other groups (FIG. 1B). While it is possible that this result could be due to saturation of 51p1 allele encoded BCRs by serum MuG6, this is unlikely because the day 7 serum MuG6 level (0.08 nM) was significantly below the equilibrium dissociation constant ($K_D$) of MuG6 for the IGHV1-69 idiotype (discussed below). Moreover, the expression of the cognate IgM and IgG G6-id+ antibodies in the plasma of the MuG6-treated but not control IgG-treated mice was markedly decreased at day 7 (FIGS. 1C and 1D) and day 21 (FIG. 8). The dramatic loss of G6-id+ B cells and loss of 51p1 allele encoding IgM and IgG in MuG6-treated mouse plasma demonstrate that MuG6 has the capacity to deplete IGHV1-69 G6-id+ Bcells in vivo.

Example 3: Humanization of MUG6

The MuG6 heavy and light chain variable regions (VH and VL) genes from the hybridoma cell line were individually recovered by RT-PCR using specific primers for mouse antibody variable genes. The MuG6 VH and VL belong to mouse $V_H1$ (IGHV1-5*01), $J_H4$ (IGHJ4*01) and $D_H2$ (IGHD2-12*01) and $V_K14$ (IGKV14-100*01) and $J_K5$ (IGKJ5*01) segments, respectively (FIG. 2). Next, the structure-guided CDR grafting approach was employed to humanize MuG6. For selection of the human acceptor FRW template for CDR-grafting, the VH and VL amino acid sequences of MuG6 were separately compared to human antibody sequences in the IMGT database to identify the most similar human antibody and Ig germline VH and VL sequences. The best-matched human Ig germline V sequences were IGHV1-46*13 (68.4% homology to MuG6-VH) and IGKV1-16*01 (67.4% homology to MuG6-VL). Using IgG protein sequence blast, MuG6 was compared with other humanized or human monoclonal antibodies (mAbs), including 5c8 (anti-CD40L), Fab 7G10 (anti-IL23), hATR-5 (anti-Tissue factor), 1C12 (anti-musk odorant traseolide), CAMPATH-1H (anti-CD52), and a mouse $F_{ab}$ 64M-2 (anti-DNA t(6-4) T photoproduct), and revealed variable degree of sequence homology. Subsequently, Fab 64M-2 structure (PDB-ID: 1EHL) was chosen as a template for VH chain, with 87.5% sequence identity and 92% similarity to MuG6. As such, the FRW residues of 1EHL VH chain were unchanged, but the CDRs were mutated to reflect MuG6 CDRs. Closer examination of this modified structure did not reveal any major steric clashes. In addition, 1C12 structure was chosen as a template for VL chain, with 94% sequence identity and 96% similarity to MuG6 sequence. Further analysis in the structure revealed one steric clash with Val89 (CDR-L3) when Leu4 (FRW-L1) was replaced with Met4 (humanized). The final humanized MuG6 was designed through multiple sequence alignment (CLUSTALX) and the most conserved FWR residues. In addition, we manually exchanged the residues in both VH and VL FWRs to the consensus human germline sequence and then generated HuG6 version 1 (HuG6.1). Sequence alignment of amino acids between the MuG6 and HuG6.1 is shown in FIG. 2, with 18 and 18 amino acids mutations in the VH and VL, respectively.

Example 4: Structure-Based AB-Initio Generation of Antibody Homology Model for Humanization The ab-initio generated homology model of MuG6 was used to identify surface accessible (solvent exposed) residues via WAM server and visualized through DeepView program (Swiss-PdbViewer, http://www.expasy.org/spdbv/) [33] (FIG. 3A). These residues were identical to the human germline sequence in the FWR regions. In-silico mutations were performed via PyMOL mutagenesis tool to replace framework residues of mouse to human HuG6.1 sequence (Delano scientific-www.pymol.org). GROMOS force field energy minimization parameter was then applied to the homology model HuG6.1 using DeepView program with default settings, and displayed certain residues with high entropy in their side chain rotamers (FIG. 3B). Examination of this energy minimized homology model of HuG6.1 revealed residues that had distorted geometry or steric clashes with other residues. These anomalies upon closer examination with either distorted geometry or steric clashes were further visualized in PyMOL (FIG. 3C-F). Residues with steric clashes included (FIG. 3C, left) Lys73 (FRW-H3) with Gly54 (CDR-H2), (FIG. 3D, left) Met4 (FRW-L1) with Cys88 (FRW-L3), (FIG. 3E, left) Tyr36 (FRW-L2) with Leu100b (CDR-H3), and (FIG. 3F, left) Gln79 (FRW-L3) with Arg61 (FRW-L3). Based on the conserved homologous sequence alignment and structural analysis, the residues that caused steric clashes were back mutated to the mouse counterpart, including (1) Lys73 to Thr73 (FIG. 3C, right), (2) Met4 to Leu4 (FIG. 3D, right), (3) Tyr36 to Leu36 (FIG. 3E, right), and (4) Gln79 to Glu79 (FIG. 3F, right). In summary, four identified residues were mutated back to the original mouse residues, including one residue in VH (Thr73) and three residues in VL (Leu4, Leu36, Glu79), creating HuG6 version 2 (HuG6.2). Furthermore, to test the contribution of threonine (mouse germline VH chain) as opposed to lysine (human germline) in binding to the target, this T73K mutation (FIG. 3C) was made as HuG6 version 3 (HuG6.3). The sequence alignment highlighted the differences in MuG6 with different versions of HuG6 (HuG6.1, HuG6.2, and HuG6.3) as shown in FIG. 2.

Example 5: Binding Affinities of MUG6 and HUG6 Variants Antibodies for G6-ID+ D80 MAB The humanized $V_H$ and $V_L$ genes of HuG6 variants (HuG6s) were de novo synthesized and codon-optimized for mammalian cell expression. The binding affinities of MuG6 and HuG6s scFv-Fcs to G6-id+ D80 IgG were further analyzed by ELISA. The results in FIG. 4A showed that HuG6.1 lost its binding ability; however, HuG6.2 and HuG6.3 exhibited even better binding affinity than the parental MuG6. Next, we used BIAcore to interrogate the binding kinetics of MuG6 and HuG6s scFv-Fcs against D80 scFv. As shown in FIG. 4B and FIG. 9 the $K_D$ of MuG6, HuG6.2, and HuG6.3 against D80 scFv were 0.35, 0.23, and 0.16 nM, respectively. These results were consistent with the apparent higher affinity of HuG6.2 and HuG6.3 over MuG6 by ELISA.

Interestingly, only one residue difference between HuG6.2 (Thr73) and HuG6.3 (Lys73) influenced the binding affinity, suggesting a definitive role of lysine in modulating the binding pattern. The in-silico modeling suggested that residue Lys73 (FRW-H2) has a steric clash with Gly54 (CDR-H2), and thus the Lys73 was back mutated to mouse residue Thr73 (FIG. 3C). However, this resulted in loss of affinity, albeit small, indicating that Lys73 may cause subtle changes in the binding site to position CDR-H2 in a conformation that enables HuG6.3 to increase its binding affinity to D80. These results showed that humanization of MuG6 was successful and HuG6.2 and HuG6.3 have better binding affinity than MuG6.

Three IGHV1-69 encoding scFvs (D80, F43, and F70) and one control IGHV1-18 encoding scFv (S37) were investigated the binding affinity to HuG6.3 using Meso Scale Discovery (MSD) immunoassay. Interestingly, HuG6.3 bound more strongly to F43 and F70, which are scFvs with 100% identity to IGHV1-69*01 germline gene, compared to D80 (89% identity). There was no reactivity of HuG6.3 to S37 scFv (FIG. 4C). To further test the binding affinity, a HuG6.3-labeled sensor system was used to measure the association and dissociation kinetics against IGHV1-69 encoding D80 and F43 scFv-Fcs coated on the SA sensor tip surfaces (FIG. 10). The Octet-Red assay results showed specific binding between the HuG6.3 and IGHV1-69 encoding scFv-Fcs, whereas it did not bind the control scFv-Fc. Moreover, there was a 3.5 fold slower Kon for HuG6.3 binding to germline F43 compared to D80 scFv-Fc and a circa 600-fold slower Koff with a resulting 50-fold increase in binding affinity. These results provide additional support that HuG6.3 can specifically bind to IGHV1-69 encoding immunoglobulins with higher affinity binding for unmutated IGHV1-69 51p1 alleles.

Example 6: MUG6 and HUG6s Mediates Killing of IGHV1-69 Encoded G6-ID+ Cells Through CDC and ADCC To delineate the biological mechanism(s) by which MuG6 treatment caused depletion of G6-id+ B cells, CDC and ADCC assays were performed. To mimic G6-id+ B-CLL cells, we used IGHV1-69 encoding D80, F70, and F43 scFvs (FIG. 11A) that showed 89, 100, and 100% identity to IGHV1-69*01 germline gene, respectively, to construct G6-id+293 T cells by transfection (FIG. 11A). To anchor the surface-expressed G6-id+ scFv to the cell membrane, scFv-Fc proteins were fused, in frame, to a transmembrane moiety.[36] To follow transfection efficiency, ZsGreen was co-expressed in the bicistronic message and was visualized by fluorescence microscope (FIG. 11B). Surface expression of the G6-id+ and G6-id− (11A-scFv) antibodies was analyzed by FACS stained with allophycocyanin (APC)-conjugated MuG6 and ZsGreen (FIG. 11C).

IGHV1-69 and non-IGHV1-69 transduced 293T cells were used as the target cells for CDC and ADCC assays. The HuG6.2 and HuG6.3 scFv-Fcs were further evaluated for their capacity to mediate CDC activity on the G6-id+293 T cells using rabbit serum. As shown in FIG. 5A-C, circa 20% of target cells were killed when treated with Mu/HuG6s. HuG6.3 exhibited a slightly better potent CDC activity than HuG6.2 against the three G6-id+293 T cells, and had comparable CDC activity as MuG6. The specificity of the CDC-mediated killing was shown by the lack of cytotoxicity on negative control G6-id− 11A-293T cells (FIG. 5D). We further tested the activity of mouse anti-human Fc IgG2a and showed 25% killing activity among all transduced cells (FIG. 12A). We subsequently focused on HuG6.3 IgG1 alone in the evaluation of ADCC activity. As shown in FIG. 6A-C, HuG6.3 maintained potent ADCC activity against the three G6-id+ cell lines at 20 μg/ml, and more variable killing activity compared to MuG6 at lower antibody concentrations. Again, neither MuG6 nor HuG6.3 killed negative control G6-id− 11A-293T cells by ADCC (FIG. 6D). A mouse anti-human Fc IgG2a was used in the ADCC assay and showed 40% killing activity on all transduced 293T cells (FIG. 12B).

Example 7: MUG6 and HUG6s Mediate Killing of IGHV1-69 G6-ID+ B-CLL Cells

We investigated whether HuG6.3 could induce ADCC of IGHV1-69 G6-id+ B-CLL cells obtained from peripheral blood samples of B-CLL patients. The in vitro lactate dehydrogenase (LDH) release assay was performed by co-incubation of B-CLL target cells with peripheral blood mononuclear cells (PBMCs) from healthy donors in the presence of different antibodies. The results showed that both MuG6 and HuG6.3, but not control antibody, could mediate ADCC in a dose-dependent manner (FIG. 6E). Next, an in vivo examination of HuG6.3-mediated B-CLL killing was performed in which G6-id+ and G6-id+ B cells, (FIG. 13A) were injected with human natural killer (NK) cells and MuG6/HuG6s into NSG mice intravenously. To further confirm whether HuG6.3 could functionally deplete G6-id+ B-CLL cells, we generated a double mutant (L234A, L235A) HuG6.3 (mHuG6.3, that did not bind either FcγR or C1q) for in vivo examination. After 16-hour circulation, mouse blood was harvested and circulating cells were detected by FACS. The results in FIG. 6F show that G6-id+ B-CLL cells were depleted in vivo in both MuG6-treated and HuG6.3-treated mice, but not in mice treated with control and Fc-mutated HuG6.3 (mHuG6.3). In contrast to G6-id+ patients 1-3, G6-id− patient 4 did not show depletion of CD19 B-CLL cells (FIG. 13B). Taken together, HuG6.3 demonstrates ADCC- and CDC-mediated killing of G6-id+ 293T cells and IGHV1-69-encoding G6-id+ B-CLL cells in vitro and in vivo.

Other Embodiments

While the invention has been described in conjunction with the detailed description thereof, the foregoing description is intended to illustrate and not limit the scope of the invention, which is defined by the scope of the appended claims. Other aspects, advantages, and modifications are within the scope of the following claims.

REFERENCES

1. Chiorazzi N, Rai K R, Ferrarini M. Chronic lymphocytic leukemia. N Engl J Med 2005; 352:804-15.
2. Hallek M, Cheson B D, Catovsky D, Caligaris-Cappio F, Dighiero G, Dohner H, et al. Guidelines for the diagnosis and treatment of chronic lymphocytic leukemia: a report from the International Workshop on Chronic Lymphocytic Leukemia updating the National Cancer Institute-Working Group 1996 guidelines. Blood 2008; 111:5446-56.
3. American Cancer Society: Cancer Facts and Figures 2015. Atlanta, Ga.: American Cancer Society, 2015.
4. Byrd J C, Marcucci G, Parthun M R, Xiao J J, Klisovic R B, Moran M, et al. A phase 1 and pharmacodynamic study of depsipeptide (FK228) in chronic lymphocytic leukemia and acute myeloid leukemia. Blood 2005; 105:959-67.
5. Garcia-Escobar I, Sepulveda J, Castellano D, Cortes-Funes H. Therapeutic management of chronic lymphocytic leukaemia: state of the art and future perspectives. Crit Rev Oncol Hematol 2011; 80:100-13.
6. Robak T. The role of nucleoside analogues in the treatment of chronic lymphocytic leukemia-lessons learned from prospective randomized trials. Leuk Lymphoma 2002; 43:537-48.
7. Byrd J C, Lin T S, Dalton J T, Wu D, Phelps M A, Fischer B, et al. Flavopiridol administered using a pharmacologically derived schedule is associated with marked clinical efficacy in refractory, genetically high-risk chronic lymphocytic leukemia. Blood 2007; 109:399-404.
8. Herman S E, Gordon A L, Wagner A J, Heerema N A, Zhao W, Flynn J M, et al. Phosphatidylinositol 3-kinase-delta inhibitor CAL-101 shows promising preclinical activity in chronic lymphocytic leukemia by antagonizing intrinsic and extrinsic cellular survival signals. Blood 2010; 116:2078-88.
9. Lin T S. New agents in chronic lymphocytic leukemia. Curr Hematol Malig Rep 2010; 5:29-34.
10. Byrd J C, Murphy T, Howard R S, Lucas M S, Goodrich A, Park K, et al. Rituximab using a thrice weekly dosing schedule in B-cell chronic lymphocytic leukemia and small lymphocytic lymphoma demonstrates clinical activity and acceptable toxicity. J Clin Oncol 2001; 19:2153-64.
11. Hale G, Bright S, Chumbley G, Hoang T, Metcalf D, Munro A J, et al. Removal of T cells from bone marrow for transplantation: a monoclonal antilymphocyte antibody that fixes human complement. Blood 1983; 62:873-82.
12. Lanasa M C, Allgood S D, Slager S L, Dave S S, Love C, Marti G E, et al. Immunophenotypic and gene expression analysis of monoclonal B-cell lymphocytosis shows biologic characteristics associated with good prognosis CLL. Leukemia 2011; 25:1459-66.
13. Krause G, Patz M, Isaeva P, Wigger M, Baki I, Vondey V, et al. Action of novel CD37 antibodies on chronic lymphocytic leukemia cells. Leukemia 2011.
14. Fais F, Ghiotto F, Hashimoto S, Sellars B, Valetto A, Allen S L, et al. Chronic lymphocytic leukemia B cells express restricted sets of mutated and unmutated antigen receptors. J Clin Invest 1998; 102:1515-25.
15. Damle R N, Wasil T, Fais F, Ghiotto F, Valetto A, Allen S L, et al. Ig V gene mutation status and CD38 expression as novel prognostic indicators in chronic lymphocytic leukemia. Blood 1999; 94:1840-7. 1
16. Hamblin T J, Davis Z, Gardiner A, Oscier D G, Stevenson F K. Unmutated Ig V(H) genes are associated with a more aggressive form of chronic lymphocytic leukemia. Blood 1999; 94:1848-54.
17. Lanasa M C. Novel insights into the biology of CLL. Hematology Am Soc Hematol Educ Program 2010; 2010:70-6.
18. Fais F, Ghiotto F, Hashimoto S, Sellars B, Valetto A, Allen S L, et al. Chronic lymphocytic leukemia B cells express restricted sets of mutated and unmutated antigen receptors. The Journal of clinical investigation 1998; 102:1515-25.
19. Messmer B T, Albesiano E, Messmer D, Chiorazzi N. The pattern and distribution of immunoglobulin VH gene mutations in chronic lymphocytic leukemia B cells are consistent with the canonical somatic hypermutation process. Blood 2004; 103:3490-5.
20. Ghia P, Stamatopoulos K, Belessi C, Moreno C, Stella S, Guida G, et al. Geographic patterns and pathogenetic implications of IGHV gene usage in chronic lymphocytic leukemia: the lesson of the IGHV3-21 gene. Blood 2005; 105:1678-85.
21. Stamatopoulos K, Belessi C, Moreno C, Boudjograh M, Guida G, Smilevska T, et al. Over 20% of patients with chronic lymphocytic leukemia carry stereotyped receptors: Pathogenetic implications and clinical correlations. Blood 2007; 109:259-70.
22. Messmer B T, Albesiano E, Efremov D G, Ghiotto F, Allen S L, Kolitz J, et al. Multiple distinct sets of stereotyped antigen receptors indicate a role for antigen in promoting chronic lymphocytic leukemia. J Exp Med 2004; 200:519-25.
23. Potter K N, Orchard J, Critchley E, Mockridge C I, Jose A, Stevenson F K. Features of the overexpressed V1-69 genes in the unmutated subset of chronic lymphocytic leukemia are distinct from those in the healthy elderly repertoire. Blood 2003; 101:3082-4.
24. Widhopf G F, 2nd, Kipps T J. Normal B cells express 51p1-encoded Ig heavy chains that are distinct from those expressed by chronic lymphocytic leukemia B cells. J Immunol 2001; 166:95-102.
25. Darzentas N, Hadzidimitriou A, Murray F, Hatzi K, Josefsson P, Laoutaris N, et al. A different ontogenesis for chronic lymphocytic leukemia cases carrying stereotyped antigen receptors: molecular and computational evidence. Leukemia 2010; 24:125-32.
26. Widhopf G F, 2nd, Rassenti L Z, Toy T L, Gribben J G, Wierda W G, Kipps T J. Chronic lymphocytic leukemia B cells of more than 1% of patients express virtually identical immunoglobulins. Blood 2004; 104:2499-504.
27. Murray F, Darzentas N, Hadzidimitriou A, Tobin G, Boudjogra M, Scielzo C, et al. Stereotyped patterns of somatic hypermutation in subsets of patients with chronic lymphocytic leukemia: implications for the role of antigen selection in leukemogenesis. Blood 2008; 111:1524-33.
28. Mageed R A, Dearlove M, Goodall D M, Jefferis R. Immunogenic and antigenic epitopes of immunoglobulins. XVII—Monoclonal antibodies reactive with common and restricted idiotopes to the heavy chain of human rheumatoid factors. Rheumatol Int 1986; 6:179-83.
29. Potter K N, Li Y, Mageed R A, Jefferis R, Capra J D. Molecular characterization of the VH1-specific variable region determinants recognized by anti-idiotypic monoclonal antibodies G6 and G8. Scand J Immunol 1999; 50:14-20.
30. Forconi F, Potter K N, Wheatley I, Darzentas N, Sozzi E, Stamatopoulos K, et al. The normal IGHV1-69-derived B-cell repertoire contains stereotypic patterns characteristic of unmutated CLL. Blood 2010; 115:71-7.
31. Brezinschek H P, Brezinschek R I, Dorner T, Lipsky P E. Similar characteristics of the CDR3 of V(H)1-69/DP-10 rearrangements in normal human peripheral blood and chronic lymphocytic leukaemia B cells. Br J Haematol 1998; 102:516-21.
32. Whitelegg N R, Rees A R. WAM: an improved algorithm for modelling antibodies on the WEB. Protein Eng 2000; 13:819-24.
33. Guex N, Peitsch M C. SWISS-MODEL and the Swiss-PdbViewer: an environment for comparative protein modeling. Electrophoresis 1997; 18:2714-23.
34. Stocker U, van Gunsteren W F. Molecular dynamics simulation of hen egg white lysozyme: a test of the GROMOS96 force field against nuclear magnetic resonance data. Proteins 2000; 40:145-53.
35. Daura X, Oliva B, Querol E, Aviles F X, Tapia O. On the sensitivity of M D trajectories to changes in water-protein interaction parameters: the potato carboxypeptidase inhibitor in water as a test case for the GROMOS force field. Proteins 1996; 25:89-103.
36. Taube R, Zhu Q, Xu C, Diaz-Griffero F, Sui J, Kamau E, et al. Lentivirus display: stable expression of human antibodies on the surface of human cells and virus particles. PLoS One 2008; 3:e3181.
37. Bruccoleri R E, Karplus M. Prediction of the folding of short polypeptide segments by uniform conformational sampling. Biopolymers 1987; 26:137-68.
38. Dauber-Osguthorpe P, Roberts V A, Osguthorpe D J, Wolff J, Genest M, Hagler A T. Structure and energetics of ligand binding to proteins: *Escherichia coli* dihydrofolate reductase-trimethoprim, a drug-receptor system. Proteins 1988; 4:31-47.
39. Carter P, Presta L, Gorman C M, Ridgway J B, Henner D, Wong W L, et al. Humanization of an anti-p185HER2 antibody for human cancer therapy. Proc Natl Acad Sci USA 1992; 89:4285-9.
40. Mader A, Kunert R. Humanization strategies for an anti-idiotypic antibody mimicking HIV-1 gp41. Protein Eng Des Sel 2010; 23:947-54.
41. Presta L G, Chen H, O'Connor S J, Chisholm V, Meng Y G, Krummen L, et al. Humanization of an anti-vascular endothelial growth factor monoclonal antibody for the therapy of solid tumors and other disorders. Cancer Res 1997; 57:4593-9.
42. Jones P T, Dear P H, Foote J, Neuberger M S, Winter G. Replacing the complementarity-determining regions in a human antibody with those from a mouse. Nature 1986; 321:522-5.
43. Villani M E, Morea V, Consalvi V, Chiaraluce R, Desiderio A, Benvenuto E, et al. Humanization of a highly stable single-chain antibody by structure-based antigen-binding site grafting. Mol Immunol 2008; 45:2474-85.
44. Haidar J N, Yuan Q A, Zeng L, Snavely M, Luna X, Zhang H, et al. A universal combinatorial design of antibody framework to graft distinct CDR sequences: A bioinformatics approach. Proteins 2011.
45. Hwang W Y, Almagro J C, Buss T N, Tan P, Foote J. Use of human germline genes in a CDR homology-based approach to antibody humanization. Methods 2005; 36:35-42.
46. Bertilaccio M T, Scielzo C, Simonetti G, Ten Hacken E, Apollonio B, Ghia P, et al. Xenograft models of chronic lymphocytic leukemia: problems, pitfalls and future directions. Leukemia 2013; 27:534-40.
47. Boyd S D, Gaeta B A, Jackson K J, Fire A Z, Marshall E L, Merker J D, et al. Individual variation in the germline Ig gene repertoire inferred from variable region gene rearrangements. J Immunol 2010; 184:6986-92.
48. Chang D K, Sui J, Geng S, Muvaffak A, Bai M, Fuhlbrigge R C, et al. Humanization of an anti-CCR4 antibody that kills cutaneous T-cell lymphoma cells and abrogates suppression by T-regulatory cells. Mol Cancer Ther 2012; 11:2451-61.
49. Han T, Abdel-Motal U M, Chang D K, *Sui* J, Muvaffak A, Campbell J, et al. Human anti-CCR4 minibody gene transfer for the treatment of cutaneous T-cell lymphoma. PLoS One 2012; 7:e44455.
50. Shultz L D, Schweitzer P A, Christianson S W, Gott B, Schweitzer I B, Tennent B, et al. Multiple defects in innate and adaptive immunologic function in NOD/LtSz-scid mice. J Immunol 1995; 154:180-91.
51. Chen S S, Chiorazzi N. Murine genetically engineered and human xenograft models of chronic lymphocytic leukemia. Seminars in hematology 2014; 51:188-205.
52. Bagnara D, Kaufman M S, Calissano C, Marsilio S, Patten P E, Simone R, et al. A novel adoptive transfer model of chronic lymphocytic leukemia suggests a key role for T lymphocytes in the disease. Blood 2011; 117:5463-72.
53. Durig J, Ebeling P, Grabellus F, Sorg U R, Mollmann M, Schutt P, et al. A novel nonobese diabetic/severe combined immunodeficient xenograft model for chronic lymphocytic leukemia reflects important clinical characteristics of the disease. Cancer Res 2007; 67:8653-61.
54. Aydin S, Grabellus F, Eisele L, Mollmann M, Hanoun M, Ebeling P, et al. Investigating the role of CD38 and functionally related molecular risk factors in the CLL NOD/SCID xenograft model. European journal of haematology 2011; 87:10-9.
55. Xing D, Ramsay A, Decker W. Dramatic reduction of chronic lymphocytic leukemia cells following adoptive transfer of cord blood natural killer cells using cord blood-engrafted NOD/SCID IL2Rgnull mice as a model. Blood 2009; 114:936.
56. George A J, Tutt A L, Stevenson F K. Anti-idiotypic mechanisms involved in suppression of a mouse B cell lymphoma, BCL1. J Immunol 1987; 138:628-34.
57. Timmerman J M, Czerwinski D K, Davis T A, Hsu F J, Benike C, Hao Z M, et al. Idiotype-pulsed dendritic cell vaccination for B-cell lymphoma: clinical and immune responses in 35 patients. Blood 2002; 99:1517-26.
58. Levy R, Ganjoo K N, Leonard J P, Vose J M, Flinn I W, Ambinder R F, et al. Active idiotypic vaccination versus control immunotherapy for follicular lymphoma. J Clin Oncol 2014; 32:1797-803.
59. Jilani I, O'Brien S, Manshuri T, Thomas D A, Thomazy V A, Imam M, et al. Transient down-modulation of CD20 by rituximab in patients with chronic lymphocytic leukemia. Blood 2003; 102:3514-20.
60. Golay J, Lazzari M, Facchinetti V, Bernasconi S, Borleri G, Barbui T, et al. CD20 levels determine the in vitro susceptibility to rituximab and complement of B-cell chronic lymphocytic leukemia: further regulation by CD55 and CD59. Blood 2001; 98:3383-9.
61. Pos W, Luken B M, Kremer Hovinga J A, Turenhout E A, Scheiflinger F, Dong J F, et al. V H1-69 germline encoded antibodies directed towards ADAMTS13 in patients with acquired thrombotic thrombocytopenic purpura. Journal of thrombosis and haemostasis: JTH 2009; 7:421-8.
62. Landau D A, Saadoun D, Calabrese L H, Cacoub P. The pathophysiology of HCV induced B-cell clonal disorders. Autoimmunity reviews 2007; 6:581-7.
63. Marasca R, Vaccari P, Luppi M, Zucchini P, Castelli I, Barozzi P, et al. Immunoglobulin gene mutations and frequent use of VH1-69 and VH4-34 segments in hepatitis C virus-positive and hepatitis C virus-negative nodal marginal zone B-cell lymphoma. Am J Pathol 2001; 159:253-61.
64. Ivanovski M, Silvestri F, Pozzato G, Anand S, Mazzaro C, Burrone O R, et al. Somatic hypermutation, clonal diversity, and preferential expression of the VH 51p1/$V_L$ kv325 immunoglobulin gene combination in hepatitis C virus-associated immunocytomas. Blood 1998; 91:2433-42.
65. Reff M E, Carner K, Chambers K S, Chinn P C, Leonard J E, Raab R, et al. Depletion of B cells in vivo by a chimeric mouse human monoclonal antibody to CD20. Blood 1994; 83:435-45.
66. Sui J, Li W, Murakami A, Tamin A, Matthews L J, Wong S K, et al. Potent neutralization of severe acute respiratory syndrome (SARS) coronavirus by a human mAb to 51 protein that blocks receptor association. Proceedings of the National Academy of Sciences of the United States of America 2004; 101:2536-41.
67. Long B R, Stoddart C A. Alpha interferon and HIV infection cause activation of human T cells in NSG-BLT mice. Journal of virology 2012; 86:3327-36.
68. Chang H, Biswas S, Tallarico A S, Sarkis P T, Geng S, Panditrao M M, et al. Human B-cell ontogeny in humanized NOD/SCID gammac(null) mice generates a diverse yet auto/poly- and HIV-1-reactive antibody repertoire. Genes Immun 2012; 13:399-410.
69. Biswas S, Chang H, Sarkis P T, Fikrig E, Zhu Q, Marasco W A. Humoral immune responses in humanized BLT mice immunized with West Nile virus and HIV-1 envelope proteins are largely mediated via human CD5+ B cells. Immunology 2011; 134:419-33.
70. Becker P D, Legrand N, van Geelen C M, Noerder M, Huntington N D, Lim A, et al. Generation of human antigen-specific monoclonal IgM antibodies using vaccinated "human immune system" mice. PLoS One 2010; 5.
71. Hayashi T, Treon S P, Hideshima T, Tai Y T, Akiyama M, Richardson P, et al. Recombinant humanized anti-CD40 monoclonal antibody triggers autologous antibody-dependent cell-mediated cytotoxicity against multiple myeloma cells. Br J Haematol 2003; 121:592-6.
72. Hezareh M, Hessell A J, Jensen R C, van de Winkel J G, Parren P W. Effector function activities of a panel of mutants of a broadly neutralizing antibody against human immunodeficiency virus type 1. J Virol 2001; 75:12161-8.

What is claimed is:

1. A method of selectively killing a B-cell expressing a IGHV1-69 BCR comprising contacting the B-cell with a chimeric antigen receptor comprising an huG6 antibody.

2. The method of claim 1, wherein said antibody is monovalent or bivalent.

3. The method of claim 1, wherein said antibody is a single chain antibody.

4. The method of claim 1, wherein the huG6 antibody comprises:
   a humanized heavy chain with three CDRs comprising an amino acid sequence GYTFTSYW (SEQ ID NO: 1); VSPGNSDT (SEQ ID NO: 2); and TRSRYGNNALDY (SEQ ID NO: 3); and a humanized light chain with three CDRs that include an amino acid sequence selected from the group consisting of the amino acid sequences of QGISSNIVW (SEQ ID NO: 4); HGT (SEQ ID NO: 5); and VQYSQFPPT (SEQ ID NO: 6).

5. The method of claim 1, wherein the huG6 antibody comprises:
   a. a heavy chain variable region comprising the amino acid sequence of SEQ ID NO: 14 and a light chain variable region comprising the amino acid sequence of SEQ ID NO:8;
   b. a heavy chain variable region comprising the amino acid sequence of SEQ ID NO: 10 and a light chain variable region comprising the amino acid sequence of SEQ ID NO: 12; or
   c. a heavy chain variable region comprising the amino acid sequence of SEQ ID NO: 14 and a light chain variable region comprising the amino acid sequence of SEQ ID NO:12.

6. The method of claim 1, wherein the chimeric antigen receptor is contacted with the B-cell prior to, concurrently with, or subsequent to contacting the B-cell with a chemotherapeutic agent.

7. A method of selectively killing a B-cell expressing a IGHV1-69 BCR comprising administering to a subject in need thereof a chimeric antigen receptor comprising an huG6 antibody.

8. The method of claim 7, wherein the subject has a cancer, an autoimmune disorder or an inflammatory disorder.

9. The method of claim 7, wherein the subject has chronic lymphocytic leukemia of B-cell phenotype (B-CLL), thrombotic thrombocytopenic purpura (TPP), idiopathic thrombocytopenia purpura (ITP) or cryoglobulinemia.

10. The method of claim 7, wherein said chimeric antigen receptor is administered prior to, concurrently with, or subsequent to the administration of a chemotherapeutic agent.

11. A method of selectively killing a B-cell expressing a IGHV1-69 BCR comprising contacting the B-cell with a chimeric antigen receptor comprising an huG6 antibody, wherein said chimeric antigen receptor comprising an huG6 antibody is contacted with the B-cell prior to, concurrently with, or subsequent to contacting the B-cell with a chemotherapeutic agent.

12. A method of selectively killing a B-cell expressing a IGHV1-69 BCR comprising administering to a subject in need thereof a chimeric antigen receptor comprising an huG6 antibody, wherein said chimeric antigen receptor comprising an huG6 antibody is administered to, concurrently with, or subsequent to the administration of a chemotherapeutic agent.

* * * * *